United States Patent
Seela et al.

(10) Patent No.: US 6,987,177 B2
(45) Date of Patent: Jan. 17, 2006

(54) MODIFIED OLIGONUCLEOTIDES, THEIR PREPARATION AND THEIR USE

(75) Inventors: Frank Seela, Osnabrück (DE); Horst Thomas, Hasbergen (DE)

(73) Assignee: Aventis Pharma Deutschland GmbH, Frankfurt (DE)

(*) Notice: Subject to any disclaimer, the term of this patent is extended or adjusted under 35 U.S.C. 154(b) by 100 days.

(21) Appl. No.: 10/222,825

(22) Filed: Aug. 19, 2002

(65) Prior Publication Data

US 2003/0096981 A1 May 22, 2003

Related U.S. Application Data

(62) Division of application No. 09/643,233, filed on Aug. 22, 2000, now Pat. No. 6,479,651, which is a continuation of application No. 09/144,112, filed on Aug. 31, 1998, now Pat. No. 6,150,510, which is a continuation of application No. 08/554,164, filed on Nov. 6, 1995, now Pat. No. 5,844,106.

(30) Foreign Application Priority Data

Nov. 4, 1994 (DE) .................. P 44 38 918

(51) Int. Cl.
| | |
|---|---|
| C07H 21/00 | (2006.01) |
| C07H 21/02 | (2006.01) |
| C07H 21/04 | (2006.01) |
| C12Q 1/68 | (2006.01) |
| C12P 19/34 | (2006.01) |

(52) U.S. Cl. ............ 536/23.1; 536/24.3; 536/24.5; 536/25.3; 536/27.2; 435/6; 435/91.1

(58) Field of Classification Search .......... 536/23.1, 536/24.3, 24.5, 23.5, 27.2; 435/6, 91.1
See application file for complete search history.

(56) References Cited

U.S. PATENT DOCUMENTS

| | | | |
|---|---|---|---|
| 5,241,060 A | 8/1993 | Engelhardt et al. | |
| 5,470,967 A | 11/1995 | Huie et al. | |
| 5,489,677 A | 2/1996 | Sanghui et al. | |
| 5,594,121 A | 1/1997 | Froehler | |
| 6,150,510 A | * 11/2000 | Seela et al. | ........... 536/22.1 |

FOREIGN PATENT DOCUMENTS

| | | |
|---|---|---|
| DE | 3 529 478 | 2/1987 |
| DE | 44 15 370 | 5/1994 |
| EP | 0 251 786 | 7/1987 |
| EP | 0 252 683 | 7/1987 |
| EP | 0 286 028 | 10/1988 |
| EP | 0 063 879 | 11/1992 |
| EP | 0 552 766 | 7/1993 |
| EP | 0 672 677 | 3/1995 |
| EP | 0 672 700 | 3/1995 |
| EP | 0 212 536 | 3/1997 |
| JP | 6-3241356 | 11/1988 |
| WO | 92/02258 | 2/1992 |
| WO | 92/06219 | 4/1992 |
| WO | 93/09127 | 10/1992 |
| WO | 93/10820 | 11/1992 |
| WO | 93/12130 | 12/1992 |
| WO | 94/24144 | 4/1994 |
| WO | 94/22892 | 10/1994 |
| WO | 95/04747 | 2/1995 |

OTHER PUBLICATIONS

Uhlman et al., "Antisense Oligonucleotides: A New Therapeutic Principle", Chemical Reviews, vol. 90, No. 4, pp. 544–584, (1990).

Beaucage et al., "Advances in the Synthesis of Oligonucleotides By the Phosphoramidite Approach" Tetrahedron Report No. 309, vol. 48, No. 12, pp. 2223–2311, (1992).

Ludwig, "A New Route to Nucleosides 5'–Triphosphates", Acta Biochim. et Biophys. Acad. Sci. Hung. Tetrahedron Report No. 309, vol. 48, No. 12, pp. 2223–2311, (1992).

Koga et al., "Altern. a,B–Oligothymidylates w/Altern. (3'–3') & (5'–5')–Internucleotidic Phosphod. Linkages ad Models for Antisense Oligodeoxribonuc.", J. Organ. Chem. 56(12), pp. 3757–3759, (1991).

McBridge et al., "N6 (N–Methyl–2–Pyrrolidine Amidine) Deoxyadenosine–A New Deoxynucleoside Protecting Group", Tetrahedron Letters, vol. 24, No. 29, pp. 2953–2956, (1983).

Ti et al., "Transient Protection: Efficient One–Flask Syntheses of Protected Deoxynucleosides", J. Am. Chem. Soc., No. 104, pp. 1316–1319, (1982).

Schaller et al., "Synthesis Of Deoxyribonucleosides–3' Phosphates", pp. 3821–3825, (1963).

Reese, "The Chemical Synthesis of Oligo–and Poly–Nucleotides By The Phosphotriester Approach", Tetrahedron Report No. 56, vol. 34, pp. 3143–3179, (1978).

Flockerzi et al., Synth. & Properties of 2'0– & 3'–0–(tert–Butyldimethylsily)–5'–0–(4–methoxytrity . . . Nucleoside, XXXVII, Liebigs Ann. Chem., pp. 1568–1585, (1981).

Froehler et al., "Synthesis of DNA via Deoxynucleoside H–Phosphonate Intermediates", Nucleic Acids Research, vol. 14, No. 13, pp. 5309–5407, (1986).

Sinha, Polymer Support Oligonucleotide Synthesis XVIB: Use of B–Cyanoethyl–N, N–Dialkylamino . . . Nucleic Acids Research, vol. 12, No. 11, pp. 4538–4557, (1984).

Sonveaux, "The Organic Chemistry Underlying DNA Synthesis", Bioorganic Chemistry vol. 14, pp. 274–325, (1986).

(Continued)

*Primary Examiner*—Jezia Riley
(74) *Attorney, Agent, or Firm*—Karen I. Krupen

(57) ABSTRACT

Modified oligonucleotides which possess at least one substituted 7-deazapurine base form more stable hybridization complexes with nucleic acids than unsubstituted analogs. They are useful as inhibitors of gene expression, as probes for detecting nucleic acids, as aids in molecular biology and as pharmaceuticals or diagnostic agents. Processes for preparing them are provided.

11 Claims, No Drawings

OTHER PUBLICATIONS

Milligan et al., "Current Concepts in Antisense Drug Design", Journal of Medicinal Chemistry, vol. 36, No. 14, pp. 1923–1937, (1993).

Chollet et al., "DNA Containing The Base Analogue 2–Aminoadenine: Preparation, Use As Hybirdization Probes and Cleavage By Restriction Endonucleases", Nucleic Acids Res. vol. 16, No. 1, pp. 305–317, (1988).

Watanabe et al., Thiocyanation of Tubercidin of Tubercidin and Its Derivatization to 6–Proply . . . Nucleosides & Nucleotides, vol. 1, No. 2, pp. 191–203, (1982).

Nair et al., "Novel, Stable Congeners of the Antiretroviral Compound 2',3'–Dideoxyadenosine", J. Am. Chem. Soc., vol. 111, pp. 8502–8504, (1989).

Grein et al., "3–Deaza and 7–Deazapurines: Duplex Stability of Oligonucleotides Containing Modified Adenine and Guanine Bases," Bioorg. Med. Chem. Lett., Bd. 4(2): 971–76 (1994).

Cottam et al., "Synthesis and Biological Activity of Certain 6–Substituted and 2,6–Disubstituted 2'–Deoxytubercidins," J. Med. Chem., 28: 1461–67 (1985).

Seela et al., "Assignment of Anomeric Configuration of D–Ribo–, Arabino–, 2' Deoxyribo–, and 2',3'–t Dideoxyribonucleosides by NOE Difference Spectroscopy," Nucleosides, Nucleotides, bd. 8: 587–97 (1989).

Eger et al., "Synthesis of Pyrrolo 2,3–dlpyrimidine Ribosides and their Potential in Chemotherapeutics," J. Heterocyclic Chem., 27: 2069–75 (1990).

Prober et al., "A System for Rapid DNA Sequencing with Fluorescent Chain–Terminating Dideoxynucleotides," Science 238: 336–41 (1987).

Winkeler et al., "Synthesis and Furanosie/Pyranosid–Isomerisierung von 7–Desaza–2'desoxy–7methylguanosin," Lieb. Ann. Chem. 708–21 (1984) (English abstract provided).

Nakagawa et al., "Poly(8–bromodeoxyadenylic acid): Properties of the Polymer and Contrast with the Ribo of nucleotide Analogue" Biochemistry 23:4219–25 (1984).

Seela et al., "Oligonucleotides with Unnatural bases or an altered sugar–phosphate bacbone" Nucleid Acid Symp. Set. 31:1511–52 (1994).

Livak et al., "Detection of single base differences using biotinylated nucleotides with very long linker arms", Nucleic Acids Res. 20(18): 4831–37 (1992).

Hughes et al., "2', 5'–Oligoadenylates and Related 2', 5'–Oligonucleotides Analogs," Biochemistry 22(9) 2116–26 (1983) Abstract.

Seela et al, "Duplex Stabilization of DNA," Helv. Chim. ACTA 78(1): 94–108 (1995) Abstract.

Nakagawa et al., "Poly(2–amino–t–methyldeoxyadenylis acids): Contrasting Effects in Deoxy– and Ribopolynucleotides of 2–Amino and 8–Methyl Substituents," Biochemistry 26: 7159–65 (1987).

Seela et al., "Synthesis of Certain 5–Substituted 2'–Deoxytubercidin Derivatives," helv. Chim. ACTA 77:897–903, (1994).

Turro et al., "Photochemical Analogue of the Bergman Cycloaromatization Reaction," Tetrahedron 35(44), pp. 8089–92 (1994).

Beaucage et al., "The Functionalization of Oligonucleotides Via Phosphoramidite Derivatives," Tetrahedron 49(10): 1925–63 (1993).

Seela et al., "Poly(adenylic acids) containing the antibiotic tubercidin—base pairing and hydrolysis by nuclease $S_1$," Nucleic Acids. Res. 10(4): 1389–97 (1982).

Auflage et al., "Preformulation," Remington's Pharmaceutical Science 76: 1415–21 (1985).

\* cited by examiner

SEQUENCE LISTING

<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: Antisense Oligonucleotide

<400> SEQUENCE: 1
acacccaatt ctgaaaatgg                                              20

<210> SEQ ID NO 2
<211> LENGTH: 20
<212> TYPE: DNA
<213> ORGANISM: Artificial
<220> FEATURE:
<223> OTHER INFORMATION: Antisense Oligonucleotide

<400> SEQUENCE: 2
aggtccctgt tcgggcgcca                                              20

<210> SEQ ID NO 3
<211> LENGTH: 28

```
<212> TYPE: DNA
<213> ORGANISM: Artificial
<220> FEATURE:
<223> OTHER INFORMATION: Antisense Oligonucleotide

<400> SEQUENCE: 3
gtcgacaccc aattctgaaa atggataa                                          28

<210> SEQ ID NO 4
<211> LENGTH: 25
<212> TYPE: DNA
<213> ORGANISM: Artificial
<220> FEATURE:
<223> OTHER INFORMATION: Antisense Oligonucleotide

<400> SEQUENCE: 4
gctatgtcga cacccaattc tgaaa                                             25

<210> SEQ ID NO 5
<211> LENGTH: 31
<212> TYPE: DNA
<213> ORGANISM: Artificial
<220> FEATURE:
<223> OTHER INFORMATION: Antisense Oligonucleotide

<400> SEQUENCE: 5
tcgtcgctgt ctccgcttct tcttcctgcc a                                      31

<210> SEQ ID NO 6
<211> LENGTH: 17
<212> TYPE: DNA
<213> ORGANISM: Artificial
<220> FEATURE:
<223> OTHER INFORMATION: Antisense Oligonucleotide

<400> SEQUENCE: 6
gcggatgggg gtcggtg                                                      17

<210> SEQ ID NO 7
<211> LENGTH: 15
<212> TYPE: DNA
<213> ORGANISM: Artificial
<220> FEATURE:
<223> OTHER INFORMATION: Antisense Oligonucleotide

<400> SEQUENCE: 7
cagctgcaac ccagc                                                        15

<210> SEQ ID NO 8
<211> LENGTH: 21
<212> TYPE: DNA
<213> ORGANISM: Artificial
<220> FEATURE:
<223> OTHER INFORMATION: Antisense Oligonucleotide

<400> SEQUENCE: 8
ggctgctgga gcggggcaca c                                                 21

<210> SEQ ID NO 9
<211> LENGTH: 15
<212> TYPE: DNA
<213> ORGANISM: Artificial
<220> FEATURE:
<223> OTHER INFORMATION: Antisense Oligonucleotide

<400> SEQUENCE: 9
```
aacgttgagg ggcat                                                15

<210> SEQ ID NO 10
<211> LENGTH: 18
<212> TYPE: DNA
<213> ORGANISM: Artificial
<220> FEATURE:
<223> OTHER INFORMATION: Antisense Oligonucleotide

<400> SEQUENCE: 10
gtgccggggt cttcgggc                                             18

<210> SEQ ID NO 11
<211> LENGTH: 21
<212> TYPE: DNA
<213> ORGANISM: Artificial
<220> FEATURE:
<223> OTHER INFORMATION: Antisense Oligonucleotide

<400> SEQUENCE: 11
ggagaacatc atggtcgaaa g                                         21

<210> SEQ ID NO 12
<211> LENGTH: 22
<212> TYPE: DNA
<213> ORGANISM: Artificial
<220> FEATURE:
<223> OTHER INFORMATION: Antisense Oligonucleotide

<400> SEQUENCE: 12
cccgagaaca tcatggtcga ag                                        22

<210> SEQ ID NO 13
<211> LENGTH: 20
<212> TYPE: DNA
<213> ORGANISM: Artificial
<220> FEATURE:
<223> OTHER INFORMATION: Antisense Oligonucleotide

<400> SEQUENCE: 13
ggggaaagcc cggcaagggg                                           20

<210> SEQ ID NO 14
<211> LENGTH: 20
<212> TYPE: DNA
<213> ORGANISM: Artificial
<220> FEATURE:
<223> OTHER INFORMATION: Antisense Oligonucleotide

<400> SEQUENCE: 14
cacccgcctt ggcctcccac                                           20

<210> SEQ ID NO 15
<211> LENGTH: 18
<212> TYPE: DNA
<213> ORGANISM: Artificial
<220> FEATURE:
<223> OTHER INFORMATION: Antisense Oligonucleotide

<400> SEQUENCE: 15
gggactccgg cgcagcgc                                             18

<210> SEQ ID NO 16
<211> LENGTH: 20
<212> TYPE: DNA
<213> ORGANISM: Artificial

```
<220> FEATURE:
<223> OTHER INFORMATION: Antisense Oligonucleotide

<400> SEQUENCE: 16
ggcaaacttt cttttcctcc                                                 20

<210> SEQ ID NO 17
<211> LENGTH: 19
<212> TYPE: DNA
<213> ORGANISM: Artificial
<220> FEATURE:
<223> OTHER INFORMATION: Antisense Oligonucleotide

<400> SEQUENCE: 17
gggaaggagg aggatgagg                                                  19

<210> SEQ ID NO 18
<211> LENGTH: 21
<212> TYPE: DNA
<213> ORGANISM: Artificial
<220> FEATURE:
<223> OTHER INFORMATION: Antisense Oligonucleotide

<400> SEQUENCE: 18
ggcagtcatc cagcttcgga g                                               21

<210> SEQ ID NO 19
<211> LENGTH: 18
<212> TYPE: DNA
<213> ORGANISM: Artificial
<220> FEATURE:
<223> OTHER INFORMATION: Antisense Oligonucleotide

<400> SEQUENCE: 19
gcagtaagca tccatatc                                                   18

<210> SEQ ID NO 20
<211> LENGTH: 20
<212> TYPE: DNA
<213> ORGANISM: Artificial
<220> FEATURE:
<223> OTHER INFORMATION: Antisense Oligonucleotide

<400> SEQUENCE: 20
cccccaccac ttcccctctc                                                 20

<210> SEQ ID NO 21
<211> LENGTH: 20
<212> TYPE: DNA
<213> ORGANISM: Artificial
<220> FEATURE:
<223> OTHER INFORMATION: Antisense Oligonucleotide

<400> SEQUENCE: 21
ctcccccacc acttcccctc                                                 20

<210> SEQ ID NO 22
<211> LENGTH: 19
<212> TYPE: DNA
<213> ORGANISM: Artificial
<220> FEATURE:
<223> OTHER INFORMATION: Antisense Oligonucleotide

<400> SEQUENCE: 22
gctgggagcc atagcgagg                                                  19
```

-continued

<210> SEQ ID NO 23
<211> LENGTH: 21
<212> TYPE: DNA
<213> ORGANISM: Artificial
<220> FEATURE:
<223> OTHER INFORMATION: Antisense Oligonucleotide

<400> SEQUENCE: 23
actgctgcct cttgtctcag g                                              21

<210> SEQ ID NO 24
<211> LENGTH: 22
<212> TYPE: DNA
<213> ORGANISM: Artificial
<220> FEATURE:
<223> OTHER INFORMATION: Antisense Oligonucleotide

<400> SEQUENCE: 24
caatcaatga cttcaagagt tc                                             22

<210> SEQ ID NO 25
<211> LENGTH: 18
<212> TYPE: DNA
<213> ORGANISM: Artificial
<220> FEATURE:
<223> OTHER INFORMATION: Antisense Oligonucleotide

<400> SEQUENCE: 25
gtgtcggggt ctccgggc                                                  18

<210> SEQ ID NO 26
<211> LENGTH: 15
<212> TYPE: DNA
<213> ORGANISM: Artificial
<220> FEATURE:
<223> OTHER INFORMATION: Antisense Oligonucleotide

<400> SEQUENCE: 26
cacgttgagg ggcat                                                     15

<210> SEQ ID NO 27
<211> LENGTH: 19
<212> TYPE: DNA
<213> ORGANISM: Artificial
<220> FEATURE:
<223> OTHER INFORMATION: Antisense Oligonucleotide

<400> SEQUENCE: 27
gtcttccata agttactca                                                 19

<210> SEQ ID NO 28
<211> LENGTH: 18
<212> TYPE: DNA
<213> ORGANISM: Artificial
<220> FEATURE:
<223> OTHER INFORMATION: Antisense Oligonucleotide

<400> SEQUENCE: 28
gatcaggcgt gcctcaaa                                                  18

<210> SEQ ID NO 29
<211> LENGTH: 12
<212> TYPE: DNA
<213> ORGANISM: Artificial
<220> FEATURE:
<223> OTHER INFORMATION: Synthesized Oligonucleotide

```
<400> SEQUENCE: 29
aaaaaaaaaa aa                                                              12

<210> SEQ ID NO 30
<211> LENGTH: 12
<212> TYPE: DNA
<213> ORGANISM: Artificial
<220> FEATURE:
<223> OTHER INFORMATION: Synthesized oligonucleotide

<400> SEQUENCE: 30
tttttttttt tt                                                              12

<210> SEQ ID NO 31
<211> LENGTH: 12
<212> TYPE: DNA
<213> ORGANISM: Artificial
<220> FEATURE:
<223> OTHER INFORMATION: Synthesized Oligonucleotide

<400> SEQUENCE: 31
atatatatat at                                                              12

<210> SEQ ID NO 32
<211> LENGTH: 8
<212> TYPE: DNA
<213> ORGANISM: Artificial
<220> FEATURE:
<223> OTHER INFORMATION: Synthesized Oligonucleotide

<400> SEQUENCE: 32 gcgcgcgc                                                                    8
```

MODIFIED OLIGONUCLEOTIDES, THEIR PREPARATION AND THEIR USE

The instant application is a divisional of U.S. Ser. No. 09/643,233, filed Aug. 22, 2000 now U.S. Pat. No. 6,479, 651, which is a continuation of U.S. Ser. No. 09/144,112, filed Aug. 31, 1998, now U.S. Pat. No. 6,150,510, issued Nov. 21, 2000, which is a continuation of U.S. Ser. No. 08/554,164, filed Nov. 6, 1995, now U.S. Pat. No. 5,844, 106, issued Dec. 1, 1998.

BACKGROUND OF THE INVENTION

The present invention relates to novel oligonucleotides which contain modified bases and which possess valuable physical, biological and pharmacological properties, to a process for their preparation and to their use as inhibitors of gene expression (antisense oligonucleotides, ribozymes, sense oligonucleotides and triplex-forming oligonucleotides), as probes for detecting nucleic acids, as aids in molecular biology and as pharmaceuticals or diagnostic agents.

Numerous chemical modifications of oligonucleotides are known from the literature. These modifications can affect the sugar-phosphate skeleton or the nucleotide bases. Reviews of the state of the art are provided, for example, by Uhlmann & Peyman, Chem. Rev. 1990, 90, 543 and Milligan et al., J. Med. Chem. 1993, 36, 1923.

As a rule, it is necessary to modify oligonucleotides chemically since unmodified oligonucleotides are very rapidly degraded by nucleolytic activities both in cells and in the cell culture medium. Stabilization against nucleolytic degradation can be achieved by replacing the sugar-phosphate backbone or by modifying the phosphate bridge, the sugar moiety or the nucleotide base [Milligan et al., above and Uhlmann & Peyman, above].

In addition to modifications which lead to oligonucleotides which possess increased stability towards nucleolytic degradation, those modifications are also of interest which alter the hybridization behavior of the modified oligonucleotides such that the latter are able, for example, to form more stable hybridization complexes (duplexes) with intracellular nucleic acids (so-called target nucleic acids). It is possible to alter the hybridization properties of oligonucleotides by, for example, modifying the bases. The altered hybridization properties of oligonucleotides which have been modified in this way can be recognized, for example, from the melting temperatures ($T_m$ values) of the duplexes, which temperatures are different from those obtained with the unmodified oligonucleotides.

Thus, oligonucleotides which contain 5-bromouracil, for example, form more stable hybridization complexes with the complementary nucleic acids than do oligonucleotides which contain the corresponding, unsubstituted bases (uracil) [G. D. Fasman, CRC Handbook of Biochemistry and Molecular Biology, 3rd edition, 1975, Nucleic Acids, Vol. I , 58–585].

In addition, PCT Application WO 93/10820 discloses oligonucleotides which contain modified uracil or cytosine bases and which are able to form duplex or triplex structures with the target nucleic acids which are more stable than those formed by the unmodified oligonucleotides. Oligonucleotides which contain the base analog 2-aminoadenine have also been reported to exhibit improved hybridization properties [Chollet et al., (1988), Nucleic Acid Research, 16, 305–317]. German Patent Application P4415370.8 discloses that incorporating 8-azapurine bases into oligonucleotides increases the stability of the corresponding hybridization complexes with the target nucleic acids. In addition WO 93/09127 discloses oligonucleotides which contain substituted or unsubstituted 7-deazapurine bases and which, as a result, are more readily able to form triplex structures with the target molecules (double-stranded DNA). Oligonucleotides which contain 7-deazapurine bases which are substituted in the 7 position are also disclosed in WO 94/22892 and WO 94/24144.

However, it is not possible to predict the base modifications which will lead to an increase in duplex stability. Thus, numerous examples are known of base modifications which diminish duplex stability. Thus, PCT Application WO 92/002258 describes pyrimidine-modified oligonucleotides which exhibit decreased binding affinity for the target nucleic acids. Methyl or bromine substituents which are introduced at the 8 position of the purine ring also decrease the stability of the corresponding duplexes [E. N. Kanaya et al., Biochemistry (1987) 26 7159, and Biochemistry, 1984, 23, 4219]. Oligonucleotides which contain 7-deazaadenine form significantly fewer stable duplexes with complementary oligonucleotides than do oligonucleotides which contain adenine [Seela et al., Nucleic Acid Research (1982) 10, 1389].

SUMMARY OF THE INVENTION

The object of the present invention is, therefore, to make available novel oligonucleotides which possess advantageous properties.

It has now been found, surprisingly, that oligonucleotides which possess at least one substituted 7-deazapurine base form hybridization complexes with the target nucleic acids which are significantly more stable than those formed by comparable oligonucleotides which possess unsubstituted 7-deazapurine bases.

The invention consequently relates to oligonucleotides of the formula I

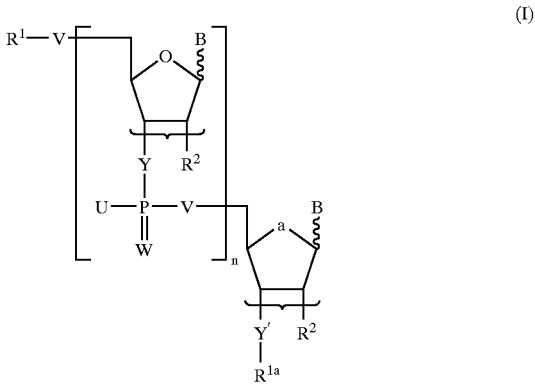

and the physiologically tolerated salts thereof, in which

B are, independently of each other, a base which is customary in nucleotide chemistry, and at least one B is a base of the formula II

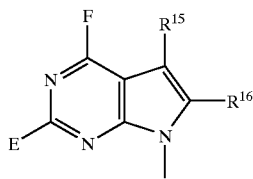
(II)

in which
R$^{15}$ and R$^{16}$ are, independently of each other,
1. hydrogen,
2. halogen,
3. (C$_1$–C$_{10}$)-alkyl,
4. (C$_2$–C$_{10}$)-alkenyl,
5. (C$_2$–C$_{10}$)-alkynyl,
6. NO$_2$,
7. NH$_2$,
8. cyano,
9. —S—(C$_1$–C$_6$)-alkyl,
10. (C$_1$–C$_6$)-alkoxy,
11. (C$_6$–C$_{20}$)-aryloxy,
12. SiH$_3$, 13. 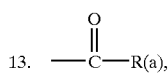

14. a radical as described under 3., 4. or 5. which is substituted by one or more radicals from the group SH, S—(C$_1$–C$_6$)-alkyl, (C$_1$–C$_6$)-alkoxy, OH, —NR(c)R(d), —CO—R(b), —NH—CO—NR(c)R(d), —NR(c)R(g), —NR(e)R(f) or —NR(e)R(g), or by a polyalkyleneglycol radical of the formula —[O—(CH$_2$)$_r$]$_s$—NR(c)R(d), where r and s are, independently of each other, an integer between 1 and 18, preferably between 1 and 6, with it being possible for functional groups such as OH, SH, —CO—R(b), —NH—CO—NR(c)R(d), —NR(c)R(d), —NR(e)R(f), —NR(e)R(g) or —NR(c)R(g) additionally to be linked to one or more groups, where appropriate via a further linker, which favor intracellular uptake or serve for labeling a DNA or RNA probe, or, when the oligonucleotide analog hybridizes to the target nucleic acid, attack the latter while binding, cross-linking or cleaving, or 15. a radical as defined under 3., 4. or 5. in which from one to all the H atoms are substituted by halogen, preferably fluorine;

R(a) is OH, (C$_1$–C$_6$)-alkoxy, (C$_6$–C$_{20}$)-aryloxy, NH$_2$ or NH-T, where T is an alkylcarboxyl group or alkylamino group which is linked to one or more groups, where appropriate via a further linker, which favor intracellular uptake or serve for labeling a DNA or RNA probe or, when the oligonucleotide analog hybridizes to the target nucleic acid, attack the latter while binding, cross-linking or cleaving, R(b) is hydroxyl, (C$_1$–C$_6$)-alkoxy or —NR(c)R(d),
R(c) and R(d) are, independently of each other, R or (C$_1$–C$_6$)-alkyl which is unsubstituted or substituted by —NR(e)R(f) or —NR(e)R(g),
R(e) and R(f) are, independently of each other, H or (C$_1$–C$_6$)-alkyl,
R(g) is (C$_1$–C$_6$)-alkyl-COOH; with the proviso that R$^{15}$ and R$^{16}$ cannot each simultaneously be hydrogen, NO$_2$, NH$_2$, cyano or SiH$_3$;

E and F are, independently of each other, H, OH or NH$_2$,
R$^1$ is hydrogen, C$_1$–C$_{18}$-alkyl, C$_2$–C$_{18}$-alkenyl, C$_2$–C$_{18}$-alkynyl, C$_2$–C$_{18}$-alkylcarbonyl, C$_3$–C$_{19}$-alkenylcarbonyl, C$_3$–C$_{19}$-alkynylcarbonyl, (C$_6$–C$_{14}$)-aryl-(C$_1$–C$_8$)-alkyl, a protective group which is customary in nucleotide chemistry, or a radical of the formula IIIa

(IIIa)

R$^{1a}$ is hydrogen, C$_1$–C$_8$-alkyl, C$_2$–C$_{18}$-alkenyl, C$_2$–C$_{18}$-alkynyl, C$_2$–C$_{18}$-alkylcarbonyl, C$_3$–C$_{19}$-alkenylcarbonyl, C$_3$–C$_{19}$-alkynylcarbonyl, (C$_6$–C$_{14}$)-aryl-(C$_1$–C$_8$)-alkyl, or a radical of the formula IIIb

(IIIb)

R$^2$ is hydrogen, hydroxyl, C$_1$–C$_{18}$-alkoxy, C$_1$–C$_6$-alkenyloxy, in particular allyloxy, halogen, in particular F, azido or NH$_2$;
a is oxy, sulfanediyl or methylene;
n is an integer $\geq 1$;
W is oxo, thioxo or selenoxo;
V is oxy, sulfanediyl or imino;
Y is oxy, sulfanediyl, imino or methylene;
Y' is oxy, sulfanediyl, imino, (CH$_2$)$_m$ or V(CH$_2$)$_m$, in which
m is an integer from 1 to 18;
X is hydroxyl or mercapto;
U is hydroxyl, mercapto, SeH, C$_1$–C$_{18}$-alkoxy, C$_1$–C$_{18}$-alkyl, C$_6$–C$_{20}$-aryl, (C$_6$–C$_{14}$)aryl-(C$_1$–C$_8$)-alkyl, NHR$^3$, NR$^3$R$^4$ or a radical of the formula IV

(IV)

in which
R$^3$ is C$_1$–C$_{18}$-alkyl, C$_6$–C$_{20}$-aryl, (C$_6$–C$_{14}$)-aryl-(C$_1$–C$_8$)-alkyl, —(CH$_2$)$_c$—[NH(CH$_2$)$_c$]$_d$—NR$^6$R$^6$, in which c is an integer from 2 to 6 and d is an integer from 0 to 6, and R$^6$ is, independently of each other, hydrogen or C$_1$–C$_6$-alkyl or C$_1$–C$_4$-alkoxy-C$_1$–C$_6$-alkyl;
R$^4$ is C$_1$–C$_{18}$-alkyl, C$_6$–C$_{20}$-aryl or (C$_6$–C$_{10}$)-aryl-(C$_1$–C$_8$)-alkyl, or, in the case of NR$^3$R$^4$, is, together with R$^3$ and the nitrogen atom carrying them, a 5-6-membered heterocyclic ring which can additionally contain a further heteroatom from the series O, S and N,
p is an integer from 1 to 100,
q is an integer from 0 to 22,
R$^5$ is hydrogen or a functional group such as, for example, hydroxyl, amino, C$_1$–C$_{18}$-alkylamino, COOH, CONH$_2$, COO(C$_1$–C$_4$)-alkyl or halogen;
Z and Z' are, independently of each other, hydroxyl, mercapto, SeH, C$_1$–C$_{22}$-alkoxy, —O—(CH$_2$)$_b$—NR$^6$R$^7$, in which b is an integer from 1 to 6, and R$^7$ is C$_1$–C$_6$-alkyl or R$^6$ and R$^7$, together with the nitrogen atom carrying them, form a 3–6-membered ring, $C_1-C_{18}$-alkyl, $C_6-C_{20}$-aryl, $(C_6-C_{14})$-aryl-$(C_1-C_8)$-alkyl, $(C_6-C_{14})$-aryl-$(C_1-C_8)$-alkoxy, where is also heteroaryl and aryl is optionally substituted by 1, 2 or 3 identical or different radicals from the group carboxyl, amino, nitro, $C_1-C_4$-alkylamino, $C_1-C_6$-alkoxy, hydroxyl, halogen and cyano, $C_1-C_{18}$-alkylmercapto, $NHR^3$, $NR^3R^4$, a radical of the formula IV or a group which favors intracellular uptake or serves for labeling a DNA probe or, when the oligonucleotide analog hybridizes to the target nucleic acid, attacks the latter while binding, cross-linking or cleaving, and the curved bracket indicates that $R^2$ and the adjacent phosphoryl or —Y'—$R^{1a}$ radical can either be located in the 2' and 3' positions or else, conversely, in the 3' and 2' position, with it being possible for each nucleotide to be present in its D or L configuration, and for the base B to be located in the α or β position.

DETAILED DESCRIPTION

Bases which are customary in nucleotide chemistry are to be understood to mean, for example, natural bases, such as adenine, cytosine, thymine, guanine, uracil or hypoxanthine, or unnatural bases, such as, for example, purine, 8-azapurine, 2,6-diaminopurine, 7-deazaadenine, 7-deazaguanine, $N^4,N^4$-ethanocytosine, $N^6,N^6$-ethano-2,6-diaminopurine, pseudoisocytosine, 5-methylcytosine, 5-fluorouracil, 5-$(C_3-C_6)$-alkynyluracil, 5-$(C_3-C_6)$-alkynylcytosine, or their prodrug forms.

Oligonucleotides of the formula I are preferred which possess at least one 7-deazaguanine base (E is $NH_2$ and F is OH) or 7-deazaadenine base (E is H and F is $NH_2$) which is substituted at the 7 position.

Oligonucleotides of the formula I are particularly preferred which possess at least one 7-deazaadenine base which is substituted at the 7 position and, where appropriate, one or more 7-deazaguanine bases which are substituted at the 7 position, in addition.

Oligonucleotides of the formula I which possess at least one 7-deazapurine base which is substituted at the 7 and 8 positions (=disubstituted 7-deazapurine bases) represent a further preferred embodiment of the present invention. Oligonucleotides of the formula I having disubstituted 7-deazapurine bases are preferred in which the disubstituted 7-deazapurine bases carry a substituent at the 8 position which is defined under $R^{16}$ 2., 3., 4., 5., 14. and 15. A halogen, for example fluorine, is particularly preferred at the 8 position. The substituents defined under $R^{15}$ 3., 4., 5., 14. and 15., in particular hexynyl, are preferred substituents at the 7 position. Oligonucleotides of the formula I are also preferred in which $R^{15}$ is
1. $NO_2$,
2. $NH_2$,
3. —S—$(C_1-C_6)$-alkyl,
4. $(C_1-C_6)$-alkoxy,
5. $(C_6-C_{20})$-aryloxy,
6. $SiH_3$, 7. 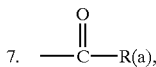 —C—R(a), 8. $(C_1-C_{10})$-alkyl, $(C_2-C_{10})$-alkenyl or $(C_2-C_{10})$-alkynyl which is substituted by one or more radicals from the group SH, S—$(C_1-C_6)$-alkyl, $(C_1-C_6)$-alkoxy, OH, —NR(c)R(d), —CO—R(b), —NH—CO—NR(c)R(d), —NR(c)R(g), —NR(e)R(f) or —NR(e)R(g), or by a polyalkylene glycol radical of the formula —[O—$(CH_2)_r]_s$—NR(c)R(d), where r and s are, independently of each other, an integer between 1 and 18, preferably 1 and 6, with it being possible for functional groups such as OH, SH, —CO—R(b), —NH—CO—NR(c)R(d), —NR(c)R(d), —NR(e)R(f), —NR(e)R(g) or —NR(c)R(g) additionally to be linked to one or more groups, where appropriate via a further linker, which favor intracellular uptake or serve for labeling a DNA or RNA probe or, when the oligonucleotide analog hybridizes to the target nucleic acid, attack the latter while binding, cross-linking or cleaving, or 9. $(C_1-C_{10})$-alkyl, $(C_2-C_{10})$-alkenyl or $(C_2-C_{10})$-alkynyl in which from one to all the H atoms are substituted by halogen, preferably fluorine; and $R^{16}$ is hydrogen.

If only the 7 position of the 7-deazapurine bases is substituted ($R^{16}$=H), $C_1-C_{10}$-alkyl, $C_2-C_{10}$-alkenyl or $C_2-C_{10}$-alkynyl radicals, in which from one to all the H atoms are substituted by halogen, preferably fluorine, are then particularly preferred for the 7 position.

Generally, 7-deazapurine-containing oligonucleotides are preferred in which the 7-deazapurine bases bear electron-attracting substituents at the 7 position and/or 8 position.

Oligonucleotides of the formula I are also preferred in which the base is located in the β position on the sugar, the nucleotides are in the D configuration, $R^2$ is located in the 2' position and a is oxy.

The 7 position of the azapurine ring system is to be understood to mean the position at which the substituent $R^{15}$ is located. Correspondingly, the substituent $R^{16}$ is located at the 8 position.

When attaching to complementary nucleic acids (target nucleic acids), the novel oligonucleotides exhibit a binding affinity which is superior to that exhibited by the natural oligonucleotides.

A further advantage of the novel oligonucleotides is that their stability towards acids and nucleases is increased as compared with that of oligonucleotides which contain natural purine bases.

It is advantageous if additional modifications, for example of the phosphate backbone, the ribose unit or the oligonucleotide ends, are introduced into these oligonucleotides when they are to be used therapeutically [J. S. Cohen, Topics in Molecular and Structural Biology 12 (1989) Macmillan Press, E. Uhlmann et al., above]. For example, modifications, which are known per se, of the sugar phosphate backbone result in the novel oligonucleotides becoming even more efficiently protected against nuclease attack, which is advantageous.

Compounds of the formula I are also preferred, therefore, in which V, Y, Y' and W have the meaning of thioxo, selenoxo, oxy, oxo, sulfanediyl, imino or methylene, and U has the meaning of hydroxyl, mercapto or methyl. These compounds are very particularly preferred if $R^2$ additionally is hydroxyl or hydrogen, in particular hydrogen.

Compounds of the formula I in which $R^1$ and $R^{1a}$ are hydrogen also represent a preferred embodiment.

Compounds of the formula I are very particularly preferred in which $R^1$ and/or $R^{1a}$ is hydrogen, $R^2$ is hydroxyl or hydrogen, U is hydroxyl or mercapto, and V, Y, Y' and W have the meaning of thioxo, oxy, oxo or hydroxyl.

Protective groups which are customary in nucleotide chemistry are to be understood to mean, for example, amino protective groups, hydroxyl protective groups or other protective groups as described in [E. Sonveaux, 1986, Bioorganic Chemistry, 14, 274–325 or S. L. Beaucage et al., 1992, Tetrahedron, 48, 2223–2311].

Alkyl, alkenyl and alkynyl may be straight-chain or branched. The same also applies, in a corresponding manner, to radicals which are derived from them, such as alkanoyl or alkoxy.

$(C_1-C_{10})$-Alkyl is, in particular, methyl, ethyl, propyl, isopropyl, butyl, isobutyl, pentyl, hexyl and heptyl. Examples of halogenated $(C_1-C_{10})$-alkyls are $CHF_2$, $CF_3$, $CH_2F$, $CF_3$—$CH_2$—$CH_2$—, $CF_3$—$CF_2$—$CH_2$, $CF_3(CF_2)_6$—$CH_2$,

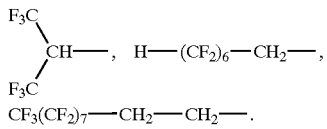

$CF_3(CF_2)_7$—$CH_2$—$CH_2$—.

$(C_2-C_{10})$-Alkenyl is, for example, vinyl (—CH=CH$_2$), 1-propenyl (—CH=CH—CH$_3$), 2-methyl-1-propenyl (—CH=C(CH$_3$)—CH$_3$), 1-butenyl (—CH=CH—CH$_2$—CH$_3$), 1-pentenyl, 1-hexenyl, 1-heptenyl and 1-octenyl. Examples of halogenated $(C_2-C_{10})$-alkenyls are —CH=CF$_2$, —CH=CH—CF$_3$ and —CF=CF—CF$_3$.

$(C_2-C_{10})$-Alkynyl is, for example, ethynyl (—C≡CH), 1-propynyl (—C≡C—CH$_3$), 1-butynyl (—C≡C—CH$_2$—CH$_3$), 3-methyl-butynyl (—C≡C—CH(CH$_3$)—CH$_3$), 3,3-dimethyl-butynyl (—C≡C—C(CH$_3$)$_3$), 1-pentynyl, 1,3-pentadiynyl (—C≡C—C≡C—CH$_3$), 1-hexynyl and 1-heptynyl. Examples of halogenated $(C_2-C_{10})$-alkynyls are —C≡C—CH$_2$F, —C≡C—CF$_3$, —C≡C—(CH$_2$)$_3$—CF$_3$ and —C≡C—(CF$_2$)$_3$—CF$_3$.

Cycloalkyl is also understood to mean alkyl-substituted rings.

$(C_6-C_{20})$-Aryl is, for example, phenyl, naphthyl or biphenylyl, preferably phenyl.

Halogen is to be understood to mean iodine, bromine, chlorine or fluorine.

Heteroaryl is understood to mean, in particular, radicals which are derived from phenyl or naphthyl in which one or more CH groups are replaced by N and/or in which at least two adjacent CH groups are replaced (with the formation of a five-membered aromatic ring) by S, NH or O. In addition, one or both atoms of the condensation site of bicyclic radicals can be N atoms (as in indolizinyl).

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

The morpholinyl radical and the imidazolidinyl radical may be mentioned as examples of NR$^3$R$^4$ groups in which R$^3$ and R$^4$, together with the nitrogen atom carrying them, form a 5- to 6-membered heterocyclic ring which additionally contains a further heteroatom.

Physiologically tolerated salts of compounds of the formula (I) are understood to mean both inorganic and organic salts, as described in Remington's Pharmaceutical Sciences (17th edition, page 1418 (1985)).

Owing to their physical and chemical stability, and their solubility, sodium salts, potassium salts, calcium salts and ammonium salts, inter alia, are preferred for acidic groups.

The invention is not limited to α- and β-D- or L-ribofuranosides, α- and β-D- or L-deoxyribofuranosides and corresponding carbocyclic five-ring analogs, but also applies to oligonucleotide analogs which are assembled from other sugar building blocks, for example xylofuranose and arabinofuranose derivatives, ring-expanded and ring-contracted sugars, and acyclic and ring-bridged sugar derivatives or suitable sugar derivatives of a different kind. Furthermore, the invention is not limited to the derivatives of the phosphate radical which are listed by way of example in formula I, but also relates to the known dephospho derivatives.

Consequently, the novel oligonucleotides can result from modifying the natural structure in a variety of ways. Examples of such modifications, which are introduced by methods which are known per se, are:

a) Modifications of the Phosphate Bridge

The following may be mentioned by way of example: phosphorothioates, phosphorodithioates, methylphosphonates, phosphoroamidates, boranophosphates, methyl phosphates, ethyl phosphates and phenylphosphonates. Phosphorothioates, phosphorodithioates and methylphosphonates are preferred modifications of the phosphate bridge.

b) Replacement of the Phosphate Bridge

The following may be mentioned by way of example: replacement with acetamide, formacetal, 3'-thioformacetal, methylhydroxylamine, oxime, methylenedimethylhydrazo, dimethylenesulfone and silyl groups. Replacement with acetamide, formacetals and 3'-thioformacetals is preferred.

c) Modifications of the Sugar

The following may be mentioned by way of example: α-anomeric sugars, 2'-O-methylribose, 2'-O-butylribose, 2'-O-allylribose, 2'-fluoro-2'-deoxyribose, 2'-amino-2'-deoxyribose, α-arabinofuranose and carbocyclic sugar analogs. The preferred modification is that due to 2'-O-methylribose and 2'-O-n-butylribose.

d) Modifications of the Sugar and of the Phosphate Bridge

Those which may be mentioned by way of example are the peptide nucleic acids (PNA's), in which the sugar/phosphate backbone is replaced by an aminoethylglycine backbone (see German Patent Application P4408531.1), and the carbamate-bridged morpholino oligomers. The PNA's can also be linked to nucleic acids, as described in German Patent Application P4408528.1.

e) Other Modifications of the Bases, in Particular of the Pyrimidine Bases

The following may be mentioned by way of example:
5-propynyl-2'-deoxyuridine, 5-propynyl-2'-deoxycytidine, 5-hexynyl-2'-deoxyuridine, 5-hexynyl-2'-deoxycytidine, 5-fluoro-2'-deoxycytidine, 5-fluoro-2'-deoxyuridine, 5-hydroxymethyl-2'-deoxyuridine, 5-methyl-2'-deoxycytidine and 5-bromo-2'-deoxycytidine. 5-Propynyl-2'-deoxyuridine, 5-hexynyl-2'-deoxyuridine, 5-hexynyl-2'-deoxycytidine and 5-propynyl-2'-deoxycytidine are preferred modifications.

f) 3'-3' and 5'-5' Inversions [e.g. M. Koga et al., J. Org. Chem. 56 (1991) 3757]

g) 5' conjugates and 3'-conjugates.

Examples of groups which favor intracellular uptake are different lipophilic radicals, such as —O—(CH$_2$)$_x$—CH$_3$, in which x is an integer from 6 to 18, —O—(CH$_2$)$_n$—CH=CH—(CH$_2$)$_m$—CH$_3$, in which n and m are, independently of each other, an integer from 6 to 12, —O—(CH$_2$CH$_2$O)$_4$—(CH$_2$)$_9$—CH$_3$, —O—(CH$_2$CH$_2$O)$_8$—(CH$_2$)$_{13}$—CH$_3$ and —O—(CH$_2$CH$_2$O)$_7$—(CH$_2$)$_{15}$—CH$_3$, and also steroid radicals, such as cholesteryl, or vitamin radicals, such as vitamin E, vitamin A or vitamin D, and other conjugates which exploit natural carrier systems, such as bile acid, folic acid, 2-(N-alkyl, N-alkoxy)-aminoanthraquinone and conjugates of mannose and peptides of the corresponding receptors which lead to receptor-mediated endocytosis of the oligonucleotides, such as EGF (epidermal growth factor), bradykinin and PDGF (platelet derived growth factor). Labeling groups are to be understood to mean fluorescent groups, for example of dansyl (=N-dimethyl-1-aminonaphthyl-5-sulfonyl) derivatives, fluorescein derivatives or coumarin derivatives, or chemiluminescent groups, for example of acridine derivatives, and also the digoxygenin system, which is detectable by means of ELISA, the biotin group, which is detectable by means of the biotin/avidin system, or else linker arms having functional groups which permit subsequent derivatization with detectable reporter groups, for example an aminoalkyl linker which is converted into the chemiluminescence probe using an acridinium active ester. Other suitable linkers are known to a person skilled in the art from the published patent applications EP 251786 and WO 93/09217.

h) Conjugation by Way of the 7 Position and/or the 8 Position on the 7-Deazapurine Groups which serve to label a DNA or RNA probe or which favor intracellular uptake can also be conjugated by way of the 7 position and/or 8 position of the 7-deazapurine. 7-Deazapurine nucleosides to which biotin or iminobiotin radicals are conjugated by way of the 7 position of the 7-deazapurine, via a special connecting group, have been disclosed by EP 63 879.

Labeling groups for a DNA or RNA probe are to be understood to mean fluorescent groups, for example of dansyl (=N-dimethyl-1-aminonaphthyl-5-sulfonyl) derivatives, fluorescein derivatives or coumarin derivatives, or chemiluminescent groups, for example of acridine derivatives, and also the digoxygenin system, which is detectable by means of ELISA, or the biotin group, which is detectable by means of the biotin/avidin system, and also the intercalators and chemically active groups which have already been listed under g) (see, also, Beaucage et al., Tetrah. (1993) Vol. 49, No. 10, 1925–1963).

Examples of groups which favor intracellular uptake are steroid radicals, such as cholesteryl, or vitamin radicals such as vitamin E, vitamin A or vitamin D, and other conjugates which exploit natural carrier systems, such as bile acid, folic acid, 2-(N-alkyl, N-alkoxy)-aminoanthraquinone and conjugates of mannose and peptides of the corresponding receptors which lead to receptor-mediated endocytosis of the oligonucleotides, such as EGF (epidermal growth factor), bradykinin and PDGF (platelet derived growth factor).

In a general manner, the described groups can be introduced either at the level of the oligonucleotides (for example by way of SH groups) or at the level of the monomers (phosphonates, phosphoamidites or triphosphates). In the case of the monomers, in particular in the case of the triphosphates, it is advantageous to leave the Bide chains, into which a reporter group or an intercalator group is to be introduced, in the protected state, and only to eliminate the side-chain protective groups, and to react with an optionally activated derivative of the corresponding reporter group or intercalator group, after the phosphorylation.

Typical labeling groups are:

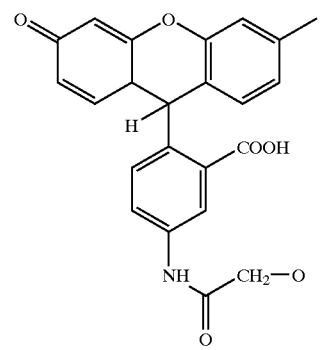

Fluorescein derivative

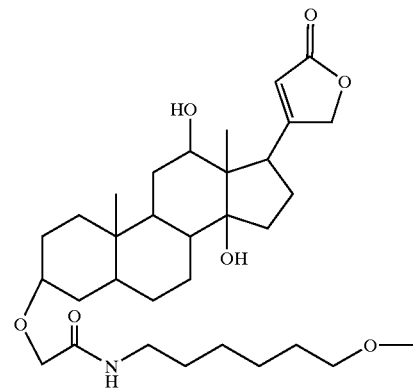

Digoxygenin conjugate

Oligonucleotide analogs which bind to nucleic acids or intercalate with them and/or cleave or cross-link them, contain, for example, acridine, psoralene, phenanthridine, naphthoquinone, daunomycin or chloroethylaminoaryl conjugates. Typical intercalating and cross-linking radicals are:

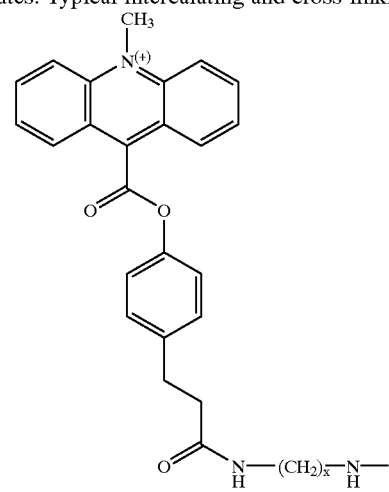

Acridinium ester

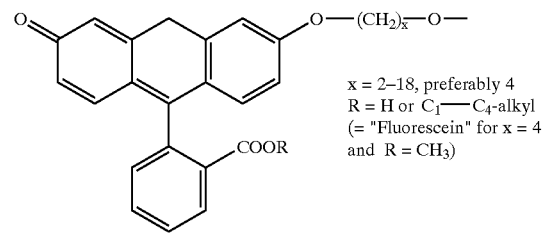

x = 2–18, preferably 4
R = H or $C_1$—$C_4$-alkyl
(= "Fluorescein" for x = 4 and R = $CH_3$)

Fluorescein derivative

R = H or amino protective group

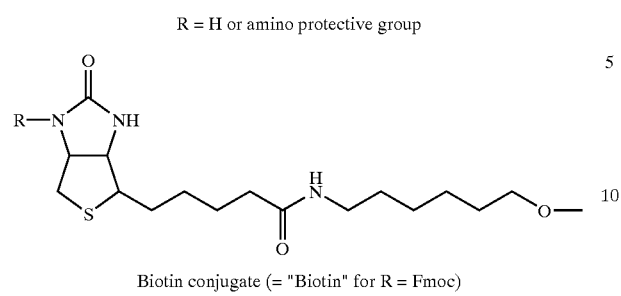

Biotin conjugate (= "Biotin" for R = Fmoc)

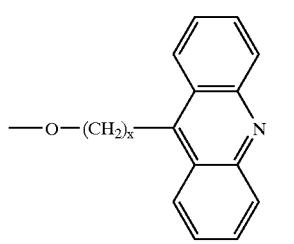

Acridine derivative x = 2–12, preferably 4

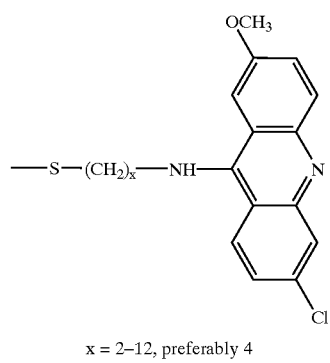

x = 2–12, preferably 4

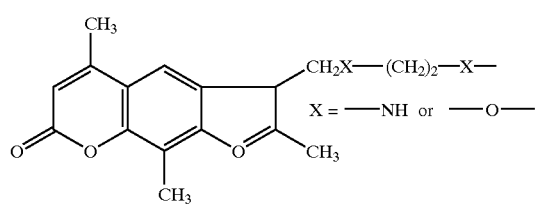

Trimethylpsoralene conjugate (= "Psoralene" for X = O)

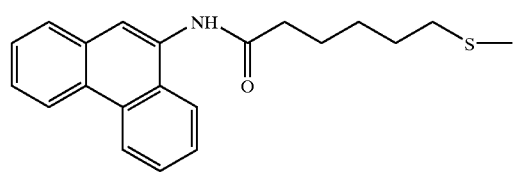

Phenanthroline conjugate

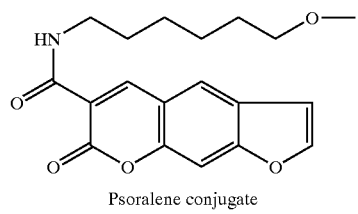

Psoralene conjugate

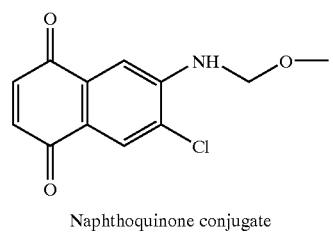

Naphthoquinone conjugate

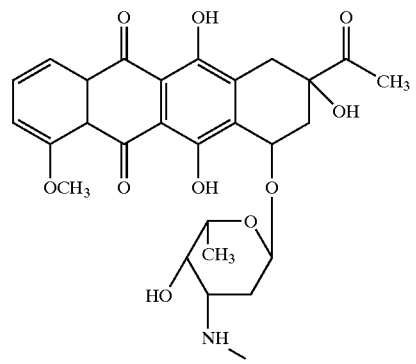

Daunomycin derivative

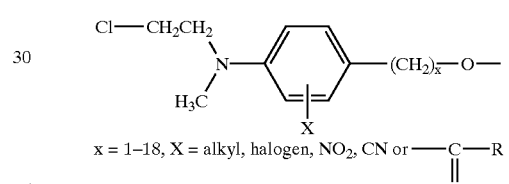

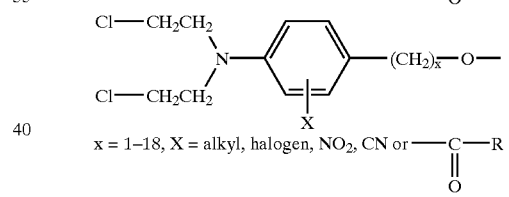

The invention furthermore relates to compounds of the formula V

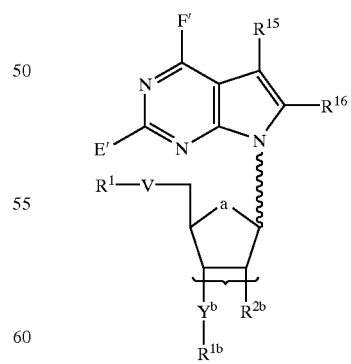

(V)

in which
V is oxy, sulfanediyl or imino;
$Y^b$ is oxy, sulfanediyl, imino or methylene;
a is oxy, sulfanediyl or methylene;

$R^{2b}$ is hydrogen, $OR^{12}$, $C_1$–$C_{18}$-alkoxy, $C_1$–$C_6$-alkenyloxy, in particular allyloxy, halogen, azido or $NR^{10}R^{11}$;

$R^1$ is a protective group which is customary in nucleotide chemistry;

$R^{1b}$ is a succinyl radical or other conventional linker for linking the oligonucleotide containing this group to a solid support e.g., an amino-functionalized or methylamino-functionalized support, by way of an amide or methylimide bond, or the like, or is a radical of the formula IIIc or IIId $$\begin{array}{c} | \\ U\text{—}P\text{—}Q \\ | \end{array} \tag{IIIc}$$

$$\begin{array}{c} | \\ O{=}P\text{—}O^{\ominus} \\ | \\ H \end{array} \tag{IIId}$$

in which

U is $(C_1$–$C_{18})$-alkoxy, $(C_1$–$C_{18})$-alkyl, $(C_6$–$C_{20})$-aryl, $(C_6$–$C_{14})$-aryl-$(C_1$–$C_8)$-alkyl, O—$R^7$, S—$R^7$ or a radical of the formula IV $$(OCH_2CH_2)_pO(CH_2)_qCH_2R^5 \tag{IV}$$

in which $R^5$ is H;

Q is a radical —$NR^8R^9$, $R^7$ is —$(CH_2)_2$—CN;

$R^8$ and $R^9$ are identical or different and are $C_1$–$C_6$-alkyl, in particular isopropyl or ethyl, or, together with the nitrogen atom carrying them, are a 5–9-membered heterocyclic ring which can additionally contain a further hetero atom from the series O, S and N, in particular

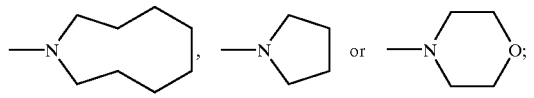

E' and F' are, independently of each other, H, $OR^{12}$ or $NR^{10}R^{11}$, $R^{10}$ and $R^{11}$ are identical or different and are hydrogen or an amino protective group which is customary in nucleotide chemistry, or $R^{10}$ and $R^{11}$ together form an amino protective group which is customary in nucleotide chemistry, $R^{12}$ is hydrogen or a hydroxyl protective group which is customary in nucleotide chemistry, such as, for example, t-butyldimethyl-silyl, dimethoxytriphenyl-methyl (DMT), triisopropyl-silyl, o-nitro-benzyl, p-nitro-benzyl, iBu, 2-fluorophenyl-4-methoxy-piperidin-4-yl (FPMP), or methyl, $R^{15}$ and $R^{16}$ are, independently of each other,
1. hydrogen,
2. halogen,
3. $(C_1$–$C_{10})$-alkyl,
4. $(C_2$–$C_{10})$-alkenyl,
5. $(C_2$–$C_{10})$-alkynyl,
6. $NO_2$,
7. $NH_2$,
8. cyano,
9. —S—$(C_1$–$C_6)$-alkyl,
10. $(C_1$–$C_6)$-alkoxy,
11. $(C_6$–$C_{20})$-aryloxy,
12. $SiH_3$, 13. 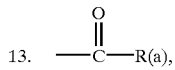

14. a radical as defined under 3., 4. or 5. which is substituted by one or more radicals from the group SH, S—$(C_1$–$C_6)$-alkyl, $(C_1$–$C_6)$-alkoxy, OH, —NR(c)R(d), —CO—R(b), —NH—CO—NR(c)R(d), —NR(c)R(g), —NR(e)R(f) or —NR(e)R(g), or by a polyalkyleneglycol radical of the formula —[O—$(CH_2)_r$]$_s$—NR(c)R(d), where r and s are, independently of each other, an integer between 1 and 18, preferably 1 and 6, with it being possible for functional groups such as OH, SH, —CO—R(b), —NH—CO—NR(c)R(d), —NR(c)R(d), —NR(e)R(f), —NR(e)R(g) or —NR(c)R(g) to carry a protective group which is customary in nucleotide chemistry or to be linked, where appropriate via a further linker, to one or more groups which favor intracellular uptake or serve as labeling for a DNA or RNA probe or, when the oligonucleotide analog hybridizes to the target nucleic acid, attack the latter while binding, cross-linking or cleaving, or 15. a radical as defined under 3., 4. or 5. in which from one to all the H atoms are substituted by halogen, preferably fluorine.

R(a) is OH, $(C_1$–$C_6)$-alkoxy, $(C_6$–$C_{20})$-aryloxy, $NH_2$ or NH-T, where T is an alkylcarboxyl group or alkylamino group which is linked, optionally via a further linker, to one or more groups which favor intracellular uptake, or serve as labeling for a DNA or RNA probe or, when the oligonucleotide analog hybridizes to the target nucleic acid, attack the latter while binding, cross-linking or cleaving, R(b) is hydroxyl, $(C_1$–$C_6)$-alkoxy or —NR(c)R(d), R(c) and R(d) are, independently of each other, H or $(C_1$–$C_6)$-alkyl which is unsubstituted or substituted by —NR(e)R(f) or —NR(e)R(g), R(e) and R(f) are, independently of, each other, H or $(C_1$–$C_6)$-alkyl, R(g) is $(C_1$–$C_6)$-alkyl-COOH, with the proviso that $R^{15}$ and $R^{16}$ cannot each simultaneously be hydrogen, $NO_2$, $NH_2$, cyano or $SiH_3$, with functional groups such as OH, $NH_2$ or COOH being protected, where appropriate, with a protective group which is customary in nucleotide chemistry, and the curved bracket indicating that $R^{2b}$ and the adjacent —$Y^b$—$R^{1b}$ radical can be located in the 2' and 3' positions or else, conversely, in the 3' and 2' positions.

A preferred embodiment is represented by compounds of the formula (V) in which V, $Y^b$ and a are oxy, $R^{2b}$ is hydrogen or $OR^{12}$, in particular hydrogen, and $R^{1b}$ is a radical of the formula (IIIc) or (IIId), with U being an O—$(CH_2)_2$—CN, and $R^8$ and $R^9$ being identical or, different and being isopropyl or ethyl, or, together with the N atom carrying them, being an aliphatic heterocycle, preferably pyrrolidino. These compounds are very particularly preferred if, in addition, the base is located in the β position on the sugar and $R^{2b}$ is located in the 2' position.

Compounds of formula (V) are also preferred in which E is $NR^{10}R^{11}$ and F is H, and, quite generally, those compounds of the formula (V) are preferred which can be employed for preparing preferred oligonucleotides of the formula I.

Examples of preferred amino protective groups are acyl or amidine protective groups.

The radical of the formula (IIId) which is customarily present as a salt is to be understood to mean inorganic or organic salts, for example alkali metal, alkaline earth metal or ammonium salts, which are described, for example, in Remington's Pharmaceutical Sciences (17th edition, page 1418 (1985)). Triethylammonium and pyridinium salts may be mentioned by way of example. However, the invention also embraces compounds of the formula (V) in which the radical of the formula (IIId) is present as a free acid.

The compounds of the formula V may be employed as structural components for preparing the novel oligonucleotides of the formula I.

EP 251 786 discloses 7-deazapurine nucleotides, and their monophosphates, diphosphates or triphosphates, which possess an alkynylamino group at the 7-purine position. The alkynylamino group serves as a linker by way of which fluorescent labeling molecules can be coupled to the nucleotide. The dideoxynucleotides which have been provided with a fluorescence label can then be used as chain terminator molecules for dideoxy sequencing in accordance with Sanger and detected directly by means of fluorescence spectroscopy. U.S. Pat. No. 5,241,060 discloses 7-deazapurine nucleotides which carry a detectable radical on the 7-deazapurine.

The invention also relates to compounds of the formula VI

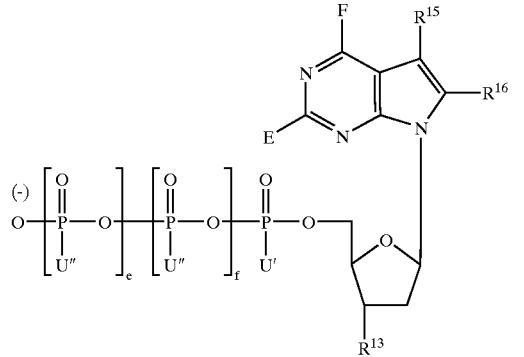

(VI)

in which, independently of each other,

U'=U"=U'" is hydroxyl or mercapto, and U' can additionally be $BH_3$, e and f are 0 or 1;

$R^{13}$ is hydrogen, OH, $C_1$–$C_{18}$-alkoxy, or $C_1$–$C_{16}$-alkenyloxy, in particular allyloxy;

E and F are, independently of each other, H, OH or $NH_2$; and $R^{15}$ and $R^{16}$ are, independently of each other,
1. hydrogen,
2. halogen,
3. ($C_1$–$C_{10}$)-alkyl,
4. ($C_2$–$C_{10}$)-alkenyl,
5. ($C_2$–$C_{10}$)-alkynyl,
6. $NO_2$,
7. $NH_2$,
8. cyano,
9. —S—($C_1$–$C_6$)-alkyl,
10. ($C_1$–$C_6$)-alkoxy,
11. ($C_6$–$C_{20}$)-aryloxy,
12. $SiH_3$, 13. 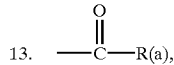

14. a radical as defined under 3., 4. or 5. which is substituted by one or more radicals from the group SH, S—($C_1$–$C_6$)-alkyl, ($C_1$–$C_6$)-alkoxy, OH, —NR(c)R(d), —CO—R(b), —NH—CO—NR(c)R(d), —NR(c)R(g), —NR(e)R(f) or —NR(e)R(g), or by a polyalkyleneglycol radical of the formula —[O—$(CH_2)_r$]$_s$—NR(c)R(d), where r and s are, independently of each other, an integer between 1 and 18, preferably 1 and 6, with it being possible for functional groups such as OH, SH, —CO—R(b), —NH—CO—NR(c)R(d), —NR(c)R(d), —NR(e)R(f), —NR(e)R(g) or —NR(c)R(g) additionally to be linked, where appropriate via a further linker, to one or more groups which favor intracellular uptake or serve as labeling for a DNA or RNA probe or, when the oligonucleotide analog hybridizes to the target nucleic acid, attack the latter while binding, cross-linking or cleaving, or
15. a radical as defined under 3., 4. or 5. in which from one to all the H atoms are substituted by halogen, preferably fluorine.

R(a) is OH, ($C_1$–$C_6$)-alkoxy, ($C_6$–$C_{20}$)-aryloxy, $NH_2$ or NH-T, with T representing an alkylcarboxyl or alkylamino group which is linked, where appropriate via a further linker, to one or more groups which favor intracellular uptake or serve as labeling for a DNA or RNA probe or, when the oligonucleotide analog hybridizes to the target nucleic acid, attack the latter while binding, cross-linking or cleaving, R(b) is hydroxyl, ($C_1$–$C_6$)-alkoxy or —NR(c)R(d), R(c) and R(d) are, independently of each other, H or ($C_1$–$C_6$)-alkyl which is unsubstituted or substituted by —NR(e)R(f) or —NR(e)R(g), R(e) and R(f) are, independently of each other, H or ($C_1$–$C_6$)-alkyl, R(g) is ($C_1$–$C_6$)-alkyl-COOH, with the proviso that $R^{15}$ and $R^{16}$ cannot each simultaneously be hydrogen, $NO_2$, $NH_2$, cyano or $SiH_3$, with compounds of the formula VI being excepted in which $R^{16}$ is H and $R^{15}$ is ($C_2$–$C_{10}$)-alkynyl which is substituted by —NR(c)R(d) or —NR(e)R(f); and with the additional proviso that e and f are not 0 if E is OH or $NH_2$ and F is OH, $R^{16}$ is hydrogen and $R^{15}$ is Br, Cl, F, cyano, ($C_1$–$C_4$)-alkyl, ($C_2$–$C_4$)-alkenyl or ($C_2$–$C_4$)-alkynyl.

The invention also embraces compounds of the formula VI which are provided, in a generally customary manner, with a radioactive label (for example, αP atom is $^{32}$P; U' is $^{35}$S).

Compounds of the formula VI are preferred in which U' is hydroxyl or mercapto, U"=U'". is hydroxyl, and e and/or f is 1. Compounds of the formula VI are particularly preferred when e and f are 1.

The compounds of the formula VI which are customarily present as a salt comprise inorganic or organic salts, for example alkali metal, alkaline earth metal or ammonium salts [Remington's Pharmaceutical Sciences (17th edition, page 1418 (1985)]. Triethylammonium and pyridinium salts may be mentioned by way of example. The novel VI compounds also comprise those compounds in which the phosphate group is present as a free acid.

The novel compounds of the formula VI may be employed generally as aids in molecular biology, for example in PCR reactions (e=f=1, $R^{13}$=OH) or for sequencing (e=f=1; $R^{13}$=H or OH). In PCR-reactions compounds of the formula VI are preferred in which $R^{16}$ is H and $R^{15}$ is halogen. Amplification of longer nucleodide sequences is enhanced using the modified oligonucleotides.

The use of the novel 7-deazapurine nucleotides for sequencing nucleic acids is advantageous for several reasons. Thus, the band compression which can often be observed in GC-rich nucleotide regions in the Sanger sequencing method (dideoxy technique), and which hinders correct determination of the nucleotide sequence, is either eliminated or at least reduced. In addition, the double-stranded nucleic acids which are synthesized by DNA polymerases or RNA polymerases during the sequencing are stabilized by the incorporation of 7-, 8- or 7,8-substituted 7-deazapurine bases. It is consequently more advantageous to use substituted 7-deazapurine nucleotides than to use unsubstituted 7-deazaguanosine nucleotides, which are customarily employed in nucleic acid sequencing in order to eliminate band compressions in GC-rich DNA stretches (EP 212536). A further advantage of using substituted 7-deazapurine nucleotides in the sequencing is that fluorescent residues in the form of reporter groups, which make possible fluorescence-spectroscopic detection of the nucleic acid molecules which are synthesized during the sequencing reaction, can be introduced onto the substituents in a series of subsequent reactions.

In addition, the incorporation of self-fluorescent, substituted 7-deazapurine bases into oligonucleotides renders it possible to detect the latter directly by way of the self-fluorescence of the substituted 7-deazapurine bases. Thus, the 7-deazapurine bases, which in unsubstituted form are not fluorescent, become fluorescent, for example, when an alkynyl group, for example hexynyl, is introduced at the 7 position. The self-fluorescence of these compounds can be measured at 350 nm (emission) following excitation with light of 280 nm wavelength.

The compounds of the formula VI can be prepared by proceeding from the corresponding substituted 7-deazapurine nucleosides and using well known methods. The compounds of the formula VI can preferably be prepared by an abbreviated one-pot method due to Ludwig, in the presence of 1,8-bis(dimethylamino)naphthalene and trimethyl phosphate [J. Ludwig et al., (1981) Acta Biochem. Biophys. Sci. Hung., 16, 131].

The invention also relates to compounds of the formula VII

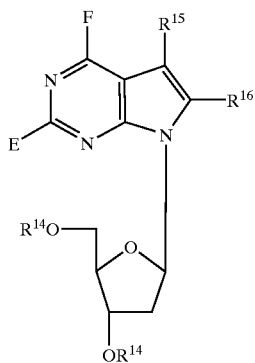

(VII)

in which

E and F are, independently of each other, H, OH or $NH_2$, and OH and $NH_2$ are, where appropriate, protected by a protective group which is customary in nucleotide chemistry;

$R^{15}$ and $R^{16}$ are, independently of each other, hydrogen, $(C_1-C_{10})$-alkyl, $(C_2-C_{10})$-alkenyl, $(C_2-C_{10})$-alkynyl, I, Cl, Br, F, cyano, or $(C_1-C_{10})$-alkyl, $(C_2-C_{10})$-alkenyl or $(C_2-C_{10})$-alkynyl in which from one to all the H atoms are substituted by halogen, preferably fluorine, with it not being possible for $R^{15}$ and $R^{16}$ to be simultaneously hydrogen and cyano, and with the further proviso that $R^{15}$ is not I if $R^{16}$ is hydrogen, E is $NH_2$ and F is OH, $R^{14}$ are, independently of each other, H or a protective group which is customary in nucleotide chemistry.

The invention also embraces all the tautomeric forms of the compounds of the formulae I, V, VI and VII, and, in particular, all the tautomeric forms of the 7-deazapurine bases of the formula II.

In a quite general manner, those compounds of the formulae V, VI and VII are also preferred which can be used as starting compounds or intermediates for the preparation of preferred oligonucleotides of the formula I.

The invention furthermore relates to a process for preparing the novel oligonucleotides of the formula I. The standard conditions which are customary in the chemical synthesis of oligonucleotides can be applied for preparing the novel oligonucleotides containing substituted 7-deazapurine.

The novel oligonucleotides of the formula I are prepared in solution or, preferably, on a solid phase, where appropriate using an automatic synthesis device. The oligomers of the formula I can be assembled stepwise by successively condensing a mononucleotide, which in each case possesses a nucleotide base, onto an appropriately derivatized support or onto a growing oligomer chain. Alternatively, the oligonucleotides of the formula I can be assembled by joining dinucleotides or trinucleotides together [S. Beaucage et al., Tetrah. vol. 48, No. 12, 2223–2311, (1992); and Tetrah. vol. 48, No. 28, 6123–6194, (1993)]. This is particularly advantageous when synthesizing oligonucleotides which possess modified phosphate bridges.

The oligonucleotides are assembled using methods which are known to the person skilled in the art, such as the triester method, the H-phosphonate method or the phosphoramidite method [E. Sonveaux, (1986), Bioorganic Chemistry, 14, 274–325; S. L. Beaucage et al., (1992), Tetrahedron, 48, 2223–2311]. The nucleotide monomer structural components of the formula V, particularly preferably those of the formula V in which E' is $NR^{10}R^{11}$ and F' is $OR^{12}$, or F' is $NR^{10}NR^{11}$ and E' is H, are preferably employed for introducing the 7-deazapurine derivatives.

The compounds of the formula V can be prepared, as structural components for the oligonucleotide solid phase synthesis, by proceeding from the corresponding 7-deazapurine nucleosides. Substituents can be introduced at the 7 position of the 7-deazapurine ring system using well-known methods. For example, the preparation of 7-deazapurine nucleosides which are substituted at the 7 position by halogen or methyl is described by Seela et al. [Helvetica Chimica Acta, (1994) 77, 897–903]. Alkenyl- or alkynyl-substituted 7-deazapurine derivatives of the formula V can be prepared by proceeding from the known 5-iodotubercidin (=7-I-7-deazaadenosine, see Seela et al., above), and coupling alkenyl or alkynyl groups onto the 7 position of the 7-deazapurine ring system by means of a cross-coupling reaction in the presence of tetrakis (triphenylphosphine)palladium(O). Electrophilic substituents (for example halogens) can be introduced into the 8 position of the 7-deazapurine ring system if nucleosides are employed as starting compounds which possess an electronsupplying substituent (for example an amino group) at the 2 position of the 7-deazapurine. If the 2-amino group is, for example, acetylated, the electrophilic substituent is then directed into the 7 position. Consequently, the present invention also relates to a process for the regioselective insertion of electrophilic substituents (for example halogens) into the 7 or 8 position of 7-deazanucleosides. The halogenated nucleosides can then be used as starting compounds for the insertion of other substituents, for example alkyl, alkenyl or alkynyl groups, by means of the above-described palladium-catalyzed cross-coupling reaction. Alkoxy derivatives or substituted amine derivatives can be introduced by nucleophilic substitution, and nitro groups can be introduced by electrophilic substitution.

After suitable protective groups for the amino groups of the 7-deazapurine bases and for the free 5'-hydroxyl group of the sugar have been introduced, the monomers are converted into the corresponding phosphonate or phosphoramidite derivatives. Suitable amino protective groups, for example in the form of a formamidine protective group ((dimethylamino)methylidene) or acyl protective groups (e.g. benzoyl or phenoxyacetyl), are inserted using well-known methods [L. J. McBride et al., (1983) Tetrahedron Lett., 24, 2953, G. S. Ti et al., (1982) J. Am. Chem. Soc., 104, 1316; H. Schaller et al. (1963), J. Am. Chem. Soc., 85, 3821], with it being advantageous, when the amino group is acylated, to use the Schaller peracylation method. An example of a suitable protective group for the free 5'-OH group of the sugar is 4,4'-dimethoxytrityl, whose insertion is likewise effected using known methods [C. B. Reese (1978), Tetrahedron, 34, 3143; D. Flockerzi et al., (1981), Liebigs Ann. Chem., 1568]. The monomers which have been protected in this way can be converted into the corresponding phosphonates in accordance with a protocol due to Froehler et al. [B. C. Froehler et al., (1986), Nucl. Acid Res., 14, 5399]. Cyanoethyl-phosphoramidite derivatives can, for example, be prepared by reacting the monomers with chloro-β-cyanoethoxy-(N,N-diisopropylamino)phosphane in anhydrous dichloromethane [N.D. Sinha et al., (1984) Nucl. Acid Res., 12, 4539].

Compounds of the formula I whose oligonucleotide moiety is modified at the 3' end and/or the 5' end are synthesized, as regards these modifications, using the methods described in EP-A 0 552 766.

For use according to the invention, the oligonucleotides have a length of from 4 to 100, preferably of about 5–40, in particular of about 6–30, nucleotides. Otherwise, the above-described preference ranges, modifications and conjugations also apply in this case too.

The present invention relates to the use of oligonucleotides containing at least one substituted 7-deazapurine, preferably 7-deazaadenine or 7-deazaguanine, as a diagnostic reagent, for example for detecting the presence or absence of, or the quantity of, a specific double-stranded or single-stranded nucleic acid molecule in a biological sample. One or more of these oligonucleotides maybe directly or indirectly bound or absorbed onto a solid support, or provided as a solution in a solvent or diluent, optionally together with other conventional diagnostically relevant auxiliary reagents.

The invention furthermore relates to pharmaceutical compositions comprising one or more oligonucleotides of the formula I, together with a physiologically acceptable excipient and, where appropriate, suitable additives and/or conventional auxiliary substances.

In a quite general manner, the present invention extends to the use of oligonucleotides of the formula —I in therapeutically effective amounts in improved therapeutic methods. In general, therapeutically effective oligonucleotide derivatives are understood to mean antisense oligonucleotides, triple helix-forming oligonucleotides, aptamers or ribozymes, in particular antisense oligonucleotides.

The pharmaceuticals of the present invention can, for example, be used to treat diseases which are caused by viruses, for example by HIV, HSV-1, HSV-2, influenza, VSV, hepatitis B or papilloma viruses.

Novel antisense oligonucleotide derivatives, that is antisense oligonucleotides in which at least one purine base is replaced by a substituted 7-deazapurine base, and which are effective against these targets, have, for example, the following base sequences:

a) Against HIV, e.g.

(SEQ ID NO.: 1)
5'-A C A C C C A A T T C T G A A A A T G G-3' or (SEQ ID NO.: 2)
5'-A G G T C C C T G T T C G G G C G C C A-3' or (SEQ ID NO.: 3)
5'-G T C G A C A C C C A A T T C T G A A A A T G G
A T A A-3' or (SEQ ID NO.: 4)
5'-G C T A T G T C G A C A C C C A A T T C T G A A
A-3' or (SEQ ID NO.: 5)
5'-T C G T C G C T G T C T C C G C T T C T T C T T
C C T G C C A-3' or

The pharmaceuticals of the present invention are also suitable, for example, for treating cancer. For example, oligonucleotide sequences can be used in this context which are directed against targets which are responsible for the occurrence of cancer or for cancer growth. Examples of such targets are:

1) nuclear oncoproteins such as, for example, c-myc, N-myc, c-myb, c-fos, c-fos/jun, PCNA and p120,
2) cytoplasmic/membrane-associated oncoproteins such as, for example, EJ-ras, c-Ha-ras, N-ras, rrg, bcl-2, cdc-2, c-raf-1, c-mos, c-src and c-abl,
3) cellular receptors, such as, for example, the EGF receptor, c-erbA, retinoid receptors, the protein kinase regulatory subunit and c-fms,
4) cytokines, growth factors, and extracellular matrix, such as, for example, CSF-1, IL-6, IL-1a, IL-1b, IL-2, IL-4, bFGF, myeloblastin and fibronectin.

Novel antisense oligonucleotides of the formula I which are effective against these targets have, for example, the following base sequences:

a) Against c-Ha-ras, e.g.

5'-CAGCTGCAACCCAGC-3' (SEQ ID NO.:7)

c) c-myc, e.g.

(SEQ ID NO.: 8)
5'-G G C T G C T G G A G C G G G G C A C A C-3'

(SEQ ID NO.: 9)
5'-A A C G T T G A G G G G C A T-3' d) c-myb, e.g.

5'-GTGCCGGGGTCTTCGGGC-3' (SEQ ID NO.: 10)

e) c-fos, e.g.

5'-G G A G A A C A T C A T G G T C G A A A G-3' (SEQ ID NO.: 11)

5'-C C C G A G A A C A T C A T G G T C G A A G-3' (SEQ ID NO.: 12)

5'-G G G G A A A G C C C G G C A A C G G G-3' (SEQ ID NO.: 13)

f) p120, e.g.
5'-CACCCGCCTTGGCCTCCCAC-3' (SEQ ID NO.: 14)
g) EGF Receptor, e.g.

5'-G G G A C T C C G G C G C A G C G C-3' (SEQ ID NO.: 15)

5'-G G C A A A C T T T C T T T T C C T C C-3' (SEQ ID NO.: 16)

h) p53 Tumor Suppressor, e.g.

5'-G G G A A G G A G G A G G A T G A G G-3' (SEQ ID NO.: 17)

5'-G G C A G T C A T C C A G C T T C G G A G-3' (SEQ ID NO.: 18)

The pharmaceuticals of the present invention are furthermore suitable, for example, for treating diseases which are affected by integrins or cell-cell adhesion receptors, for example by VLA-4, VLA-2, ICAM, VCAM or ELAM.

Novel antisense oligonucleotide derivatives which are effective against these targets have, for example, the following base sequences:
a) VLA-4, e.g.
5'-GCAGTAAGCATCCATATC-3' (SEQ ID NO.: 19)
b) ICAM, e.g.

5'-C C C C C A C C A C T T C C C C T C T C-3' (SEQ ID NO.: 20)

5'-C T C C C C C A C C A C T T C C C C T C-3' (SEQ ID NO.: 21)

5'-G C T G G G A G C C A T A G C G A G G-3' (SEQ ID NO.: 22)

c) ELAM-1, e.g.

5'-A C T G C T G C C T C T T G T C T C A G G-3' (SEQ ID NO.: 23)

5'-C A A T C A A T G A C T T C A A G A G T T C-3' (SEQ ID NO.: 24)

The pharmaceuticals of the present invention are also suitable, for example, for preventing restenosis. For example, oligonucleotide sequences can be used in this context which are directed against targets which are responsible for proliferation or migration. Examples of these targets are:
1) Nuclear transactivator proteins and cyclins, such as, for example, c-myc, c-myb, c-fos, c-fos/jun, cyclins and cdc2 kinase
2) Mitogens or growth factors, such as, for example, PDGF, bFGF, EGF, HB-EGF and TGF-β.
3) Cellular receptors such as, for example, bFGF receptor, EGF receptor and PDGF receptor.

Novel oligonucleotides of the formula I which are effective against these targets have, for example, the following base sequences:

a) c-myb
5'-GTGTCGGGGTCTCCGGGC-3' (SEQ ID NO.: 25)
b) c-myc
5'-CACGTTGAGGGGCAT-3' (SEQ ID NO.: 26)
c) cdc2 kinase
5'-GTCTTCCATAGTTACTCA-3' (SEQ ID NO.: 27)
d) PCNA (proliferating cell nuclear antigen of rat)
5'-GATCAGGCGTGCCTCAAA-3' (SEQ ID NO.:28)

The pharmaceuticals can be used, for example, in the form of pharmaceutical preparations which can be administered orally, for example in the form of tablets, coated tablets, hard or soft gelatin capsules, solutions, emulsions or suspensions. The inclusion of the pharmaceuticals in liposomes, which, where appropriate, contain additional components such as proteins, likewise represents a suitable administration form. They can also be administered rectally, for example in the form of suppositories, or parenterally, for example in the form of injection solutions. For the production of pharmaceutical preparations, these compounds can be processed in therapeutically inert, organic and inorganic excipients. Examples of such excipients for tablets, coated tablets and hard gelatin capsules are lactose, corn starch, or derivatives thereof, tallow and stearic acid, or salts thereof. Suitable excipients for preparing solutions are water, polyols, sucrose, invert sugar and glucose. Suitable excipients for injection solutions are water, alcohols, polyols, glycerol and vegetable oils. Suitable excipients for suppositories are vegetable and hardened oils, waxes, fats and semiliquid polyols. The pharmaceutical preparations can also contain preservatives, solvents, stabilizers, wetting agents, emulsifiers, sweeteners, colorants, flavorants, salts for altering the osmotic pressure, buffers, coating agents, antioxidants and other therapeutical active compounds, where appropriate.

Preferred forms of administration are topical administrations, local administrations, such as, for example, using a catheter, or else injections. For injection, the antisense oligonucleotide derivatives are formulated in a liquid solution, preferably in a physiologically acceptable buffer, such as, e.g., Hank's solution or Ringer's solution. However, the antisense oligonucleotides can also be formulated in solid form and dissolved or suspended prior to use. The doses which are preferred for systemic administration amount to from about 0.01 mg/kg to about 50 mg/kg of body weight and per day.

In a quite general manner, the invention extends to the use of compounds of the formula I as DNA probes or primers in DNA diagnostics and, in a general manner, as aids in molecular biology, as noted earlier.

Individual DNA molecules can be visualized electron microscopically, for example in a scanning-tunneling microscope. While pyrimidine bases can be differentiated electronmicroscopically due to the methyl group at the 5 position, this is not possible in the case of the purine bases adenine and guanine. It is not possible, therefore, to decode the base sequences of nucleic acid molecules electronmicroscopically in a straightforward manner. However, if the nucleic acid molecule to be investigated now contain substituted 7-deazaguanine derivatives, for example, in place of the unmodified guanine bases, the substituted 7-deazaguanine bases can be distinguished in the electron microscope from unsubstituted adenine bases (and, conversely, guanine bases can be distinguished from substituted 7-deazaadenine bases). Consequently, the base sequences of nucleic acids which contain 7-substituted 7-deazapurine bases can be decoded by electron microscopy.

EXAMPLES
The compounds (1)–(25) named in the examples exhibit the following structural formulae.
| | R |
|---|---|
| (1) | Cl |
| (2) | Br |
| (3) | CH$_3$ |
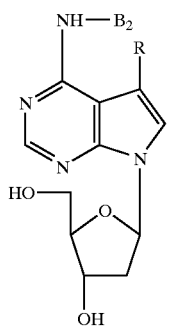
| | R |
|---|---|
| (4) | Cl |
| (5) | Br |
| (6) | CH$_3$ |
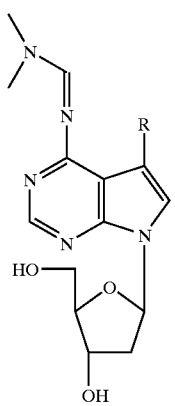
| | R |
|---|---|
| (7) | Br |
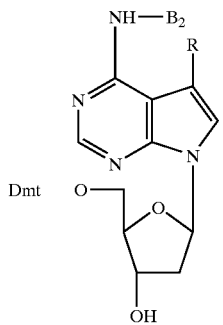
| | R |
|---|---|
| (8) | Cl |
| (9) | Br |
| (10) | CH$_3$ |
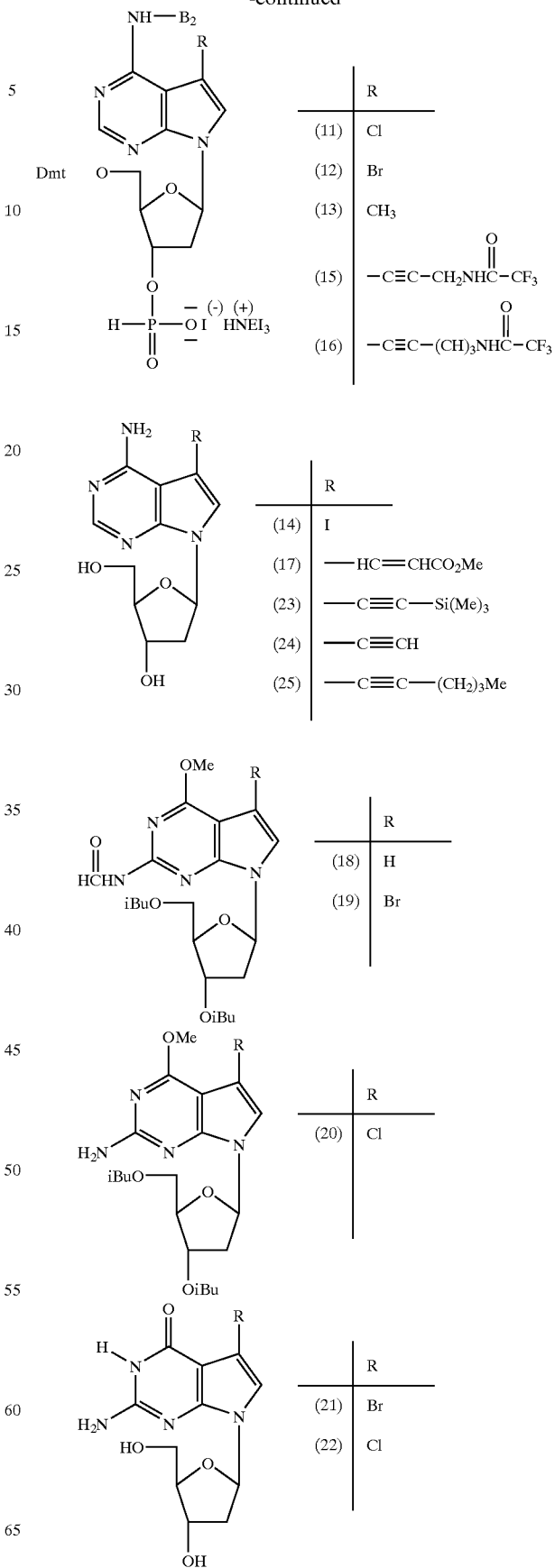
| | R |
|---|---|
| (11) | Cl |
| (12) | Br |
| (13) | CH$_3$ |
| (15) | —C≡C—CH$_2$NHC(O)—CF$_3$ |
| (16) | —C≡C—(CH)$_3$NHC(O)—CF$_3$ |
| | R |
|---|---|
| (14) | I |
| (17) | —HC=CHCO$_2$Me |
| (23) | —C≡C—Si(Me)$_3$ |
| (24) | —C≡CH |
| (25) | —C≡C—(CH$_2$)$_3$Me |
| | R |
|---|---|
| (18) | H |
| (19) | Br |
| | R |
|---|---|
| (20) | Cl |
| | R |
|---|---|
| (21) | Br |
| (22) | Cl |

The deoxytubercidin derivatives (1)–(3) (tubercidin=7-deazaadenosine) are prepared using the method described by Seela et al. [Helvetica Chimica Acta, 1994, 77, 897–903)].

The corresponding ribonucleoside derivatives can be prepared in analogy with the following examples using a tubercidin derivative as the starting compound.

Example 1

4-Benzoylamino-5-chloro-7-(2-deoxy-β-D-erythropentofuranosyl)-7H-pyrrolo[2,3-d]pyrimidine (4)

1.14 g (4.0 mmol) of 5-chlorodeoxytubercidin (1) are evaporated twice with dry pyridine and dissolved in 10 ml of dry pyridine, and this solution is then stirred, at room temperature for 2 h, together with 5.2 ml (40.6 mmol) of trimethylchlorosilane. 520 μl (4.1 mmol) of freshly distilled benzoyl chloride are then added, and the mixture is stirred at room temperature for a further 2 h. 4 ml of water and, after a further 5 min, 8 ml of 25% aqueous ammonia are added dropwise while cooling with ice. The mixture is stirred at room temperature for 30 min and then evaporated to dryness. The residue is taken up in 20 ml of water, and this solution is extracted three times with 30 ml of ethyl acetate on each occasion. The organic phases are dried over $Na_2SO_4$ and evaporated, and the residue is chromatographed on silica gel (20×5 cm column, dichloromethane/methanol 9:1). 930 mg (2.4 mmol, 60%) of the compound (4) are obtained, as colorless crystals, from the more slowly migrating main fraction after evaporating the solvent and recrystallizing the residue from methanol/water: m.p. 190° C. TLC (silica gel, dichloromethane/methanol 9:1): $R_f$=0.4. UV (MeOH): $\lambda_{max}$=274 nm (5300), 305 nm (5600).

$^1$H-NMR ([$D_6$]DMSO): δ=2.31 (m, 2'α-H), 2.57 (m, 2'β-H), 3.58 (m, 2H, 5'-H), 3.89 (m, 4'-H), 4.41 (m, 3'-H), 5.00 (t, J=5.0 Hz, 5'-OH), 5.33 (d, J=5.3 Hz, 3'-OH), 6.72 (pt, J=6.75 Hz, 1'-H), 7.44–7.65 (m, 3H, meta- and para-$H_{Bz}$), 8.00 (s, 6-H), 8.05 (d, 2H, ortho-$H_{Bz}$), 8.72 (s, 2-H), 11.2 (br, 4-NH).

| $C_{18}H_{17}ClN_4O_4$ (388.8) | Calc. | C 55.61 | H 4.41 | N 14.41 |
|---|---|---|---|---|
| | Found | C 55.71 | H 4.54 | N 14.30 |

Example 2

4-Benzoylamino-5-bromo-7-(2-deoxy-β-D-erythropentofuranosyl)-7H-pyrrolo[2,3-d]pyrimidine (5)

1.31 g (4.0 mmol) of 5-bromodeoxytubercidin (2) are evaporated twice with dry pyridine and dissolved in 10 ml of dry pyridine, and this solution is then stirred, at room temperature for 2 h, together with 5.2 ml (40.6 mmol) of trimethylchlorosilane. 520 μl (4.1 mmol) of freshly distilled benzoyl chloride are then added and the mixture is stirred at room temperature for a further 2 h. 4 ml of water and, after a further 5 min, 8 ml of 25% aqueous ammonia are added dropwise while cooling with ice. The mixture is stirred at room temperature for 30 min and then worked up in analogy with compound 14b. 1.2 g (2.8 mmol, 70%) of colorless crystals, of m.p. 198° C., are obtained after chromatography on silica gel (20×5 cm column, dichloromethane/methanol 9:1), evaporation of the solvent and recrystallization from methanol/water.

TLC (silica gel, dichloromethane/methanol 9:1): $R_f$=0.4. UV (MeOH): $\lambda_{max}$=276 nm (4600), 308 nm (4500).

$^1$H-NMR ([$D_6$] DMSO): δ=2.27 (m, 2'α-H), 2.50 (m, 2'β-H, overlapped by DMSO), 3.56 (m, 2H, 5'-H), 3.86 (m, 4'-H), 4.38 (m, 3'-H), 5.01 (t, J=5.0 Hz, 5'-OH), 5.34 (d, J=5.3 Hz, 3'-OH), 6.69 (pt, J=6.7 Hz, 1'-H), 7.52–7.64 (m, 3H, meta- and para-$H_{Bz}$)., 8.04 (d, 2H, ortho-$H_{Bz}$), 8.04 (s, 6-H), 8.72 (s, 2-H), 11.0 (br, 4-NH).

| $C_{18}H_{17}BrN_4O_4$ (433.3) | Calc. | C 49.90 | H 3.96 | N 12.93 |
|---|---|---|---|---|
| | Found | C 50.04 | H 4.10 | N 13.05 |

Example 3

4-Benzoylamino-7-(2-deoxy-β-D-erythropentofuranosyl)-5-methyl-7H-pyrrolo[2,3-d]pyrimidine (6)

1.06 g (4.0 mmol) of 5-methyldeoxytubercidin (3) are reevaporated twice with 20 ml of absolute pyridine on each occasion and dissolved in 10 ml of dry pyridine, and this solution is stirred, at room temperature, for 2 h, together with 5.2 ml (40.6 mmol) of trimethylchlorosilane.

520 μl (4.1 mmol) of freshly distilled benzoyl chloride are then added, and the mixture is stirred at room temperature for a further 2 h. The working-up is carried out in analogy to that for compound (4), and chromatography then takes place on silica gel (20×5 cm column, dichloromethane/methanol 9:1). 1.1 g (2.9 mmol, 73%) of colorless crystals (compound 6), with a m.p. of 196° C., are obtained from the more slowly migrating main fraction after evaporating the solvent and recrystallizing from methanol/water.

TLC (silica gel, dichloromethane/methanol 9:1): $R_f$=0.3. UV (MeOH): $\lambda_{max}$=274 nm (7050), 309 nm (5500).

$^1$H-NMR ([$D_6$] DMSO): δ=2.09 (m, 2'α-H), 2.21 (s, 5-$CH_3$), 2.50 (m, 2'β-H, overlapped by DMSO), 3.53 (m, 2H, 5'-H), 3.83 (m, 4'-H), 4.36 (m, 3'-H), 4.97 (t, J=5.0 Hz, 5'-OH), 5.32 (d, J=5.3 Hz, 3'-OH), 6.65 (pt, J=6.7 Hz, 1'-H), 7.53 (s, 6-H), 7.53–7.66 (m, 3H, meta- and para-$H_{Bz}$), 8.05 (d, 2H, ortho-$H_{Bz}$), 8.60 (s, 2-H), 10.95 (br, 4-NH).

| $C_{19}H_{20}N_4O_4$ (368.4) | Calc. | C 61.95 | H 5.47 | N 15.21 |
|---|---|---|---|---|
| | Found | C 62.08 | H 5.65 | N 15.00 |

Example 4

5-Bromo-4-((1-dimethylamino)methylenelamino-7-(2-deoxy-β-D-erythropentofuranosyl)-7H-pyrrolo[2,3-d]pyrimidine (7)

1.5 ml (8.75 mmol) of N,N-dimethylformamide diethyl acetal are added to a solution of 200 mg (0.61 mmol) of the compound (2) in 15 ml of dimethylformamide, and the reaction solution is left to stir at room temperature for 2 h. It is then concentrated down to dryness, and the oily residue is reevaporated twice with toluene and twice with acetone. The crude product is adsorbed on silica gel and purified by column chromatography (20×5 cm column, dichloromethane/methanol 9:1). Compound (7) is obtained, as colorless platelets (150 mg, 0.4 mmol, 65%): m.p. 177° C., after concentrating the main fraction and recrystallizing the residue from acetone/methanol 9:1.

TLC (silica gel, dichloromethane/methanol 9:1): $R_f$=0.65.

$^1$H-NMR ([D$_6$] DMSO): δ=2.20 (m, 2'α-H), 2.50 (m, 2'β-H, overlapped by DMSO), 3.18, 3.19 (2s, 2 N—CH$_3$), 3.54 (m, 2H, 5'-H), 3.86 (m, 4'-H), 4.35 (m, 3'-H), 5.01 (t, J=5.5 Hz, 5'-OH), 5.26 (d, J=5.0 Hz, 3'-OH), 6.57 (pt, J=6.9 Hz, 1'-H), 7.70 (s, 6-H), 8.34 (s, 2-H), 8.82 (s, N=CH).

| C$_{14}$H$_{18}$BrN$_5$O$_3$ (384.2) | Calc. | C 43.77 | H 4.72 | N 18.23 |
|---|---|---|---|---|
| | Found | C 43.92 | H 4.80 | N 18.11 |

Example 5

4-Benzoylamino-5-chloro-7-[(2-deoxy-β-D-erythropentofuranosyl)-5'-O-(4,4'-dimethoxytriphenylmethyl)]-7H-pyrrolo[2,3-d]pyrimidine (8)

500 mg (1.28 mmol) of compound (4) are evaporated twice with dry pyridine and then dissolved in 20 ml of absolute pyridine. 650 mg (1.95 mmol) of dimethoxytrityl chloride are added, and the mixture is stirred at room temperature for 1 h. It is then hydrolyzed with 10 ml of a 5% aqueous solution of NaHCO$_3$ and extracted twice with 25 ml of dichloromethane on each occasion. After the combined organic phases have been dried over Na$_2$SO$_4$ chromatography takes place on silica gel (20×5 cm column, dichloromethane/methanol 9:1). The residue which is obtained after inspissating the main zone yields, after evaporating with acetone, 680 mg (0.99 mmol, 77%) of a yellowish foam. For the purification, the substance is dissolved in a little dichloromethane, and this solution is slowly added dropwise, while stirring vigorously, to a 200-fold excess of n-hexane. Compound (8) is isolated as a white, amorphous solid.

TLC (silica gel, dichloromethane/methanol 9:1): $R_f$=0.5.

$^1$H-NMR ([D$_6$] DMSO): δ=2.30 (m, 2'α-H), 2.50 (m, 2'β-H, overlapped by DMSO), 3.15 (m, 2H, 5'-H), 3.73 (s, 6H, 2 OCH$_3$), 3.98 (m, 4'-H), 4.42 (m, 3'-H), 5.40 (d, J=5.0 Hz, 3'-OH), 6.69 (pt, J=6.7 Hz, 1'-H), 6.84 (m, 4H, DMT), 7.2–7.8 (m, 12H, aromatic protons), 7.87 (s, 6-H), 8.06 (d, 2H, ortho-H$_{Bz}$), 8.70 (s, 2-H), 11.0 (br, 4-NH).

| C$_{39}$H$_{35}$ClN$_4$O$_6$ (691.2) | Calc. | C 67.77 | H 5.10 | N 8.11 |
|---|---|---|---|---|
| | Found | C 67.70 | H 5.05 | N 8.19 |

Example 6

4-Benzoylamino-5-bromo-7-[(2-deoxy-β-D-erythropentofuranosyl)-5'-O-(4,4'-dimethoxytriphenylmethyl)]-7H-pyrrolo[2,3-d]pyrimidine (9)

500 mg (1.15 mol) of compound (5) are evaporated twice with dry pyridine and subsequently dissolved in 20 ml of absolute pyridine. 585 mg (1.75 mmol) of dimethoxytrityl chloride are added, and the mixture is stirred at room temperature for 1 h. It is then hydrolyzed with 10 ml of a 5% aqueous solution of NaHCO$_3$ and extracted twice with 25 ml of dichloromethane on each occasion. After the combined organic phases have been dried over Na$_2$SO$_4$, chromatography takes place on silica gel (20×5 cm column, dichloromethane/methanol 9:1). The residue which is obtained after inspissating the main zone yields, after evaporating with acetone, 620 mg (0.93 mmol, 80%) of a yellowish foam. For the purification, the substance is dissolved in a little dichloromethane and this solution is slowly added dropwise, while stirring vigorously, to a 200-fold excess of n-hexane. Compound (9) precipitates out as a white amorphous solid and is filtered off with suction.

TLC (silica gel, dichloromethane/methanol 9:1): $R_f$=0.55.

$^1$H-NMR ([D$_6$] DMSO): δ=2.30 (m, 2'α-H), 2.50 (m, 2'β-H, overlapped by DMSO), 3.15 (m, 2H, 5'-H), 3.73 (s, 6H, 2 OCH$_3$), 3.98 (m, 4'-H), 4.42 (m, 3'-H), 5.40 (d, J=5.0 Hz, 3'-OH), 6.69 (pt, J=6.7 Hz, 1'-H), 6.84 (m, 4H, DMT), 7.2–7.8 (m, 12H, aromatic protons), 7.87 (s, 6-H), 8.06 (d, 2H, ortho-H$_{Bz}$), 8.70 (s, 2-H), 11.0 (br, 4-NH).

| C$_{39}$H$_{35}$BrN$_4$O$_6$ (735.6) | Calc. | C 63.68 | H 4.79 | N 7.62 |
|---|---|---|---|---|
| | Found | C 63.85 | H 4.67 | N 7.52 |

Example 7

4-Benzoylamino-7-[(2-deoxy-β-D-erythropentofuranosyl) -5'-O-(4,4'-dimethoxytriphenylmethyl)]-5-methyl-7H-pyrrolo[2,3-d]pyrimidine (10)

500 mg (1.36 mmol) of compound (6) are evaporated twice with 20 ml of dry pyridine on each occasion and dissolved in 20 ml of absolute pyridine, and this solution is stirred, at room temperature for 1 h, together with 690 mg (2.1 mmol) of dimethoxytrityl chloride. The mixture is worked up in an analogous manner to that employed for compound (8), and chromatographed on silica gel (20×5 cm column, dichloromethane/methanol 9:1). 720 mg (1.05 mmol, 77%) of the completely protected compound (10) are obtained, as a yellowish foam, from the main zone. Purification, by reprecipitating from n-hexane, yields a colorless, amorphous solid.

TLC (silica gel, dichloromethane/methanol 9:1): $R_f$=0.5.

$^1$H-NMR ([D$_6$] DMSO): δ=2.08 (s, 5-CH$_3$), 2.30 (m, 2'α-H), 2.50 (m, 2'β-H, overlapped by DMSO), 3.10 (m, 2H, 5'-H), 3.73 (s, 6H, 2 OCH$_3$), 3.97 (m, 4'-H), 4.44 (m, 3'-H), 5.39 (d, J=5.0 Hz, 3'-OH), 6.67 (pt, J=6.7 Hz, 1'-H), 6.85 (m, 4H, DMT), 7.2–7.8 (m, 12H, aromatic protons), 7.58 (s, 6-H), 8.06 (d, 2H, ortho-H$_{Bz}$), 8.60 (s, 2-H), 10.95 (br, 4-NH).

| C$_{40}$H$_{38}$N$_4$O$_6$ (670.8) | Calc. | C 71.63 | H 5.71 | N 8.35 |
|---|---|---|---|---|
| | Found | C 71.48 | H 5.71 | N 8.36 |

Example 8

4-Benzoylamino-5-chloro-7-[(2-deoxy-β-D-erythropentofuranosyl)-5'-O-(4,4'-dimethoxytriphenylmethyl)]-7H-pyrrolo[2,3-d]pyrimidine-3'-(triethylammonium phosphonate) (11)

840 mg (12.0 mmol) of 1,2,4-1H-triazole are added, at room temperature and under an argon atmosphere, to a solution of 315 μl (3.7 mmol) of phosphorus trichloride and 4.1 ml (37.0 mmol) of N-methylmorpholine in 40 ml of absolute dichloromethane. After the mixture has been stirred for 30 minutes, it is cooled down to 0° C. and a solution of 500 mg (0.74 mmol) of the fully protected nucleoside (8) in 10 ml of dry dichloromethane is added dropwise over a period of 10 min. The mixture is left to stir at room temperature for a further 10 min, and 30 ml of 1 M triethylammonium bicarbonate buffer (TBC, pH=7.5) are then added. The phases are separated and the aqueous phase is extracted several times with $CH_2Cl_2$; the combined organic phases are then dried over $Na_2SO_4$. The solvent is evaporated off and the remaining foam is chromatographed on silica gel (20×5 cm column, 0.5 l dichloromethane/$Et_3N$ 98:2, and then dichloromethane/methanol/$Et_3N$ 88:10:2). After the main zone has been concentrated, the residue is taken up in 50 ml of dichloromethane and this solution is extracted five times with 25 ml of 0.1 M TBC buffer on each occasion. 445 mg (0.52 mmol, 70%) of the phosphonate (11) are obtained, as a colorless foam, after drying the organic phase over $Na_2SO_4$ and evaporating off the solvent. For the further purification, this foam is reprecipitated from n-hexane in an analogous manner to that used for the fully protected nucleoside (8).

TLC (silica gel, dichloromethane/methanol 9:1): $R_f$=0.6.

$^1$H-NMR ([$D_6$] DMSO): δ=1.16 (t, 9H, $(CH_3CH_2)_3N$), 2.50 (m, 2'α-H, overlapped by DMSO), 2.74 (m, 2'β-H), 3.00 (q, 6H, $(CH_3CH_2)_3N$), 3.33 (m, 2H, 5'-H), 3.72 (s, 6H, 2 $OCH_3$), 4.15 (m, 4'-H), 4.78 (m, 3'-H), 6.66 (d, J=585.8 Hz, P—H), 6.69 (pt, J=7.8 Hz, 1'-H), 6.84 (m, 4H, DMT), 7.2–7.7 (m, 12H, aromatic protons), 7.79 (s, 6-H), 8.04 (d, 2H, ortho-$H_{Bz}$), 8.69 (s, 2-H), 10.6 (br, 4-NH).

$^{31}$P-NMR ([$D_6$] DMSO): δ=1.16 ppm (dd, $^1$J(PH)=588 Hz, $^3$J(PH)=8.6 Hz. $C_{45}H_{51}ClN_5O_8P$ (900.8)

Example 9

4-Benzoylamino-5-bromo-7-[(2-deoxy-β-D-erythropentofuranosyl)-5'-O-(4,4'-dimethoxytriphenylmethyl)]-7H-pyrrolo[2,3-d]pyrimidine-3'-(triethylammonium phosphonate) (12)

770 mg (11.0 mmol) of 1,2,4-1H-triazole are added, at room temperature and under an argon atmosphere, to a solution of 290 μl (3.4 mmol) of phosphorus trichloride and 3.8 ml (34.0 mmol) of N-methylmorpholine in 30 ml of absolute dichloromethane. After the mixture has been stirred for 30 minutes, it is cooled down to 0° C. and a solution of 500 mg (0.68 mmol) of the completely protected nucleoside (9) in 10 ml of dry dichloromethane is added dropwise within the space of 10 min. The mixture is left to stir at room temperature for a further 10 min and 30 ml of 1 M triethylammonium bicarbonate buffer (TBC, pH=7.5) are then added. The phases are separated, the aqueous phase is extracted several times with $CH_2Cl_2$, and the combined organic phases are dried over $Na_2SO_4$. The solvent is evaporated off and the remaining foam is chromatographed on silica gel (20×5 cm column, 0.5 l of dichloromethane/ $Et_3N$, 98:2, and, after that, dichloromethane/methanol/$Et_3N$, 88:10:2). After the main zone has been concentrated, the residue is taken up in 50 ml of dichloromethane and this solution is extracted five times with 25 ml of 0.1 M TBC buffer on each occasion. 410 mg (0.46 mmol, 67%) of the phosphonate (12) are obtained as a colorless foam after the organic phase has been dried over $Na_2SO_4$ and the solvent has been evaporated off. For the further purification, this foam can be reprecipitated from n-hexane in an analogous manner to that for the completely protected nucleoside (9).

TLC (silica gel, dichloromethane/methanol 9:1): $R_f$=0.7.

$^1$H-NMR ([$D_6$] DMSO): δ=1.16 (t, 9H, $(CH_3CH_2)_3N$), 2.50 (m, 2'α-H, overlapped by DMSO), 2.78 (m, 2'β-H), 3.00 (q, 6H, $(CH_3CH_2)_3N$), 3.22 (m, 2H, 5'-H), 3.73 (s, 6H, 2 $OCH_3$), 4.17 (m, 4'-H), 4.82 (m, 3'-H), 6.68 (d, J=588.5 Hz, P—H), 6.69 (pt, J=6.7 Hz, 1'-H), 6.90 (m, 4H, DMT), 7.2–7.8 (m, 12H, aromatic protons), 7.86 (s, 6-H), 8.07 (d, 2H, ortho-$H_{Bz}$), 8.70 (s, 2-H), 11.05 (br, 4-NH).

$^{31}$P-NMR ([$D_6$] DMSO): δ=1.16 ppm (dd, $^1$J(PH)=588 Hz, $^3$J(PH)=8.6 Hz). $C_{45}H_{51}BrN_5O_8P$ (900.8)

Example 10

4-Benzoylamino-7-[(2-deoxy-β-D-erythropentofuranosyl) -5'-O-(4,4'-dimethoxytriphenylmethyl)]-5-methyl-7H-pyrrolo[2,3-d]pyrimidine-3'-(triethylammonium phosphonate) (13)

0.78 g (11.3 mmol) of 1,2,4-H-triazole are added, at room temperature and under an argon atmosphere, to a solution of 25 ml of absolute dichloromethane, 290 μl (3.4 mmol) of phosphorus trichloride and 3.44 g (34.0 mmol) of N-methylmorpholine. After it has been stirred for 30 minutes, the reaction solution is cooled down to 0° C. and a solution of 500 mg (0.75 mmol) of the fully protected nucleoside (10) in 15 ml of dichloromethane is added within the space of 10 min. The mixture is allowed to stir at room temperature for a further 20 min and is then hydrolyzed with 1 M triethylammonium bicarbonate buffer (TBC, pH=7.5). After the phases have been separated, the aqueous phase has been extracted three times with 20 ml of dichloromethane on each occasion, and the organic phase has been dried and concentrated by evaporation, the residue is chromatographed on silica gel (20×5 cm column, 0.5 l of dichloromethane/$Et_3N$, 98:2, and, after that, dichloromethane/methanol/$Et_3N$, 88:10:2). The main zone is inspissated and the residue is taken up in 50 ml of dichloromethane and this solution is extracted several times with 0.1 M TBC buffer. 440 mg (0.53 mmol, 70%) of the compound (13) are obtained as a colorless foam after drying the organic phase over $Na_2SO_4$ and evaporating off the solvent.

TLC (silica gel, dichloromethane/methanol 9:1): $R_f$=0.65.

$^1$H-NMR ([$D_6$] DMSO): δ=1.16 (t, 9H, $(CH_3CH_2)_3N$), 2.09 (s, 5-$CH_3$), 2.24 (m, 2'α-H), 2.67 (m, 2'β-H), 3.00 (q, 6H, $(CH_3CH_2)_3N$), 3.20 (m, 2H, 5'-H), 3.73 (s, 6H, 2 $OCH_3$), 4.13 (m, 4'-H), 4.83 (m, 3'-H), 6.65 (pt, J=6.5 Hz, 1'-H), 6.68 (d, J=588.5 Hz, P—H), 6.85 (m, 4H, DMT), 7.2–7.6 (m, 12H, aromatic protons), 7.58 (s, 6-H), 8.05 (d, 2H, ortho-$H_{Bz}$), 8.60 (s, 2-H), 10.98 (br, 4-NH).

$^{31}$P-NMR ([$D_6$] DMSO): δ=1.08 ppm (dd, $^1$J(PH)=577 Hz, $^3$J(PH)=8.9 Hz). $C_{46}H_{54}N_5O_8P$ (835.8)

Example 11

4-Amino-5-bromo-7-(2-deoxy-β-D-erythropentofuranosyl)-7H-pyrrolo[2,3-d]pyrimidine 5'-O-triphosphate, triethylammonium Salt Compound (2) (33 mg, 0.1 mmol) is dissolved, together with 1,8-bis(dimethylamino)naphthalene (33 mg, 0.15 mmol), in trimethyl phosphate (0.25 ml) while warming gently. After the solution has been cooled down to 0° C., freshly distilled $POCl_3$ (12 μl, 0.13 mmol) is added. The reaction mixture is maintained at 4° C. for 4 h and a solution comprising tri-n-butylanmonium diphosphate (0.5 m in DMF, 1 ml) and tri-n-butylamine (100 μl, 0.42 mmol) is then added. After the mixture has been stirred at 0° C. for 3 min, 1 M TBC buffer (10 ml) is added and the whole is evaporated to dryness. The residue is chromatographed on DEAD Sephadex (1.5×20 cm column, $HCO_3^-$ form). After washing the column with approximately 500 ml of $H_2O$, chromatography took place using a linear gradient of $H_2O$/0.9 M TBC buffer (1 l in each case). During this procedure, the triphosphate (0.019 mM, 20%) is obtained at approximately 0.5 M TBC buffer.

TLC (silica gel, i-propanol/$H_2O$/$NH_3$, 3:1:1): $R_f$=0.2. UV ($H_2O$): $\lambda_{max}$=269 nm.

$^{31}$P-NMR (0.1 M tris-HCl, pH 8.0, 100 mM EDTA/$D_2O$): −11.87 (d, J=20.2, $P_\gamma$); −10.98 (td, J=20.0 and 6.0, $P_\alpha$); −23.06 (t, J=20.2, $P_\beta$).

Example 12

4-Amino-7-(2-deoxy-β-D-erythropentofuranosyl)-5-iodo-7H-pyrrolo[2,3-d]pyrimidine (14) (5-iodo-2'-deoxytubercidin)

25% aqueous ammonia is added to 1.0 g (2.5 mmol) of 4-chloro-7-[2-deoxy-3,5-di-O-(4-toluoyl)-β-D-erythropentofuranosyl]-5-iodo-7H-pyrrolo[2,3-d] pyrimidine which is dissolved in 80 ml of dioxane (80 ml). The mixture is stirred in a steel cylinder at 110° C. for 48 h. After the solvent has been evaporated off, the concentrated residue is chromatographed on silica gel (20×5 cm column, solvent B). Colorless crystals from MeOH (0.75 g, 2.0 mmol, 45%). M.p. 194° C. TLC: $R_f$ 0.4 ($CH_2Cl_2$/MeOH, 9:1). UV (MeOH) 283 nm (5 800).

$^1$H-NMR ($D_6$-DMSO): 2.16 (m, H-2'α), 2.46 (m, H-2'β, overlapped by DMSO), 3.54 (m, 2-H, H-5'), 3.81 (m, H-4'), 4.33 (m, H-3'), 5.00 (t, J=5.1 Hz, 5'-OH), 5.23 (d, J=5.1 Hz, 3'-OH), 6.49 (pt, J=6.7 Hz, H-1'), 6.65 (br, $NH_2$), 7.65 (s, H-6), 8.10 (s, H-2).

$^{13}$C-NMR ($D_6$-DMSO) 157.3 (C-4), 152.0 (C-2), 149.8 (C-7a), 126.9 (C-6), 103.2 (C-4a), 87.5 (C-4'), 83.0 (C-1'), 71.0 (C-3'), 62.0 (C-5'), 51.9 (C-5), 39.8 (C-2').

Anal. calculated for $C_{11}H_{13}IN_4O_3$: C 35.13, H 3.48, N 14.90; found: C 35.33, H 3.69, N 15.01.

Example 13

Cross-Coupling Reaction of 5-iodo-2'-deoxytubercidin (14)

5-Iodo-2'-deoxytubercidin (14) (200 mg, 0.532 mmol) and copper(I) iodide (10 mg, 10 mol %) are suspended in 3 ml of dry DMF, which has been previously flushed with argon, and alkyne (6–15 eq.), dry triethylamine (108 mg, 1.06 mmol, 2 eq.) and tetrakis(triphenylphosphine) palladium (0) (30.75 mg, 0.027 mmol, 5 mol %) are added to this mixture.

Within a few hours, the mixture turns into a clear yellow solution. The reaction is continued until the starting compounds are used up (monitoring by thin layer chromatography). The reaction mixture is then diluted with 5 ml of methanol/dichloromethane (1:1), and Dowex 1×8 (100–200 mesh; 500 mg, bicarbonate form) is added. Once the gas formation has ceased, after 15 minutes of stirring, the reaction mixture is stirred for a further 30 minutes. It is then filtered and the matrix is washed with methanol/dichloromethane (1:1).

The filtrates are combined and dried. The dried residue is immediately chromatographed on a silica gel column (25 g) using dichloromethane having an increasing content of methanol (10, 15, 20%). The substituted 2'-deoxytubercidin derivative is obtained after evaporating the main fraction.

Example 14

4-Benzoylamino-5-(1-propynyl-3-trifluoroacetamide) -7-[(2-deoxy-β-D-erythropentofuranosyl) -5'-O-(4,4'-dimethoxytriphenylmethyl)]-7H-pyrrolo[2,3-d]-pyrimidine-3'-(triethylammonium phosphonate) (15)

a) 7-Deaza-2'-deoxy-7-(1-propynyl-3-trifluoroacetamide) adenosine

5-Iodo-2'-deoxytubercidin (14) from Example 12 is coupled, under the conditions described in Example 13 and over a period of 9 h, to N-propargyltrifluoroacetamide. The following quantities are employed: 5-iodo-2'-deoxytubercidin (14) (200 mg, 0.532 mmol), copper(I) iodide (5.0 mg, 0.0236 mmol, 5 mol %), DMF (3 ml), N-propargyltrifluoroacetamide (482 mg, 3.2 mmol, 6 eq.), triethylamine (108 mg, 1.06 mmol, 2 eq.) and tetrakis (triphenylphosphine)palladium (0) (61.5 mg, 0.0532 mmol, 10 mol %). Following chromatography, the solid is recrystallized from ethyl acetate: pale yellow crystals (70 mg, 0.176 mmol, 33%). M.p. 187–188° C. TLC: $R_f$ 0.30 ($CH_2Cl_2$/MeOH, 9:1). UV (MeOH) 237 (14 400), 279 (14 200).

$^1$H-NMR ($D_6$-DMSO) 10.07 (s, 1H, NHTFA), 8.12 (s, 1H, H-2), 7.76 (s, 1H, H-6), 6.79 (broad s, 2H, $NH_2$), 6.49 (pt, 1H, H-1', J=6.6 Hz), 5.25 (d, 1H, 3'-OH, J=3.0 Hz), 5.05 (t, 1H, 5'-OH, J=4.5 Hz), 4.35 (m, 1H, H-3'), 4.32 (d, 2H, $CH_2$, J=4.2 Hz), 3.84 (m, 1H, H-4'), 3.56 (m, 2H, H-5'), 2.47 (m, 1H, H-2'β), 2.19 (m, 1H, H-2'α).

$^{13}$C-NMR ($D_6$-DMSO): 157.4 (C-4), 156.4 and 156.1 (C=O), 152.7 (C-2), 149.2 (C-7a), 126.5 (C-6), 116.8 and 114.6 ($CF_3$), 102.2 (C-4a), 94.0 (C-5), 87.5 (C-4'), 86.7 and 76.2 (C=C), 83.2 (C-1'), 70.9 (C-3'), 61.8 (C-5'), 39.6 (C-2', overlapped by DMSO), 29.9 ($CH_2$).

Anal. calculated for $C_{16}H_{16}F_3N_5O_4$: C 48.13, H 4.04, N 17.54; found: C 48.26, H 4.13, N 17.58.

b) 4-Benzoylamino-5-(1-propynyl-3-trifluoroacetamide)-7-[(2-deoxy-β-D-erythropentofuranosyl)-7H-pyrrolo[2,3-d]-pyrimidine The benzoylamino protective group is inserted into 7-deaza-2'-deoxy-7-(1-propynyl-3-trifluoroacetamide) adenosine in analogy with Example 1.

c) 4-Benzoylamino-5-(1-propynyl-3-trifluoroacetamide)-7-[(2-deoxy-β-D-erythropentofuranosyl)-5'-O-(4,4'-dimethoxytriphenylmethyl)]-7H,-pyrrolo[2,3-d]-pyrimidine The Dmt-hydroxyl protective group is inserted into 4-benzoylamino-5-(1-propynyl-3-trifluoroacetamide)-7-[(2-deoxy-β-D-erythropentofuranosyl)-7H-pyrrolo[2,3-d]-pyrimidine in analogy with Example 5.

d) The title compound (15) is prepared from 4-benzoylamino-5-(1-propynyl-3-trifluoroacetamide)-7-((2-deoxy-β-D-erythropentofuranosyl)-5'-O-(4,4'-dimethoxytriphenylmethyl)-7H-pyrrolo[2,3-d]pyrimidine in analogy with Example 8.

Example 15

4-Benzoylamino-5-(1-pentynyltrifluoroacetamide)-7-[(2-deoxy-β-D-erythropentofuranosyl)-5'-O-(4,4'-dimethoxytriphenylmethyl)]-7H-pyrrolo [2,3-d]-pyrimidine-3'-(triethylammonium phosphonate) (16)

a) 7-Deaza-2'-deoxy-7-(1-pentynyltrifluoroacetamide) adenosine

5-Iodo-2'-deoxytubercidin (14) from Example 12 is coupled, under the conditions described in Example 13 and over a period of 48 h, to 5-trifluoroacetamide-1-pentyne. The following quantities are employed: 5-iodo-2'-deoxytubercidin (200 mg, 0.532 mmol), copper(I) iodide (5 mg, 0.0236 mmol, 5 mol %), DMF (3 ml), 5-trifluoroacetamide-1-pentyne (953 mg, 5.32 mmol, 10 eq.), triethylamine (108 mg, 1.06 mmol, 2 eq.) and tetrakis (triphenylphosphine)palladium (0) (61.5 mg, 0.0532 mmol, 10 mol %). Following chromatography, a weakly yellowish oily residue (84.1 mg, 0.197 mmol, 37%) is obtained from the liquid by crystallization. M.p. 51–52° C. TLC: $R_f$ 0.35 ($CH_2Cl_2$/MeOH, 9:1). UV (MeOH) max=239 (14 300), 280 (10 900).

¹H-NMR (D₆-DMSO): 8.08 (s, 1H, H-2), 7.64 (s, 1H, H-6), 6.46 (pt. 1H, H-1', J=6.9 Hz), 4.32 (m, 1H, H-3'), 3.80 (m, 1H, H-4'), 3.59–3.28 (several m, 5H, H-5', CH₂—CH₂—CH₂—N), 2.47 (m, 1H, H-2'β), 2.17 (m, 1H, H-2'α), 1.76 (quintet, 2H, CH₂—CH₂—CH₂—N). ¹³C-NMR (D₆-DMSO): 157.6 (C-4), 156.5 and 156.2 (C=O), 152.7 (C-2), 149.2 (C-7a), 125.7 (C-6), 118.5 and 114.0 (CF₃), 102.3 (C-4a), 95.5 (C-5), 91.6 (C=C, 1"), 87.6 (C-4'), 83.2 (C-1'), 74.0 (C=C, 2"), 71.0 (C-3'), 62.0 (C-5'), 39.6 and 38.6 (C-2' and CH₂, overlapped by DMSO), 27.7 (CH₂), 16.6 (CH₂).

Anal. calculated for $C_{18}H_{20}N_5O_4F_3$: C 50.59, H 4.72, N 16.39; found: C 50.65, H 4.82, N 16.32.

The title compound (16) is obtained from 7-deaza-2'-deoxy-7-(1-pentynyltrifluoroacetamide)adenosine in analogy with Examples 14b), 14c) and 14d).

Example 16

2'-Deoxy-7-deaza-7-(2-carboxyethenyl) adenosine (17).

5-Iodo-2'-deoxytubercidin (14) from Example 12 is coupled, under the conditions described in Example 13 and over a period of 65 h, to methyl acrylate. The following quantities are employed: 5-iodo-2'-deoxytubercidin (200 mg, 0.532 mmol), copper(I) iodide (5 mg, 0.0236 mmol, 5 mol %), DMF (3 ml), triethylamine (108 mg, 1.06 mmol, 2 eq.), methyl acrylate (686 mg, 8.0 mmol, 15 eq.) and tetrakis(triphenylphosphine)palladium (0) (61.5 mg, 0.0532 mmol, 10 mol %). A pale yellow foam is obtained after chromatographic purification, and 71.1 mg of solid substance (40%) are obtained after washing with dichloromethane. M.p. 101–102° C. TLC: R_f 0.40 (CH₂Cl₂/MeOH, 9:1). UV (MeOH) max=268.0 (13 500), 324.8 (11 900).

¹H-NMR (D₆-DMSO): 8.11 (2s, 2H, H-2 and H-6), 7.94 (d, 1H, H-1", J=15.6 Hz), 6.86 (s, 2H, NH₂), 6.51 (pt, 1H, H-1', J=6.6 Hz), 6.4 (d, 1H, H-2", J=15.6 Hz), 5.26 (d, 1H, 3'-OH, J=3.6 Hz), 5.04 (t, 1H, 5'-OH, J=5.1 Hz), 4.36 (m, 1H, H-3'), 3.83 (m, 1H, H-4'), 3.70 (s, 3H, OCH₃), 3.55 (m, 1H, H-5'), 2.45 (m, 1H, H-2'β), 2.22 (m, 1H, H-2'α).

¹³C-NMR (D₆-DMSO): 166.9 (C=O ), 158.0 (C-4), 152.1 (C-2), 151.2 (C-7a), 137.4 (CH—C=O), 123.7 (C-6), 115.5 (CH=CH—C=O), 111.5 (C-5), 101.0 (C-4a), 87.6 (C-4'), 83.2 (C-1'), 70.9 (C-3'), 62.0 (C-5'), 51.2 (OCH₃), 39.6 (C-2'), overlapped by DMSO).

Anal. calculated for $C_{15}H_{18}N_4O_5$: C 53.89, H 5.43, N 16.76; found: C 53.79, H 5.56, N 16.74.

Example 17

7-[2-Deoxy-3,5-di-O-(2-methylpropionyl)-β-D-erythropentofuranosyl]-4-methoxy-2-[(formyl) amino]-7H-pyrrolo[2,3-d]-pyrimidine (18).

7-(2-Deoxy-β-D-erythropentofuranosyl)-4-methoxy-2-[(formyl)amino]-7H-pyrrolo[2,3-d]pyrimidine (1.0 g, 3.3 mmol) [F. Seela, H. Driller, Nucleosides, Nucleotides 1989, 8, 1–21] in acetonitrile (20 ml) was stirred, at room temperature for 15 hours, together with isobutyric anhydride (33 mmol) in the presence of triethylamine (23 mmol). The solvent is evaporated off and the residue is reevaporated with methanol. It is then chromatographed in the eluent methylene chloride/acetone (95:5), and the main zone is isolated and the constituent compound is recrystallized from cyclohexane. 1.26 g (89%) of a colorless solid.

¹H-NMR ([D₆] DMSO), δ: 1.05–1.14 (m, 4CH₃), 2.60, 2.90 (m, CH and 2'-Ha,b), 4.02 (S, OCH₃), 4.16 (m, 5'-H), 4.26 (m, 4'-H), 5.35 (m, 3'-H), 6.47 (m, 1'-H), 6.52 (d, 5-H), 7.39 (d, 6-H), 9.44 (d, NH), 10.71 (d, HCO).

Example 18

5-Bromo-7-[2-deoxy-3,5-di-O-(2-methylpropionyl)-β-D-erythropentofuranosyl]-4-methoxy-2-[(formyl) amino]-7H-pyrrolo[2,3-d]pyrimidine (19).

A solution of compound 18 (10.1 mmol) in dimethylformamide was stirred, at room temperature for 1 hour, together with N-bromosuccinimide (10.1 mmol). A few drops of 5% aqueous NaHCO₃ are added to the solution, in order to buffer it, and methylene chloride is then added. The organic phase is shaken with water, separated, dried over sodium sulfate and evaporated. Chromatography of the residue on a silica gel column in the eluent dichloromethane/acetone (95:5) results in two zones. The evaporation residue from the slowly migrating main zone yields colorless (19) (75%) as a solid.

¹H-NMR ([D₆] DMSO), δ: 1.05–1.14 (m, 4CH₃), 2.60, 2.88 (m, CH and 2'-Ha,b), 4.04 (s, OCH₃), 4.16 (m, 5'-H), 4.22 (m, 4'-H), 5.34 (m, 3'-H), 6.46 (m, 1'-H), 7.60 (s, 6-H), 9.43 (s, NH), 10.86 (s, HCO).

A colorless solid, which was characterized as 5,6-dibromo-7-[2-deoxy-3,5-di-O-(2-methylpropionyl)-β-D-erythropentofuranosyl]-4-methoxy-2-[(formyl)amino]-7H-pyrrolo[2,3-d]pyrimidine, is obtained from the rapidly migrating subsidiary zone from the abovementioned reaction.

¹H-NMR ([D₆] DMSO), δ: 0.99–1.13 (m, 4CH₃), 2.59, 3.58 (m, CH and 2'-Ha,b), 4.03 (s, OCH₃), 4.16 (m, 5'-H), 4.30 (m, 4'-H), 5.56 (m, 3'-H), 6.39 (m, 1'-H), 9.42 (s, NH), 10.91 (s, HCO).

Example 19

5-Chloro-7-[2-deoxy-3,5-di-O-(2-methylpropionyl)-β-D-erythropentofuranosyl ]-4-methoxy-2-amino-7H-pyrrolo-[2,3-d]pyrimidine (20).

Using N-chlorosuccinimide, the substance was prepared and worked up in analogy with compound (19). The halogenation reaction time was 8 hours. Acetonitrile/DMF (4:1) was used as the solvent. Colorless solid (70%).

¹H-NMR ([D₆] DMSO), δ: 1.07–1.13 (m, 4CH₃), 2.59, 2.74 (m, CH and 2'-Ha,b), 3.93 (s, OCH₃), 4.15 (m, 5'-H), 4.21 (m, 4'-H), 5.25 (m, 3'-H), 6.39 (m, 1'-H), 6.47 (5, NH₂), 7.20 (s, 6-H).

The compound 5,6-dichloro-7-[2-deoxy-3,5-di-O-(2-methylpropionyl)-β-D-erythropentofuranosyl]-4-methoxy-2-amino-7H-pyrrolo[2,3-d]pyrimidine, in the form of a colorless solid, was obtained an a by-product.

¹H-NMR ([D₆] DMSO), δ: 1.03–1.13 (m, 4CH₃), 2.58, 3.40 (m, CH and 2'-Ha,b), 3.93 (s, OCH₃), 4.16 (m, 5'-H), 4.37 (m, 4'-H), 5.44 (m, 3'-H), 6.37 (m, 1'-H), 6.58 (s, NH₂).

Example 20

2-Amino-7-(2'-deoxy-β-erythropentofuranosyl)-3,7-dihydro-5-bromo-4-pyrrolo [2,3-d]pyrimidin-4-one (21)

Compound (19) is reacted using a known method [F. Seela, B. Westermann, U. Bindig, J. Chem. Soc. Perkin Trans I 1988, 699]. 500 mg of compound (19) are heated under reflux for 3 hours in 200 ml of 2 N NaOH. The cooled solution is neutralized with glacial acetic acid, the inorganic residue is filtered off, and the aqueous phase is evaporated. Recrystallization from water results in colorless crystals of (21).

Example 21

2-Amino-7-(2'-deoxy-β-erythropentofuranosyl)-3,7-dihydro-5-bromo-4-pyrrolo[2,3-d]pyrimidin-4-one (22)

Compound (22) is prepared in analogy with the method described in Example 20 and proceeding from compound (20). Recrystallization from water results in colorless crystals of (22).

Example 22

4-Amino-7-[2-deoxy-β-D-erythropentofuranosyl]-5-trimethylsilylethynyl-7H-pyrrolo[2,3-d]pyrimidine (23)

Compound (23) is prepared from trimethylsilylacetylene in accordance with the general protocol for the cross-coupling reaction in Example 13. Colorless solid. Yield 54%.

Calc. C 55.47, H 6.40, N 16.17; found C 55.57, H 6.53, N 16.20.

$^1$H-NMR (DMSO): 8.12 (s, 1H, H-2), 7.80 (s, 1H, H-6), 6.76 (broad, 2H, NH$_2$), 6.47 ("t", 1H, H-1', J=6.7 Hz), 5.23 (d, 1H, 3'-OH, J=3.3 Hz), 5.07 (t, 1H, 5'-OH), 4.33 (m, 1H, H-3'), 3.87 (m, 1H, H-4'), 3.54 (m, 2H, H-5'), 2.46 (m, 1H, H-2'), 2.17 (m, 1H, H-2'), 0.73 (s, 9H, Me).

Example 23

4-Amino-7-[2-deoxy-β-D-erythropentofuranosyl]-5-ethynyl-7H-pyrrolo[2,3-d]pyrimidine (24)

200 mg of compound (23) are dissolved in 20 ml of MeOH. Adding 8 mg of K$_2$CO$_3$ results in hydrolysis after 1 h of stirring. After the solution has been subjected to rotary evaporation, the residue is chromatographed on silica gel in the eluent methylene chloride/MeOH (8:1). Recrystallization from MeOH results in colorless crystals (73%).

Calc. C 56.93, H 5.15, N 20.43; found C 56.77, H 5.71, N 20.42.

$^1$H-NMR (DMSO): 8.13 (s, 1H, H-2), 7.81 (s, 1H, H-6), 6.65 (broad, 2H, NH$_2$), 6.49 (t, 1H, H-1'), 5.25 (m, 1H, 3'-OH), 5.05 (m, 1H, 5'-OH), 4.36 (m, 1H, H-3'), 4.26 (s, 1H, ethyne), 3.84 (s, 1H, H-4'), 3.56 (m, 2H, H-5'), 2.47 (m, 1H, H-2'), 2.21 (m, 1H, H-2').

Example 24

4-Amino-7-[2-deoxy-β-D-erythropentofuranosyl]-5-hexynyl-7H-pyrrolo[2,3-d]pyrimidine (25)

Compound (25) is prepared in accordance with the general protocol for the cross-coupling reaction (Ex. 13) and using 1-hexyne. Recrystallization from MeOH results in colorless crystals (yield: 48%).

Calc. C 61.80, H 6.71, N 19.96; found C 61.68, H 6.60, N 16.90

$^1$H-NMR (DMSO): 8.31 (s, 1H, H-2), 7.65 (8, 1H, H-6), 6.65 (broad, 2H, NH$_2$), 6.49 ("t", 1H, H-1'), 5.24 (m, 1H, 3'-OH), 5.05 (m, 1H, 5'-OH), 4.50 (m, 1H, 3'-H), 3.84 (m, 1H, H-4'), 3.56 (m, 2H, H-5'), 2.48 (m, 2H, CH$_2$C≡), 2.46 (m, 1H, H-2'), 2.18 (m, 1H, H-2'), 1.54 (m, 2H, CH$_2$), 1.43 (m, 2H, CH$_2$), =0.93 (m, 2H, CH$_3$).

Example 25

2-Amino-6-chloro-7-[2-deoxy-3,5-di-O-acetyl-β-D-erythropentofuranosyl]-4-methoxy-7H-pyrrolo[2,3-d]pyrimidine.

36.6 mg (0.27 mmol) of N-chlorosuccinimide are added to a solution of 50 mg (0.14 mmol) of 2-amino-7-(2-deoxy-3,5-di-O-acetyl-β-D-erythropentofuranosyl)-4-methoxy-7H-pyrrolo[2,3-d]pyrimidine in 3 ml of dichloromethane, and the mixture is stirred at room temperature for 12 h. The solvent is stripped off and the residue is chromatographed on silica gel in CH$_2$Cl$_2$/acetone (9:1). 30 mg (54%) of a colorless foam are obtained from the slowly migrating main zone.

$^1$H-NMR D$_6$ (DMSO): 1.99 (s, 3H, CH$_3$), 2.09 (s, 3H, CH$_3$), 2.37 (m, 1H, H-2'b), 3.93 (s, 3H, OCH$_3$), 4.18 (m, 2H, H-5'), 4.43 (m, 1H, H-4), 5.44 (m, 1H, H-3'), 6.38 (m, 1H, H-1'), 6.42 (s, 1H, H-5).

$^{13}$C-NMR (DMSO): 20.48 (CH$_3$), 20.76 (CH$_3$), 33.78 (C-2'), 52.99 (OCH$_3$), 63.47 (C-5'), 74.31 (C-3'), 80.91 (C-4'), 82.95 (C-1'), 96.45 (C-4a), 98.65 (C-5), 118.12 (C-6), 153.69 (C-7a), 159.25 (C-2), 162.16 (C-4), 169.98 (C=O), 170.09 (C=O).

Example 26

2-Amino-5,6-dichloro-7-[2-deoxy-3,5-di-O-acetyl-β-D-erythropentofuranosyl]-4-methoxy-7H-pyrrolo[2,3-d]-pyrimidine.

The more rapidly migrating zone yields a colorless foam. 6 mg (9.9%).

$^1$H-NMR (DMSO): 1.98 (s, 3H, CH$_3$), 2.07 (s, 3H, CH$_3$), 2.24 (m, 1H, H-2'b), 2.73 (m, 1H, H-2'a), 3.94 (s, 3H, OCH$_3$), 4.14 (m, 2H, H-5'), 4.39 (m, 1H, H-4), 5.40 (m, 1H, H-3'), 6.39 (m, 1H, H-1'), 6.59 (s, 2H, NH$_2$).

$^{13}$C-NMR (DMSO): 20.47 (CH$_3$), 20.75 (CH$_3$), 34.06 (C-2'), 53.34 (OCH$_3$), 63.41 (C-5'), 74.09 (C-3'), 81.01 (C-4'), 83.26 (C-1'), 94.59 (C-4a), 102.08 (C-5), 115.16 (C-6), 151.94 (C-7a), 159.59 (C-2), 162.08 (C-4), 169.97 (C=O), 170.07 (C=O).

UV (MeOH): λ$_{max}$ (ε): 290 nm (8500), 264 nm (13100), 226 nm (22700).

Example 27

7-(2-Deoxy-β-D-erythropentofuranosyl)-4-[(dimethylamino)methylidene]amino-5-iodo-7H-pyrrolo[2,3-d]pyrimidine (26)

A solution of 5-iodo-2'-deoxytubercidin (14) (400 mg, 1.06 mmol) in methanol (20 ml) is stirred, at 40° C. for 2 h, together with N,N-dimethylformamide dimethyl acetyl (2.0 g, 16.8 mmol). After the solvent has been evaporated off, the residue is purified by flash chromatography (FC) (column: 20×5 cm, CH$_2$Cl$_2$/MeOH, 9:1). The main zone yields a colorless foam (389 mg, 85%). TLC (thin layer chromatography, silica gel, CH$_2$Cl$_2$/MeOH, 9:1): R$_f$ 0.46. UV (MeOH): max=229 nm (17400), 277 nm (10400), 323 nm (19000). $^1$H-NMR (D$_6$-DMSO): 2.18 (m, 1H, H$_α$-2'); 2.47 (m, 1H, H$_β$-2', overlapped by DMSO); 3.18, 3.22 (2s, 6H, N(CH$_3$)$_2$); 3.54 (m, 2H, H-5'); 3.81 (m, 1H, H-4'); 4.32 (m, 1H, H-3'); 5.00 (t, J=5.4 Hz, 1H, 5'-OH); 5.23 (d, J=3.9 Hz, 1H, 3'-OH); 6.52 ("t", J=7.0 Hz, 1H, H-1'); 7.70 (s, 1H, H-6); 8.30 (s, 1H, H-2); 8.82 (s, 1H, N=CH). Anal. calculated for C$_{14}$H$_{18}$N$_5$O$_3$I: C 38.99, H 4.21, N 16.24; found: C 39.09, H 4.27, N 16.10.

Example 28

7-(2-Deoxy-β-D-erythropentofuranosyl)-4-[(dimethylamino)methylidene]amino-5-hexynyl-7H-pyrrolo[2,3-d]pyrimidine (27)

A solution of 5-hexynyl-2'-deoxytubercidin (25) (400 mg, 1.21 mmol) in methanol (20 ml) is stirred, at 40° C. for 2 h, together with N,N-dimethylformamide dimethyl acetal (2.0 g, 16.8 mmol). After the solvent has been evaporated off, the residue is purified by flash chromatography (FC) (column: 20×5 cm, $CH_2Cl_2$/MeOH, 9:1). The main zone yields a colorless foam (373 mg, 80%). TLC (thin layer chromatography, silica gel, $CH_2Cl_2$/MeOH, 9:1): $R_f$ 0.51. UV (MeOH): max =278 (12100), 321 (14300). $^1$H-NMR ($D_6$-DMSO): δ=0.91 (t, J=7.3 Hz, 3H, $CH_3$); 1.45 (sextet, J=7.2 Hz, 2H, $CH_2$—$CH_3$); 1.53 (quintet, J=7.3 Hz, 2H, $CH_2CH_2$—$CH_3$); 2.18 (m, 1H, $H_\alpha$-2'); 2.47 (m, 3H, $H_\beta$-2', C≡C—$CH_2$, overlapped by DMSO); 3.16, 3.18 (2s, 6H, $N(CH_3)_2$); 3.56 (m, 2H, H-5'); 3.83 (m, 1H, H-4'); 4.35 (m, 1H, H-3'); 5.02 (t, J=5.5 Hz, 1H, 5'-OH); 5.26 (d, J=3.9 Hz, 1H, 3'-OH); 6.50 ("t", J=7.0 Hz, 1H, H-1'); 7.64 (s, 1H, H-6); 8.32 (s, 1H, H-2); 8.76 (s, 1H, N=CH).

Example 29

7-[2-Deoxy-5-O-(4,4'-dimethoxytriphenylmethyl)-β-D-erythropentofuranosyl]-4-[(dimethylamino)-methylidene]amino-5-iodo-7H-pyrrolo[2,3-d]pyrimidine (28)

4,4'-Dimethoxytriphenylmethyl chloride (256 mg, 0.76 mmol) is added, under an argon atmosphere, to a solution of compound (26) (300 mg, 0.70 mmol) in dried pyridine (3 ml). After the mixture has been stirred at 50° C. for 2 h, a 5% solution of aqueous $NaHCO_3$ (15 ml) is added. The aqueous phase is extracted with $CH_2Cl_2$ (3 times, 50 ml on each occasion). The combined organic phases are dried over $Na_2SO_4$ and then evaporated. A colorless foam (360 mg, 70%) is obtained after the residue has been subjected to flash chromatography (FC) (column: 20×5 cm, B). TLC (silica gel, B): $R_f$ 0.60. UV (MeOH) max=236 (38400), 275 (14200), 322 (18900).

$^1$H-NMR ($D_6$-DMSO): 2.24 (m, 1H, $H_\alpha$-2'); 2.47 (m, 1H, $H_\beta$-2', overlapped by DMSO); 3.18 (m, 2H, H-5'), overlapped by $NaCH_3$); 3.18, 3.22 (2s, 6H, $N(CH_3)_2$); 3.72 (s, 6H, 2 $OCH_3$); 3.92 (m, 1H, H-4'); 4.37 (m, 1H, H-3'); 5.30 (d, J=4.0 Hz, 1H, 3'-OH); 6.54 ("t", J=6.6 Hz, 1H, H-1'); 6.84 (m, 4H, aromat. H); 7.22–7.38 (m, 9H, aromat. H); 7.56 (s, 1H, H-6); 8.31 (s, 1H, H-2); 8.82 (s, 1H, N=CH). Anal. calculated for $C_{35}H_{36}N_5O_5I$: C 57.30, H 4.95, N 9.55; found: C 57.48, H 5.12, N 9.44.

Example 30

7-[2-Deoxy-5-O-(4,4'-dimethoxytriphenylmethyl)-β-D-erythropentofuranosyl]-4-[(dimethylamino)-methylidene]amino-5-hexynyl-7H-pyrrolo[2,3-d]pyrimidine (29)

4,4'-Dimethoxytriphenylmethyl chloride (290 mg, 0.86 mmol) is added, under an argon atmosphere, to a solution of compound (27) (300 mg, 0.78 mmol) in dried pyridine (3 ml). After the mixture has been stirred at 50° C. for 2 h, a 5% aqueous solution of $NaHCO_3$ (15 ml) is added. The aqueous phase is extracted with $CH_2Cl_2$ (3 times, 50 ml on each occasion). The combined organic phases are dried over $Na_2SO_4$ and then evaporated. A colorless foam (360 mg, 62%) is obtained following flash chromatography (FC) (column: 20×5 cm, B). TLC (silica gel, B): $R_f$ 0.60. UV (MeOH) max=276 (17500), 320 (12900). $^1$H-NMR ($D_6$-DMSO): δ=0.91 (t, J=7.3 Hz, 3H, $CH_3$); 1.45 (sextet, J=7.2 Hz, 2H, $CH_2$—$CH_3$); 1.53 (quintet, J=7.3 Hz, 2H, $CH_2$—$CH_3$); 2.18 (m, 1H, $H_\alpha$-2'); 2.47 (m, 3H, $H_\beta$-2', C≡C—$CH_2$, overlapped by DMSO); 3.16, 3.18 (2s, 6H, $N(CH_3)_2$); 3.18 (m, 2H, H-5', overlapped by $N(CH_3)_2$); 3.71 (s, 6H, 2 $OCH_3$); 3.91 (m, 1H, H-4'); 4.34 (m, 1H, H-3'); 5.28 (d, J=3.9 Hz, 1H, 3'-OH); 6.53 ("t", J=7.0 Hz, 1H, H-1'); 6.82 (m, 4H, aromat. H); 7.20–7.36 (m, 9H, aromat. H); 7.56 (s, 1H, H-6); 8.30 (s, 1H, H-2); 8.97 (s, 1H, N=CH).

Example 31

7-[2-Deoxy-5-O-(4,4'-dimethoxytriphenylmethyl)-β-D-erythropentofuranosyl]-4-[(dimethylamino)-methylidene]amino-5-iodo-7H-pyrrolo[2,3-d]pyrimidine-3'-(2-cyanoethyl)-N,N-diisopropylphosphoramidite (30)

Chloro(2-cyanoethoxy)-N,N-diisopropylaminophosphine (194 mg, 0.82 mmol) is added, under an argon atmosphere, to a stirred solution of the dried nucleoside (28) (300 mg, 0.41 mmol) and anhydrous N,N-diisopropylethylamine (212 mg, 1.64 mmol) in dried THF (2 ml). The mixture is stirred for 30 minutes and then filtered. Ethyl acetate (30 ml) is added to the filtrate and the whole is extracted twice with an ice-cold 10% aqueous solution of $Na_2CO_3$ (2×10 ml) and 10 ml of water. The organic phases are dried over anhydrous $Na_2SO_4$ and then evaporated. A colorless foam (222 mg, 60%) is obtained following flash chromatography (FC) (column: 10×3 cm, petroleum ether/acetone). TLC (silica gel, petroleum ether/acetone, 1:1): $R_f$ 0.38, 0.45. $^{31}$P-NMR $CDCl_3$: 149.0, 149.2.

Example 32

7-[2-Deoxy-5-O-(4,4'-dimethoxytriphenylmethyl)-β-D-erythropentofuranosyl]-4-[(dimethylamino)-methylidene]amino-5-hexynyl-7H-pyrrolo[2,3-d]pyrimidine-3'-(2-cyanoethyl)-N,N-diisopropylphosphoramidite (31)

Chloro(2-cyanoethoxy)-N,N-diisopropylaminophosphine (194 mg, 0.62 mmol) is added, under an argon atmosphere, to a stirred solution of the dried nucleoside 29 (300 mg, 0.44 mmol) and anhydrous N,N-diisopropylethylamine (212 mg, 1.64 mmol) in dried THF (2 ml). The mixture is stirred for 30 minutes and then filtered. Methyl acetate (30 ml) is added to the filtrate and the whole is extracted twice with an ice-cold 10% aqueous solution of $Na_2CO_3$ (2×10 ml) and 10 ml of water. The organic phases are dried over anhydrous $Na_2SO_4$ and then evaporated. A yellow foam (229 mg, 60%) is obtained following flash chromatography (FC) (column: 10×3 cm, petroleum ether/acetone). $R_f$ 0.45, 0.53. $^{31}$P-NMR $CDCl_3$: 149.0, 149.3.

Example 33

4-Amino-7-(2-deoxy-β-D-erythropentofuranosyl)-5-methylthio-7H-pyrrolo[2,3-d]pyrimidine (32)

The corresponding 5-thiocyanate derivative is formed by proceeding from 2',3',5'-tri-O-acetyl-7-deazaadenosine and reacting this compound with thiocyanogen chloride in acetic acid. Reduction with 2-mercaptoethanol and subsequent methylation yields the 5-methylthio derivative having an unprotected sugar residue (Watanabe et al., Nucleosides &

Nucleotides, 1 (2), 191–203, 1982). The methylthio compound (32) is obtained by selective silylation of the 3',5'-OH groups and subsequent Barton deoxygenation by way of the corresponding thionoester.

Example 34

4-Amino-7-(2-deoxy-β-D-erythropentofuranosyl)-5-morpholinomethyl-7H-pyrrolo-[2,3-d]pyrimidine (33)

(33) can be prepared by using the Mannich reaction. The 5-morpholinomethyl derivative (Watanabe et al., Nucleosides & Nucleotides, 1(2), 191–203, 1982) is obtained by heating tubercidin together with paraformaldehyde and morpholine in DMF. The 5-morpholine derivative (33) is obtained in accordance with the silylation and deoxygenation described in Ex. 33.

Example 35

4-Amino-7-(2-deoxy-β-D-erythropentofuranosyl)-5-trifluoromethyl-7H-pyrrolo[2,3-d]pyrimidine (34)

Compound 34 is obtained by reacting compound (14) with $CF_3Cu$ in accordance with the protocol of Nair et al. (J. Am. Chem. Soc., 111, 8502–8504, 1989).

Example 36

4-Amino-7-(2-deoxy-β-D-erythropentofuranosyl)-5-nitro-7H-pyrrolo[2,3-d]pyrimidine (35) and 4-amino-7-(2-deoxy-β-D-erythropentofuranosyl)-6-nitro-7H-pyrrolo[2,3-d]-pyrimidine (36)

A mixture composed of 5- and 6-substituted nitro derivatives is obtained by treating 2',3',5'-tri-O-acetyl-7-deazaadenine with $HNO_3/H_2SO_4$ in methylene chloride. 5-Nitro derivatives (Watanabe et al., Nucleosides & Nucleotides, 1 (2), 191–203, 1982) result as the main product. Deacylation, 3',5'-OH silylation and 2'-deoxygenation affords the compounds (35) and (36).

Example 37

4-Amino-7-(2-deoxy-β-D-erythropentofuranosyl)-6-cyano-7H-pyrrolo[2,3-d]pyrimidine (37)

Oxidation of compound (32) results in the 5-methylsulfone derivative. Treatment with NaCN in DMF yields the 6-cyano derivative (37), a regioisomer of toyocamycin (Watanabe et al., Nucleosides & Nucleotides, 1 (2), 191–203, 1982). Silylation and deoxygenation is carried out in accordance with Ex. 33.

Example 38

4-Amino-7-(2-deoxy-β-D-erythropentofuranosyl)-5-carboxy-7H-pyrrolo[2,3-d]pyrimidine (38)

Compound (38) is obtained by hydrolyzing compound (37).

Example 39

4-Amino-5,6-dibromo-7-(2-deoxy-β-D-erythropentofuranosyl)-7H-pyrrolo[2,3-d]pyrimidine (66)

Method A: NBS (1.42 g, 8.0 mmol, dissolved in 4 ml of dried DMF) is added, at room temperature, to a solution of 2'-deoxytubercidin (1.0 g, 4.0 mmol) and NaOAc (0.78 g, 8.0 mmol) in dried DMF (10 ml). The red solution is stirred for 10 minutes and then evaporated. Title compound (38) is obtained as colorless crystals (400 mg, 25%) following flash chromatography (column: 20×5 cm, $CH_2Cl_2$/MeOH, 9:1), evaporation of the more rapidly migrating zone and subsequent recrystallization from isopropanol. Isolation of the more slowly migrating zone yields 5-bromo-2'-deoxytubercidin (130 mg, 10%). Method B: a solution of NBS (1.42 g, 8.0 mmol, dissolved in 4 ml of dried DMF) is added to a solution of 5-bromo-2'-deoxytubercidin (1.3 g, 4.0 mmol) and NaOAc (0.785 g, 8.0 mmol) in dried DMF (10 ml). Purification, see method A. Yield: 490 mg, 30% of 21. Melting point: 181° C. TLC (silica gel, $CH_2Cl_2$/MeOH, 9:1): $R_f$ 0.40. $^1$H-NMR ($D_6$-DMSO): δ=2.12 (m, $H_α$-2'); 2.50 (m, $H_β$-2'); 3.51 (m, 2H, H-5'); 3.84 (m, 1H, H-4'); 4.44 (m, 1H, H-3'); 5.20, (br, 2H, 5'-OH, 3'-OH); 6.42 ("t", J=6.2 Hz, 1H, H-1'); 6.93 (br, 2H, $NH_2$); 8.10 (s, 1H, H-2).

Example 40

4-Amino-5,6-dichloro-7-(2-deoxy-β-D-erythropentofuranosyl)-7H-pyrrolo[2,3-d]pyrimidine (39)

The title compound (39) is obtained from the 5-chloronucleoside (1) by chlorinating with N-chlorosuccinimide.

Example 41

4-Amino-5-iodo-6-chloro-7-(2-deoxy-β-D-erythropentofuranosyl)-7H-pyrrolo[2,3-d]pyrimidine (40)

The title compound (40) is obtained from the 5-iodonucleoside (14) by chlorinating with N-chlorosuccinimide.

Example 42

4-Amino-5-iodo-6-bromo-7-(2-deoxy-β-D-erythropentofuranosyl)-7H-pyrrolo[2,3-d]pyrimidine (41)

The title compound (41) is obtained from the 5-iodonucleoside (14) by brominating with N-bromosuccinimide.

Example 43

4-Amino-5-bromo-6-iodo-7-(2-deoxy-β-D-erythropentofuranosyl)-7H-pyrrolo[2,3-d]pyrimidine (42)

The title compound (42) is obtained from the 5-bromonucleoside (2) by iodinating with N-iodosuccinimide.

Example 44

4-Amino-5-chloro-6-bromo-7-(2-deoxy-β-D-erythropentofuranosyl)-7H-pyrrolo[2,3-d]pyrimidine (43)

The title compound (43) is obtained from the 5-chloronucleoside (1) by brominating with N-bromosuccinimide.

Example 45

4-Amino-5-chloro-6-iodo-7-(2-deoxy-β-D-erythropentofuranosyl)-7H-pyrrolo[2,3-d]pyrimidine (44)

The title compound (44) is obtained from the 5-chloronucleoside (2) by iodinating with N-iodosuccinimide.

Example 46

5-Chloro-7-[2-deoxy-3,5-di-O-(2-methylpropionyl)-β-D-erythropentofuranosyl]-2-[(formyl)amino]-4-methoxy-7H-pyrrolo[2,3-d]pyrimidine (45)

N-Chlorosuccinimide (87 mg, 0.67 mmol) is added to a solution of compound (18) (300 mg, 0.67 mmol in 5 ml of DMF). After it has been stirred (at room temperature for 20 h), the solution is added to a mixture of $CH_2Cl_2$/5% aq. $NaHCO_3$ (50 ml, 9:1). The organic layer is separated off, washed with water, dried over $Na_2SO_4$, filtered and evaporated. The evaporated residue is dissolved in $CH_2Cl_2$ and this solution is chromatographed on silica gel (column: 5×20 cm, $CH_2Cl_2$/acetone, 95:5). The main zone is concentrated, and n-hexane is added to the residue. The precipitated colorless crystals (230 mg, 71%) are isolated. Melting point: 119–120° C. $^1$H-NMR ([$D_6$] DMSO): δ=1.09 (d, J=7.0, $CH_3$), 1.15 (d, J=6.9, $CH_3$), 2.45, 2.60, 2.63, 2.89 (4m, CH and $H_{\alpha,\beta}$-C(2')), 4.06 (s, $OCH_3$), 4.18 (m, H—C(5')), 4.28 (m, H—C(4')), 5.35 (m, H—C(3')), 6.47 (m, H—C(1')), 7.58 (s, H—C(6)), 9.45 (d, J=8.9, NH), 10.84 (d, J=9.6, HCO). Anal. calculated for $C_{21}H_{27}ClN_4O_7$ (482.9): C 52.23, H 5.64, N 11.60; found: C 52.51, H 5.69, N 11.65.

Example 47

7-[2-Deoxy-3,5-di-O-(2-methylpropionyl)-β-D-erythropentofuranosyl]-2-[(formyl)amino]-5-iodo-4-methoxy-7H-pyrrolo-[2,3-d]pyrimidine (46)

Compound (46) is prepared as described for compound (45) by proceeding from compound (18) (500 mg, 1.11 mmol) and N-iodosuccinimide (264 mg, 1.16 mmol). The duration of the reaction is 23 h. Colorless crystals (590 mg, 92%) are obtained from cyclohexane. $^1$H-NMR ([$D_6$] DMSO): δ=1.9 (d, J=7.0, $CH_3$), 1.15 (d, J=7.0, $CH_3$), 2.46, 2.60, 2.89 (3 m, CH and $H_{\alpha,\beta}$-C(2')), 4.06 (s, $OCH_3$), 4.17 (m, H—C(5')), 4.27 (m, H—C(4')), 5.35 (m, H—C(3')), 6.46 (m, H—C(1')), 7.62 (s, H—C(6)), 9.55 (d, J=9.7, NH), 10.81 (d, J=9.9 HCO). Anal. calculated for $C_{21}H_{27}JN_4O_7$ (574.4): C 43.91, H 4.74, N 9.75; found: C 43.98, H 4.75, N 9.82.

Example 48

6-Chloro-7-[2-deoxy-3,5-di-O-(2-methylpropionyl)-β-D-erythropentofuranosyl]-2-[(formyl)amino]-5-iodo-4-methoxy-7H-pyrrolo[2,3-d]pyrimidine (47)

The title compound (47) is obtained from the 5-iodonucleoside (46) by chlorinating with N-chlorosuccinimide.

Example 49

5-Bromo-6-chloro-7-[2-deoxy-3,5-di-O-(2-methylpropionyl)-β-D-erythropentofuranosyl]-2-((formyl)amino-4-methoxy-7H-pyrrolo[2,3-d]pyrimidine (48)

The title compound (48) is obtained from the 5-bromonucleoside (2) by chlorinating with N-chlorosuccinimide.

Example 50

7-[2-Deoxy-3,5-di-O-(2-methylpropionyl)-β-D-erythropentofuranosyl]-5,6-dichloro-2-[(formyl)amino]-4-methoxy-7H-pyrrolo[2,3-d]pyrimidine (49)

N-Chlorosuccinimide (117 mg, 0.9 mmol) is added to a solution of compound (45) (200 mg, 0.4 mmol in 5 ml of DMF). After it had been stirred (at room temperature for 16 h), the solution is added to a mixture of $CH_2Cl_2$/5% aq. $NaHCO_3$ (50 ml, 9:1). The organic phase is separated off, washed with water, dried over $Na_2SO_4$, filtered and evaporated. The evaporated residue is dissolved in $CH_2Cl_2$ and this solution is chromatographed on silica gel (column: 5×20 cm, $CH_2Cl_2$/acetone, 95:5). The main zone is separated off. Colorless crystals (149 mg, 72%) are obtained after evaporating off the solvent and crystallizing from cyclohexane. Melting point: 127–128° C. $^1$H-NMR ([$D_6$] DMSO): δ=1.01 (dd, $CH_3$), 1.14 (d, J=7.0, $CH_3$), 2.44, 2.47, 2.60, 3.53 (4 m, CH and $H_{\alpha,\beta}$-C(2')), 4.05 (s, $OCH_3$), 4.17 (m, H—C(5')), 4.30 (m, H—C(4')), 5.56 (m, H—C(3')), 6.41 (m, H—C(1')), 9.44 (d, J=9.1, NH), 10.94 (d, J=9.8, HCO). Anal. calculated for $C_{21}H_{26}Cl_2N_4O_7$ (517.4): C 48.75, H 5.07, N 10.83; found: C 49.04, H 5.09, N 10.66.

Example 51

5-Chloro-6-iodo-7-[2-deoxy-3,5-di-O-(2-methylpropionyl)-β-D-erythropentofuranosyl]-2-[(formyl) amino]-4-methoxy-7H-pyrrolo[2,3-d]pyrimidine (50)

The title compound (50) is obtained from the 5-chloronucleoside (45) by iodinating with N-iodosuccinimide.

Example 52

2-Amino-5,6-dichloro-7-(2-deoxy-β-D-erythropentofuranosyl)-3,7-dihydro-4H-pyrrolo[2,3-d]pyrimidin-4-one (51)

A suspension of compound (49) (200 mg, 0.4 mmol) in 2N aq. NaOH (8 ml) is boiled under reflux for 3 h. After the solution has been neutralized with conc. AcOH, the reaction product is filtered, washed with water and dried. Colorless crystals (128 mg, 96%) are obtained after crystallizing from $CH_3CN$. $^1$H-NMR ([$D_6$] DMSO): δ=2.22 (m, $H_\alpha$—C(2')), 2.92 (m, $H_\beta$—C(2')), 3.52 (m, H—C(5')), 3.72 (m, H—C(4')), 4.33 (m, H—C(3')), 4.81 (t, 5'-OH), 5.22 (d, 3'-OH), 6.35 (dd, H—C(1')), 6.46 (br., $NH_2$), 10.75 (s, NH).

Example 53

2-Amino-5-iodo-6-chloro-7-(2-deoxy-β-D-erythropentofuranosyl)-3,7-dihydro-4H-pyrrolo[2,3-d]pyrimidin-4-one (52)

The title compound (52) is prepared as described under Example 52 by proceeding from compound (47).

Example 54

2-Amino-5-bromo-6-chloro-7-(2-deoxy-β-D-erythropentofuranosyl)-3,7-dihydro-4H-pyrrolo[2,3-d]pyrimidin-4-one (53)

The title compound (53) is prepared as described under Example 52 by proceeding from compound (48).

Example 55

2-Amino-5-chloro-6-iodo-7-(2-deoxy-β-D-erythropentofuranosyl)-3,7-dihydro-4H-pyrrolo[2,3-d]pyrimidin-4-one (54)

The title compound (54) is prepared as described under Example 52 by proceeding from compound (50).

Example 56

2-Amino-7-(2-deoxy-β-D-erythropentofuranosyl)-5-methyl-3,7-dihydro-4H-pyrrolo[2,3-d]pyrimidin-4-one (55)

The title compound (55) is prepared by the method described in Winkeler et al. (Liebigs Ann. Chem. 1984, 708).

Example 57

2-Amino-7-(2-deoxy-β-D-erythropentofuranosyl)-6-methyl-3,7-dihydro-4H-pyrrolo[2,3-d]pyrimidin-4-one (56)

The title compound (56) is prepared in analogy with Example 55.

Example 58

2-Amino-7-(2-deoxy-β-D-erythropentofuranosyl)-5,6-dimethyl-3,7-dihydro-4H-pyrrolo[2,3-d]pyrimidin-4-one (57)

The title compound (57) is prepared in analogy with Example 55

Example 59

2-Amino-7-(2-deoxy-β-D-erythropentofuranosyl)-5-iodo-3,7-dihydro-4H-pyrrolo[2,3-d]pyrimidin-4-one (58)

The title compound (58) is prepared in analogy with Example 51 by proceeding from compound (46) (200 mg, 0.35 mmol). Colorless crystals (126 mg, 92%) are obtained from MeCN. Melting point: 218–220° C. UV (MeOH): $\lambda_{max}$ 266 (12,000), 285 (sh, 8400). $^1$H-NMR ([D$_6$] DMSO): δ=2.08 (m, H$_\alpha$—C(2')), 2.30 (m, H$_\beta$—C(2')), 3.48 (m, H—C(5')), 3.74 (m, H—C(4')), 4.26 (m, H—C(3')), 4.89 (t, 5'-OH), 5.18 (d, 3'-OH), 6.25 (dd, H—C(1')), 6.34 (br., NH$_2$), 7.09 (s, H—C(6)), 10.51 (br., NH). Anal. calculated for C$_{11}$H$_{13}$IN$_4$O$_4$ (392.2): C 33.69, H 3.34, N 14.29; found: C 33.78, H 3.42, N 14.29.

Example 60

7-(2-Deoxy-β-D-erythropentofuranosyl)-5-iodo-2-isobutyrylamino-3,7-dihydro-4H-pyrrolo[2,3-d]pyrimidin-4-one (59)

After it has been dried three times by evaporating off pyridine, compound (58) (300 mg, 0.76 mmol; dissolved in 4 ml of dried pyridine) is treated with 0.48 ml (3.78 mmol) of trimethylchlorosilane. The solution is stirred for 15 min. After 0.62 ml (3.78 mmol) of isobutyric anhydride has been added, the solution is left to stand at room temperature for 3 h. After the reaction mixture has been cooled down in an ice bath, 1 ml of water is added. After 5 min, 1 ml of a 25% strength aqueous solution of ammonia is added and the mixture is stirred for 15 min. The solution is then evaporated almost to dryness. Colorless crystals (312 mg, 89%) are obtained following crystallization from water. $^1$H-NMR ([D$_6$]) DMSO): δ=1.10 (2 CH$_3$), 2.12 (m, H$_\beta$—C(2')), 2.37 (m, H$_\alpha$—C(2')), 2.73 (m, CH), 3.50 (m, H—C(5')), 3.78 (m, H—C(4')), 4.30 (m, H—C(3')), 4.89 (t, 5'-OH), 5.20 (d, 3'-OH), 6.35 (dd, H—C(1')), 7.43 (s, H—C(6)), 11.49, 11.76 (2s, 2 NH). Anal. calculated for C$_{15}$H$_{19}$IN$_4$O$_5$ (462.2): C 38.98, H 4.14, N 12.12; found: C 39.11, H 4.37, N 11.96.

Example 61

7-(2-Deoxy-β-D-erythropentofuranosyl)-5-methyl-2-isobutyrylamino-3,7-dihydro-4H-pyrrolo[2,3-d]pyrimidin-4-one (60)

After having been dried three times by evaporating off pyridine, compound (55) (500 mg, 1.78 mmol; dissolved in 9 ml of dried pyridine) is treated with 1.2 ml (9 mmol) of trimethylchlorosilane. The solution is stirred for 15 min. After 1.2 ml (9 mmol) of isobutyric anhydride has been added, the solution is left to stand at room temperature for 3 h. After the reaction mixture has been cooled down in an ice bath, 1.8 ml of water are added. After 5 min, 1.8 ml of a 25% strength aqueous solution of ammonia are added and the reaction is continued for a further 15 min. The mixture is then evaporated almost to dryness and the residue is taken up in 10 ml of water, whereupon colorless crystals (555 mg, 89%) crystallize out very rapidly. Thin layer chromatography (silica gel, CH$_2$Cl$_2$/MeOH, 9:1): R$_f$=0.7. $^1$H-NMR [D$_6$-DMSO] 1.10 (d, J=6.5 Hz, 2CH$_3$—C), 2.11, 2.28 (2m, 2H—C(2')), 2.23 (s, CH$_3$), 2.73 (q, J=6.6 Hz, CH), 3.48 (m, 2H—C(5')), 3.75 (m, H—C(4')), 4.29 (m, H—C(3')), 4.85 (m, OH—C(5')), 5.20 (m, OH—C83')), 6.36 (t, J=6.7 Hz, H—C(1')), 6.94 (s, H—C(6)), 11.42, 11.67 (2s, 2NH). Anal. calculated for C$_{16}$H$_{22}$N$_4$O$_5$ (350.37): C 54.84, H 6.33, N 15.99; found: C 54.76, H 6.46, N 16.01.

Example 62

7-[2-Deoxy-5-O-(4,4'-dimethoxytrityl)-β-D-erythropentofuranosyl]-5-iodo-2-isobutyrylamino-3,7-dihydro-4H-pyrrolo[2,3-d]pyrimidin-4-one (61)

Compound (59) is repeatedly dried by evaporating off anhydrous pyridine. 400 mg (0.87 mmol) of compound (59) which has been dried in this way are dissolved in 5 ml of anhydrous pyridine. After adding 4,4'-dimethoxytrityl chloride (328 mg, 0.95 mmol) at room temperature, the reaction mixture is stirred overnight. MeOH (3 ml) and 5% aq. NaHCO$_3$ (30 ml) are then added. The aqueous phase is extracted 3 times with CH$_2$Cl$_2$. The organic phase is dried (Na$_2$SO$_4$) and evaporated, and the residue is subjected to flash chromatography (column: 10×5 cm, solvent CH$_2$Cl$_2$/acetone, 9:1). Isolating the material from the main zone affords the colorless, amorphous title compound (61). (600 mg, 91%). $^1$H-NMR ([D$_6$] DMSO: δ=1.13 (m, 4 CH$_3$), 2.24 (m, H—C(2')), 2.77 (m, CH), 3.12 (m, H—C(5')), 3.75 (s, 2 CH$_3$O), 3.93 (m, H—C(4')), 4.35 (m, H—C(3')), 5.30 (d, 3'-OH), 6.39 (dd, H—C(1')), 6.86–7.39 (m, aromatic H +H—C(6)), 11.54, 11.82 (2s, 2 NH). Anal. calculated for C$_{36}$H$_{37}$JN$_4$O$_7$ (764.6): C 56.55, H 4.88, N 7.33: found C 56.42, H 4.82, N 7.30.

Example 63

7-[2-Deoxy-5-O-(4,4-dimethoxytrityl)-β-D-erythropentofuranosyl]-5-methyl-2-isobutyrylamino-3,7-dihydro-4H-pyrrolo[2,3-d]pyrimidin-4-one (62)

(MeO)$_2$TrCl (448 mg, 1.3 mmol) is added to compound (60) (390 mg, 1.1 mmol; dried by evaporating from dry pyridine, suspended in 8 ml of dried pyridine), and the reaction mixture is stirred at room temperature for 4 h. After MeOH (5 ml) has been added, the reaction mixture is treated with 5% aq. NaHCO$_3$ (80 ml). After extracting with CH$_2$Cl$_2$ (3×50 ml), the organic phases are combined, dried (anhydrous NaSO$_4$) and evaporated. The remaining residue is dissolved in CH$_2$Cl$_2$ and this solution is subjected to flash chromatography. (Silica gel column: 4×8 cm, solvent CH$_2$Cl$_2$/MeOH, 95:5 containing traces of Et$_3$N). The main zone is isolated and title compound (62) is obtained as a colorless powder (654 mg, 90%). Thin layer chroamtography (silica gel, CH$_2$Cl$_2$/MeOH, 95:5): R$_f$=0.3. $^1$H-NMR (d$_6$-DMSO): 1.10 (d, J=6.7 Hz, 2CH$_3$—C); 2.16 (s, CH$_3$); 2.20, 2.40 (2m, 2H—C(2')); 2.74 (q, J=6.8 Hz, CH); 3.12 (m, H—C(5')); 3.72 (s, 2CH$_3$O); 3.89 (m, H—C(4')); 4.34 (m, H—C(3')); 5.30 (d, J=3.7 Hz, OH—C(3')); 6.38 (t, J=6.7 Hz, H—C(1')); 6.7–7.4 (m, aromatic H and HC(6)); 11.46, 11.71 (2s, 2NH). Anal. calculated for $C_{37}H_{40}N_4O_5$ (652.72): C 68.08, H 6.18, N 8.58; found: C 68.25, H 6.29, 8.50.

Example 64

7-2-[Deoxy-5-O-(4,4-dimethoxytrityl)-β-D-erythropentofuranosyl]-5-iodo-2-isobutyrylamino-3,7-dihydro-4H-pyrrolo[2,3-d]pyrimidin-4-one-3'-triethylammonium Phosphonate (63)

1,2,4-Triazole (480 mg, 6.8 mmol) is added to a solution of $PCl_3$ (180 μl, 2 mmol) and N-methylmorpholine (2.2 ml) in $CH_2Cl_2$ (12 ml). The solution is stirred for 30 min and then slowly cooled down to 0° C. 306 mg (0.4 mmol) of compound (61) (dissolved in 12 ml of $CH_2Cl_2$) are slowly added and the mixture is stirred at 0° C. for 30 min. After that, it is added to 1 M ($Et_3NH$)$HCO_3$ (TBC, pH 8.0, 25 ml), and the whole is shaken and the phases separated. The aqueous phase is extracted with $CH_2Cl_2$ (3×30 ml). The combined organic extracts are dried ($Na_2SO_4$) and evaporated. Following chromatography (columns: 10×5 cm, solvent $CH_2Cl_2/Et_3N$, 98:2, then $CH_2Cl_2/MeOH/Et_3N$ (88:10:2), title compound (63) (320 mg, 86%) is obtained as a colorless foam after extracting with 0.1 M TBC (8×20 ml), drying with $NCl_2SO_4$ and evaporating. $^1$H-NMR ($[D_6]$ DMSO): δ=1.15 (m, 5 $CH_3$), 2.36–2.37 (m, H—C(2')), 2.76 (m, CH), 2.98 (m, 3 $CH_2$), 3.20 (m, H—C(5')), 3.75 (s, 2 MeO), 4.11 (m, H—C(4')), 4.80 (m, H—C(3')), 6.44 (dd, H—C(1')), 6.09 (s, pH), 6.87–7.39 (m, aromatic H+H—C (6)), 11.79 (br., 2 NH). $^{31}$p-NMR ($[D_6]$DMSO): 1.05 ($^1$J(P, H)=587, $^3$J(p,H—C(3'))=8.3 Hz.

Example 65

7-[2-Deoxy-5-O-(4,4-dimethoxytrityl)-β-D-erythropentofuranosyl]-5-methyl-2-isobutyrylamino-3,7-dihydro-4H-pyrrolo[2,3-d]pyrimidin-4-one, 3'-triethylammonium Phosphonate (64)

1,2,4-Triazole (523 mg, 7.3 mmol) is added to a solution of $PCl_3$ (200 μl, 2.26 mmol) and N-methylmorpholine (2.5 ml) in $CH_2Cl_2$ (14 ml). The solution is stirred for 30 min and then slowly cooled down to 0° C. 300 mg (0.46 mmol) of compound (62) (dissolved in 14 ml of $CH_2Cl_2$) are slowly added, and the mixture is stirred at room temperature for 30 min. After that; it is added to 1 M ($Et_3NH$)$HCO_3$ (30 ml), and the whole is shaken and the phases separated. The aqueous phase is extracted with $CH_2Cl_2$ (3×40 ml). The combined organic extracts are dried with anhydrous $Na_2SO_4$ and concentrated. The concentrated residue is subjected to flash chromatography (silica gel, 3×7 cm column, $CH_2Cl_2/MeOH/Et_3N$, 88:10:2). The main zone fractions are collected and evaporated; the residue is dissolved in $CH_2Cl_2$ and this solution is washed with 0.1 M ($Et_3NH$)$HCO_3$ (5×15 ml). The organic phase is dried with anhydrous $Na_2SO_4$ and evaporated. The title compound (64) is obtained as a colorless foam (270 mg, 72%). Thin layer chromatography (silica gel, $CH_2Cl_2/MeOH/Et_3N$, 88:10:2): $R_f$=0.5. $^1$H-NMR ($D_6$-DMSO): 1.16 (m, 5$CH_3$); 2.19 (s, $CH_3$); 2.30, (m, H—C (2')); 2.74 (q, J=6.3 Hz, CH); 3.00 (q, J 6.4 Hz, 3$CH_2$); 3.13, 3.18 (2m, 2H—C(5')); 3.75 (s, $CH_3O$); 4.01 (m, H—C(4')); 4.77 (m, H—C(3')); 6.43 (d, J (P,H)=346 Hz, PR); 6.45 (t, J=6.7 Hz H—C(1')); 6.8–7.4 (m, aromatic H and H—C(6)); 11.67, 11.69 (2s, 2NH). $^{31}$P-NMR ($d_6$-DMSO): 0.94 ($^1$J (P,H)=354 Hz, $^3$J (P,H—C(3'))=8.1 Hz). Anal. calculated for $C_{43}H_{56}N_5O_9P$ (817.89): C 63.14, H 6.90, N 8.56; found: C 63.06, H 6.88, N 8.51.

Example 66

2-Amino-7-(2-deoxy-β-D-erythropentofuranosyl)-5-(1-hexynyl)-3,7-dihydro-4H-pyrrolo[2,3-d]pyrimidin-4-one (65)

Copper iodide (38.1 mg, 0.2 mmol), triethylamine (2.8 ml, 2 mmol), tetrakis(triphenylphsophine)palladium(0) (40.5 mg, 0.1 mmol) and 1-hexyne (492 mg, 6 mmol) are added to an argon-flushed solution of compound (58) (390 mg, 1 mmol in 5 ml of dried DMF), and the solution is stirred at room temperature for 24 h. It is then evaporated and the residue is loaded onto a silica gel column (5×25 cm). Title compound (65) is obtained following stepwise elution with 5%, 10% and 20% MeOH in $CH_2Cl_2$. Recrystallization from MeCN affords a colorless solid (120 mg, 35%). $^1$H-NMR ($[D_6]$ DMSO): δ=0.94 (m, $CH_3$), 1.49, 2.38 (m, $CH_2$), 2.0 (M, $H_α$—C(2')), 2.35 (m, $H_β$—C(2')), 3.50 (m, $H_2$—C(5')), 3.76 (m, H—C(4')), 4. (m, H—C(3')), 4.88 (t, 5'-OH), 5.18 (d, J=3.5, 3'-OH), 6.27 (m, H—C(1')+$NH_2$), 7.13 (s, H—C(6)), 10.34 (br., NH). MS: m/e 346 ($M^+$).

Example 67

Solid Phase Synthesis of the Oligodeoxyribonucleotides by the Phosphonate Method The oligodeoxyribonucleotide syntheses were carried out on a 1 μmol scale on a solid phase (CPG: ®Controlled Pore Glass) in an automated model 380 B DNA synthesizer (Applied Biosystems, Weiterstadt) by means of the phosphonate technique, with the DNA fragment being synthesized in the 3'–5' direction. The reaction cycle (detritylation, coupling, capping and oxidation) followed a program which was developed for phosphonate chemistry [H. Köster, K. Kulikowsky, T. Liese, W. Heikens, V. Kohli, Tetrahedron 1981, 37, 363]. The base-protected oligonucleotide, whose 5'-hydroxyl group was also protected by Dmt, was cleaved from the support within 30 min using 25% aqueous ammonia. The protective groups on the heterocycles were removed at 60° C. in the same medium within 48 h. While adding a drop of triethylamine (to avoid premature elimination of the 5'-OH protective group) the samples were concentrated down to about 200 μl in a Speed-Vac ®concentrator. In this state, they can be kept at −25° C. for some months.

Example 68

Solid Phase Synthesis of the Oligodeoxyribonucleotides by the Phosphoramidite Method.

The oligodeoxyribonucleotide syntheses were carried out on a 1 μmol scale in an automated model 380 B DNA synthesizer (Applied Biosystems, Weiterstadt) by means of the solid phase phosphoramidite technique using ®CPG (controlled pore glass) or ®Fractosil to which the first nucleoside unit is bonded via its 3' end. The following steps were carried out:

1. Washing with abs. acetonitrile,
2. treating with 3% trichloroacetic acid in dichloromethane,
3. washing with abs. acetonitrile,
4. condensing with 10 μmol of 5'-O-dimethoxytrityl-nucleoside-3'-β-cyanoethyl phosphite-diisopropyl-amidite and 50 μmol of tetrazole in 0.3 ml of abs. acetonitrile, -continued 5. washing with acetonitrile,
6. capping with 20% acetic anhydride in THF containing 40% lutidine and 10% dimethylaminopyridine,
7. washing with acetonitrile,
8. oxidizing with iodine (1.3 g in THF/water/pyridine; 70:20:5 = v:v:v).

Steps 1 to 8, termed a DNA reaction cycle below, were repeated in order to assemble the oligonucleotide in accordance with the sequence to be synthesized, with the 5'-O-dimethoxytrityl(nucleotide base)-3'-β-cyanoethyl phosphite-diisopropylamidite, which in each case corresponded to the sequence, being employed in step 4. Once the synthesis is complete, working-up is carried out as described in Example 67.

Example 69

HPLC Purification of the Trityl-protected and Deprotected Oligonucleotides

In the first purification step, the DMT-protected oligomers were purified by HPLC on RP-18 silica gel (eluent system I, see below), evaporated to dryness, reevaporated several times with dry methanol, and subsequently detritylated, while cooling with ice, by 10-minute exposure to 80% strength acetic acid. After that, the acid was neutralized dropwise with triethylamine (1–2 ml) at 0° C., concentrated almost to dryness and then reevaporated twice with absolute methanol. After the residue had been taken up in 500 μl of double-distilled water, the completely deprotected oligonucleotides were once again purified by HPLC on RP-18 silica gel (eluent system II, see below). The combined main zones were evaporated and the residue was dissolved in 500 μl of double-distilled water, and this solution was desalted through a short RP-18 column (eluent system III, see below). After having been lyophilized in a Speed-Vac concentrator, the oligonucleotides were taken up in 100 μl of double-distilled water and this solution was stored at –25° C.

The following HPLC eluents were used:

| | |
|---|---|
| A: | 0.1 N triethylammonium acetate, pH 7.0/5% strength acetonitrile |
| B: | double-distilled water |
| C: | acetonitrile |
| D: | methanol/water, 3:2 |

The following gradient systems, composed of the above eluents, were employed:

I: 3 min. 15% C in A, 7 min. 15–40% C in A, 5 min. 40% C in A, 5 min. 40–15% C in A II: 20 min. 0–20% C in A, 5 min. 20% C in A

III: 100% A

IV: 30 min. B, 10 min. D

V: 12 min. 100% A, 8 min. 0–40% C in A, 5 min. 40–0% C in A

The oligomers were observed to have the following retention times:

HPLC retention times of the synthesized oligonucleotides:

| | Retention times [min] | |
|---|---|---|
| Oligomer (5' → 3' direction) | with trityl | without trityl |
| d (A$_{12}$) (SEQ ID NO.: 29) | 11.6 | 15.5 |
| d (T$_{12}$) (SEQ ID NO.: 30) | 11.5 | 13.7 |
| d (c$^7$A$_{11}$A) | 12.3 | 15.3 |
| d (Br$^7$C$^7$A$_{11}$A) | 12.7 | 19.1 |
| d (Me$^7$c$^7$A$_{11}$A) | 12.2 | 18.1 |
| d (A-T)$_6$ (SEQ ID NO.: 31) | 13.5 | 20.1 |
| d (c$^7$A-T)$_6$ | 13.6 | 20.5 |
| d (Cl$^7$c$^7$A-T)$_6$ | 12.8 | 19.9 |
| d (Br$^7$c$^7$A-T)$_6$ | 12.3 | 17.8 |
| d (Me$^7$c$^7$A-T)$_6$ | 12.6 | 17.9 |

Example 70

Characterization of the Oligodeoxyribonucleotides by Means of Enzymic Hydrolysis The oligonucleotides (0.5 A$_{260}$ units in each case) are dissolved in 0.1 M tris-HCl buffer (pH=8.3, 200 μl) and incubated with snake venom phosphodiesterase (3 μg) at 37° C. for 45 min. Alkaline phosphatase (3 μg) is then added and the temperature is maintained at 37° C. for a further 30 min. The resulting nucleoside mixture is analyzed by means of UV spectrophotometry using reversed-phase HPLC (eluent system V). The nucleoside composition of the corresponding oligonucleotide can be quantified on the basis of the peak areas and the extinction coefficients of the nucleosides at 260 nm (dA: 15400, dC: 7300, dG: 11700, dT: 8800, Brdc$^7$A: 5300, Medc$^7$A: 4900, Cldc$^7$A: 6300).

Example 71

Determination of Cleavage Hypochromicity by Means of the Enzymic Hydrolysis of the Oligonucleotides 0.2 A$_{260}$ units of the oligonucleotide are hydrolyzed with snake venom phosphodiesterase in 0.1 M tris-HCl buffer (pH=8.3, 200 μl). From the UV absorption at 260 nm before and after cleaving, the hypochromicity in % can be calculated, while taking into account the enzyme absorption, in accordance with the following equation:

$$H_{enzyme} = [(\epsilon_{monomer} - \epsilon_{polymer}) \times (\epsilon_{monomer})^{-1}] \times 100\%$$

Example 72

UV-Spectroscopic and CD-Spectroscopic Determination of the T$_m$ Values and Calculation of the Thermodynamic Data The T$_m$ values of the oligomers were determined using a Cary 1 UV-Vis spectrophotometer (Varian, Melbourne, Australia). The temperature was varied linearly by 0.5° C. or 1.0° C. per minute. In order to investigate the melting temperature, oligomer concentrations of between 0.2 and 0.8 A$_{260}$ units in 1 ml of 60 mM sodium cacodylate buffer (pH 7.5, 1 M NaCl, 100 mM MgCl$_2$) were used. In the experiments on the non-self-complementary oligonucleotides, the single-strand concentration was 0.2–0.6 OD. The melting hypochromicity in % is obtained from the difference in absorption before and after melting in accordance with the following equation:

$$H_{melt.}=[(A_e-A_t)A_e^{-1}]\times 100$$

The melting curves were analyzed using a program based on a two-state model ("stacked/unstacked") in accordance with the equation:

$$\ln K = \ln [(E^S-E)/(E^U-E)]=S/R-H/RT$$

where E=absorption at the corresponding wavelength, S=stacked and U=unstacked. The temperature-dependent CD spectra were plotted in a wavelength range of 200–350 nm using a Jasco 600 spectropolarimeter with a thermostated quartz cuvette. The temperature was increased in intervals of 5–10° C. in a range of from 5–80° C. at concentrations of from 3 to 15 µM in 60 mM Na cacodylate buffer and at 0.1 M, 1 and 4 M NaCl.

Example 73

$T_m$ values of the oligonucleotides[a]

| Oligomer | $T_m$ [° C.] |
|---|---|
| d($A_{12}$) (SEQ ID NO.: 29) × d($T_{12}$) (SEQ ID NO.: 30) | 44[b] |
| d($c^7A_{11}A$) × d($T_{12}$) (SEQ ID NO.: 30) | 30[b] |
| d($Br^7c^7A_{11}A$) × d($T_{12}$) (SEQ ID NO.: 30) | 53[b] |
| d($Me^7c^7A_{11}A$) × d($T_{12}$) (SEQ ID NO.: 30) | 48[b] |
| [d(A—T)$_6$]$_2$ (SEQ ID NO.: 31) | 33[c] |
| [d($c^7$A—T)$_6$]$_2$ | 36[c] |
| [d($Br^7c^7$A—T)$_6$]$_2$ | 55[c] |
| [d($Cl^7c^7$A—T)$_6$]$_2$ | 59[c] |
| [d($Me^7c^7$A—T)$_6$]$_2$ | 41[c] |
| [d(hexynyl$^7c^7$A—T)$_6$]$_2$ | 50[d] |
| [d($I^7c^7$A—T)$_6$]$_2$ | 60[d] |
| [d(G—C)$_4$]$_2$ (SEQ ID NO.: 32) | 60[d] |
| [d($c^7$G—C)$_4$]$_2$ | 53[d] |
| [d($Me^7c^7$G—C)$_4$]$_2$ | 58[d] |
| [d($I^7c^7$G—C)$_4$]$_2$ | 70[d] |

[a]determined in 1 M NaCl containing 60 mM Na cacodylate, 100 mM $MgCl_2$, pH 7.1
[b]oligomer concentration: 7.5 µM single-stranded
[c]oligomer concentration: 15 µM single-stranded
[d]oligomer concentration: 10 µM single-stranded Example 74

Phosphodiester Hydrolysis of Self-complementary Oligonucleotides with EcoRI Endodeoxyribonuclease 0.5 $A_{260}$ units of the appropriate oligonucleotide are dissolved in 100 µl of buffer (composed of 50 µM tris-HCl buffer, pH 7.5, 100 mM NaCl, 10 mM magnesium chloride and 1 mM dithioerythritol), and EcoRI endodeoxyribonuclease (high concentration, 5 µl ≡250 units) is added to this solution. The mixture was then incubated at 37° C. and samples of in each case 10 µl in volume were removed at 30 min intervals and analyzed by reverse-phase HPLC (eluent system II).

Example 75

Testing for Nuclease Stability 10 mmol of the oligonucleotide to be investigated are dissolved in 450 µl of 20% strength fetal calf serum in RPMI medium and 50 µl of double-distilled water, and this solution is incubated at 37° C. 10 µl samples for gel electrophoresis or 20 µl samples for HPLC are then removed immediately and after 1, 2, 4, 7 and 24 hours; the reaction is terminated by adding 5 µl of 10 µl of formamide and heating at 95° C. for 5 minutes. For the gel electrophoresis, the samples are loaded onto a 15% polyacrylamide gel (2% BIS), which is developed at about 3000 volt hours. The bands are visualized by silver staining. For the HPLC analysis, the samples are injected onto a Gen-Pak fax HPLC column (Waters/Millipore) and chromatographed at 1 ml/min using from 5 to 50% buffer A in B (buffer A: 10 mM sodium dihydrogen phosphate, 0.1 M NaCl in acetonitrile/water, 1:4 (v:v) pH 6.8; buffer B: as A, but containing 1.5 M NaCl).

Example 76

Testing for Antiviral Activity

The antiviral activity of the test substances against various herpes viruses which are pathogenic to humans is examined in a cell culture test system. For the experiment, monkey kidney cells (Vero, $2\times10^5$/ml) in serum-containing Dulbecco's MEM (5% fetal calf serum, FCS) are sown in 96-well microtiter plates, which are incubated at 37° C. for 24 h in 5% $CO_2$. The serum-containing medium is then sucked off and the cells are rinsed twice with serum-free Dulbecco's MEM (-FCS). The test substances are prediluted in $H_2O$ to a concentration of 600 µM and stored at –18° C. Further dilution steps in Dulbecco's minimal essential medium (MEM) are carried out for the test. 100 µl of each of the individual test substance dilutions are added, together with 100 µl of serum-free Dulbecco's MEM (-FCS), to the rinsed cells. After having been incubated at 37° C. for 3 h in 5% $CO_2$, the cells are infected with herpes simplex virus type 1 (ATCC VR733, HSV-1 F strain) or with herpes simplex virus type 2 (ATCC VR734, HSV-2 G strain) in concentrations at which the cell lawn is completely destroyed within 3 days. In the case of HSV-1, the infection intensity is 500 plaque-forming units (PFU) per well, and in the case of HSV-2 it is 350 PFU/well. The experimental mixtures then contain test substance at concentrations of from 80 µM to 0.04 µM in MEM, supplemented with 100 U/ml penicillin G and 100 mg/l streptomycin. All the experiments are carried out as duplicate determinations apart from the controls, which are carried out eight times per plate. The experimental mixtures are incubated at 37° C. for 17 h and in 5% $CO_2$. The cytotoxicity of the test substances is determined after a total incubation time of 20 h by microscopic assessment of the cell cultures. The highest preparation concentration which still does not cause any microscopically recognizable cell damage under the specified experimental conditions is designated the maximum tolerated dose (MTD). FCS is then added to a final concentration of 4% and the plates are incubated at 37° C. in 5% $CO_2$ for a further 55 h. The untreated infection controls then exhibit a fully developed cytopathic effect (CPE). After the cell cultures have been assessed microscopically, they are stained with neutral red using Finter's (1966) vital staining method. The antiviral activity of a test substance is defined as the minimum inhibitory concentration (MIC) which is required in order to protect 30–60% of the cells from the cytopathic effect of the virus.

| Abbreviations: | |
|---|---|
| Bz | benzoyl |
| br. | broad |
| CD | circular dichroism |
| d | doublet |
| TLC | thin layer chromatography |
| dG | 2'-deoxyguanosine |
| dA | 2'-deoxyadenosine |
| dC | 2'-deoxycytidine |
| dT | 2'-deoxythymidine |
| $(D_6)$DMSO | dimethyl sulfoxide, deuterated 6 times |
| DMF | dimethylformamide |
| DNA | deoxyribonucleic acid |
| Dmt | 4,4'-dimethoxytrityl (4,4'-dimethoxy-triphenylmethyl) |
| EDTA | ethylenediamine tetraacetate |
| EtOAc | ethyl acetate |
| $Et_3N$ | triethylamine |
| FC | flash chromatography |
| G | free enthalpy |
| h | hour |
| H | enthalpy of duplex formation |
| HPLC | high pressure liquid chromatography |
| Hyp. | hypochromicity |
| ibu | isobuturyl |
| J | coupling constant |
| $K_m$ | Michaelis-Menten constant |
| NMR | nuclear magnetic resonance |

| Abbreviations: | |
|---|---|
| PAGE | polyacrylainide gel electrophoresis |
| PCR | polymerase chain reaction |
| ppm | parts per million |
| 2-PrOH | isopropanol |
| $R_f$ | retention in TLC relative to the eluent front |
| RNA | ribonucleic acid |
| RP | reverse phase |
| s | singlet |
| S | entropy of duplex formation |
| M.p. | melting point |
| SVPD | snake venom phosphodiesterase |
| t | triplet |
| TBC | triethylammonium bicarbonate |
| $T_m$ | oligomer melting temperature |
| UV | ultraviolet |
| $v_{max}$ | maximum reaction velocity |
| $c^7A$ | 7-deazaadenosine |
| $Br^7c^7A$ | 7-bromo-7-deazaadenosine |
| $Cl^7c^7A$ | 7-chloro-7-deazaadenosine |
| $I^7c^7A$ | 7-iodo-7-deazaadenosine |
| $Me^7c^7A$ | 7-methyl-7-deazaadenosine |
| $c^7G$ | 7-deazaguanosine |
| $I^7c^7G$ | 7-iodo-7-deazaguanosine |
| $Me^7c^7$ | 7-methyl-7-deazaguanosine |
| λ | wavelength |
| ε | molar extinction coefficient |

What is claimed:

1. A nucleotide monomer of the formula V

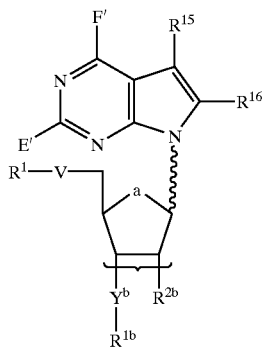

in which

V is oxy, sulfanediyl or imino;

$Y^b$ is oxy, sulfanediyl or methylene;

a is oxy, sulfanediyl or methylene;

$R^{2b}$ is hydrogen, $OR^{12}$, $C_1$–$C_6$-alkenyloxy, in particular allyloxy, halogen, azido or $NR^{10}R^{11}$;

$R^1$ is a protective group which is customary in nucleotide chemistry;

$R^{1b}$ is a linker, optionally linked to a solid support, or is a radical of the formula IIIc or IIId in which U is $(C_1$–$C_{18})$-alkoxy, $(C_1$–$C_{18})$-alkyl, $(C_6$–$C_{20})$-aryl, $(C_6$–$C_{14})$-aryl-$(C_1$–$C_8)$-alkyl, O—$R^7$, S—$R^7$ or a radical of the formula IV $$(OCH_2CH_2)_pO(CH_2)_qCH_2R^5 \qquad (IV)$$

in which $R^5$ is H;

Q is a radical —$NR^8R^9$, $R^7$ is —$(CH_2)_2$—CN;

$R^8$ and $R^9$ are identical or different and are $C_1$–$C_6$-alkyl, or, together with the nitrogen atom carrying them, are a 5–9-membered heterocyclic ring which can additionally contain a further O, S or N heteroatom;

E' and F' are, independently of each other, H, $OR^{12}$ or $NR^{10}R^{11}$, $R^{10}$ and $R^{11}$ are identical or different and are hydrogen or an amino protective group which is customary in nucleotide chemistry, or $R^{10}$ and $R^{11}$ together form an amino protective group which is customary in nucleotide chemistry, $R^{12}$ is hydrogen or a hydroxyl protective group which is customary in nucleotide chemistry;

$R^{15}$ and $R^{16}$ are, independently of each other,
(1) hydrogen,
(2) halogen,
(3) ($C_1$–$C_{10}$)-alkyl,
(4) ($C_2$–$C_{10}$)-alkenyl,
(5) ($C_2$–$C_{10}$)-alkynyl,
(6) $NO_2$,
(7) $NH_2$,
(8) cyano,
(9) —S—($C_1$–$C_6$)-alkyl,
(10) ($C_1$–$C_6$)-alkoxy,
(11) ($C_6$–$C_{20}$)-aryloxy,
(12) $SiH_3$

(13) 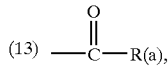,

(14) a radical as described under (3), (4) or (5) which is substituted by one or more radicals selected from the group consisting of SH, S—($C_1$–$C_6$)-alkyl, ($C_1$–$C_6$)-alkoxy, OH, —NR(c)R(d), —CO—R(b), —NH—CO—NR(c)R(d), —NR(e)R(f), and —NR(e)R(g), or by a polyalkyleneglycol radical of the formula —[O—(CH$_2$)$_r$]$_s$—NR(c)R(d), where r and s are, independently of each other an integer from 1 to 18, wherein any of the foregoing OH, SH, —CO—R(b), —NH—CO—NR(c)R(d), —NR(c)R(d), —NR(e)R(f), and —NR(e)R(g) or —NR(c)R(g) groups optionally carries a protective group which is customary in nucleotide chemistry or is linked, where appropriate via a further linker, to one or more groups which favor intracellular uptake or serve for labeling a DNA or RNA probe, or, when the oligonucleotide analog hybridizes to the target nucleic acid, attack the latter while binding, cross-linking or cleaving, or
(15) is a radical as defined under 3, 4 or 5 in which from one to all the H atoms are substituted by halogen;
R(a) is OH, ($C_1$–$C_6$)-alkoxy, ($C_6$–$C_{20}$)-aryloxy, $NH_2$ or NH-T,
where T is an alkylcarboxy group or alkylamino group
which is linked, optionally via a further linker, to one or more groups which favor intracellular uptake or serve as labeling for a DNA or RNA probe or, when the oligonucleotide analog hybridizes to the target nucleic acid, attack the latter while binding, cross-linking or cleaving,
R(b) is hydroxyl, ($C_1$–$C_6$)-alkoxy or —NR(c)R(d),
R(c) and R(d) are, independently of each other, H or ($C_1$–$C_6$)-alkyl which is unsubstituted or substituted by —NR(e)R(f) or —NR(e)R(g),
R(e) and R(f) are, independently of each other, H or ($C_1$–$C_6$)-alkyl,
R(g) is ($C_1$–$C_6$)-alkyl-COOH;
with the proviso that when $R^{15}$ and $R^{16}$ are identical, they cannot be hydrogen, $NO_2$, $NH_2$, cyano or $SiH_3$; wherein functional groups are optionally protected with a protective group which is customary in nucleotide chemistry, and the curved bracket indicating that $R^{2b}$ and the adjacent —$Y^b R^{2b}$ radical can be located in the 2' and 3' position or else, conversely, in the 3' and 2' position.

2. The nucleotide monomer of the formula V of claim 1, wherein
$R^{15}$ is (1) $NO_2$,
(2) $NH_2$,
(3) —S—($C_1$–$C_6$)-alkyl,
(4) ($C_1$–$C_6$)-alkoxy,
(5) ($C_6$–$C_{20}$)-aryloxy,
(6) $SiH_3$, (7) 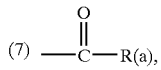, (8) ($C_1$–$C_{10}$)-alkyl, ($C_2$–$C_{10}$)-alkenyl or ($C_2$–$C_{10}$)-alkynyl, any of which may be substituted by one or more radicals selected from the group consisting of SH, S—($C_1$–$C_6$)-alkyl, ($C_1$–$C_6$)-alkoxy, OH, —NR(c)R(d), —CO—R(b), —NH—CO—NR(c)R(d), —NR(c)R(g),
—NR(e)R(f) and —NR(e)R(g), or by a polyalkylene glycol radical of the formula —[O—(CH$_2$)$_r$]$_s$—NR(c)R(d), where r and a are, independently of each other, an integer between 1 and 18, wherein any of the foregoing OH, SH, —CO—R(b), —NH—CO—NR(c)R(d), —NR(c)R(d), —NR(e)R(f), —NR(e)R(g) or —NR(c)R(g) groups optionally is linked, where appropriate via a further linker, to one or more groups which favor intracellular uptake or serve as labeling for a DNA or RNA probe or, when the oligonucleotide analog hybridizes to the target nucleic acid, attack the latter while binding, cross-linking or cleaving, or
(9) is ($C_1$–$C_{10}$)-alkyl, ($C_2$–$C_{10}$)-alkenyl or ($C_2$–$C_{10}$)-alkynyl in which from one to all the H atoms are substituted by halogen; and
$R^{16}$ is hydrogen.

3. The nucleotide monomer of formula V of claim 1, wherein $R^{1b}$ is a succinyl linker, linked to an amino-functionalized or methylamino-functionalized solid support by any amide or methylamide bond.

4. The nucleotide monomer of formula V of claim 1, wherein at least one of $R^8$ and $R^9$ is isopropyl or ethyl.

5. A compound of the formula VI (VI)

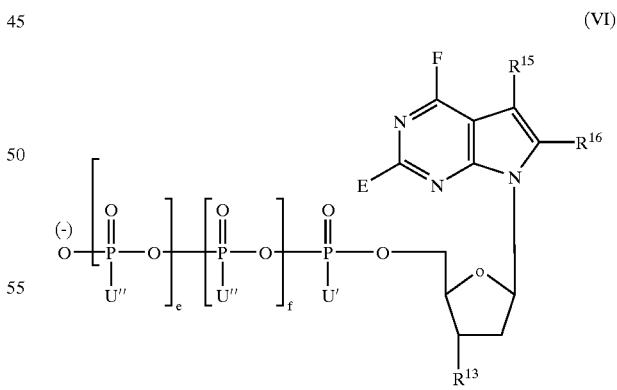

in which, independently of each other, U'=U''=U''' is hydroxyl or mercapto;
e and f are 0 or 1;
$R^{13}$ is hydrogen, OH, $C_1$–$C_{18}$-alkoxy, or $C_1$–$C_6$-alkenyloxy;
E and F are, independently of each other, H, OH or $NH_2$; and $R^{15}$ and $R^{16}$ are, independently of each other,
(1) hydrogen,
(2) halogen,
(3) $(C_1-C_{10})$-alkyl,
(4) $(C_2-C_{10})$-alkenyl,
(5) $(C_2-C_{10})$-alkynyl,
(6) $NO_2$,
(7) $NH_2$,
(8) cyano,
(9) —S—$(C_1-C_6)$-alkyl,
(10) $(C_1-C_6)$-alkoxy,
(11) $(C_6-C_{20})$-aryloxy,
(12) $SiH_3$,

(13) 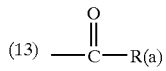

(14) a radical as described under (3), (4) or (5) which is substituted by one or more radicals selected from the group consisting of SH, S—$(C_1-C_6)$-alkyl, $(C_1-C_6)$-alkoxy, OH, —NR(c)R(d), —CO—R(b), —NH—CO—NR(c)R(d), —NR(c)R(g), —NR(e)R (f), and —NR(e)R(g), or by a polyalkyleneglycol radical of the formula —[O—$(CH_2)_r$]$_s$—NR(c)R(d), where r and s are, independently of each other an integer between 1 to 18, wherein any of the foregoing OH, SH, —CO—R(b), —NH—CO—NR(c)R (d), —NR(c)R(d), —NR(e)R(f), and —NR(e)R(g) or —NR(c)R(g) groups optionally is linked, where appropriate via a further linker, to one or more groups which favor intracellular uptake or serve as labeling for a DNA or RNA probe or, when the oligonucleotide analog hybridizes to the target nucleic acid, attack the latter while binding, crosslinking or cleaving, or are a radical as defined under (3), (4) or (5) in which from one to all the H atoms are substituted by halogen;

R(a) is OH, $(C_1-C_6)$-alkoxy, $(C_6-C_{20})$-aryloxy, $NH_2$ or NH-T, with T representing an alkylcarboxyl or alkylamino group which is linked, where appropriate via a further linker, to one or more groups which favor intracellular uptake, or serve as labeling for a DNA or RNA probe or, when the oligonucleotide analog hybridizes to the target nucleic acid, attack the latter while binding, cross-linking or cleaving, R(b) is hydroxyl, $(C_1-C_6)$-alkoxy or —NR(c)R(d),
R(c) and R(d) are, independently of each other, H or $(C_1-C_6)$-alkyl which is unsubstituted or substituted by —NR(e)R(f) or —NR(c)R(g)

R(e) and R(f) are, independently of each other, H or $(C_1-C_6)$-alkyl,

R(g) is $(C_1-C_6)$-alkyl-COOH, with the proviso that when $R^{15}$ and $R^{16}$ are identical, they cannot be hydrogen, $NO_2$, $NH_2$, cyano or $SiH_3$;

with compounds of the formula VI being excepted in which $R^{16}$ is H and $R^{15}$ is $(C_2-C_{10})$-alkynyl which is substituted by —NR(c)R(d) or —NR(e)R(f); and with the additional proviso that e and f are not O if E is OH or $NH_2$, and F is OH, $R^{16}$ is hydrogen and $R^{15}$ is Br, Cl, F, cyano, $(C_1-C_4)$-alkyl, $(C_2-C_4)$-alkenyl or $(C_2-C_4)$-alkynyl.

6. The compound of formula VI of claim 5, wherein at least one of $R^{15}$ and $R^{16}$ is a radical defined under (3), (4), or (5) in which from one to all of the H atoms is/are substituted by halogen, and said halogen is fluorine.

7. The nuclectide monomer of formula V of claim 1, wherein $R^{1b}$ is a succdinyl linker radical, bearing an activated ester.

8. The nucleotide monomer of formula V of claim 1, wherein at least one of $R^8$ and $R^9$ is

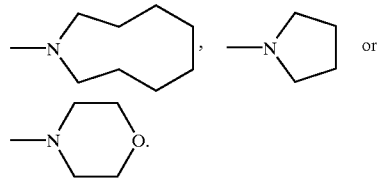

9. A polymerase chain reaction, wherein nucleotide triphosphates polymerize and hybridize to template DNA to amplify desired sequences, and wherein one or more purine nucleotide triphosphates are replaced by one or more of the 7-deazapurine nucleotides of formula VI of claim 5, wherein e=f=1; and $R^{13}$ is OH.

10. The reaction of claim 9, wherein $R^{16}$ is H; and $R^{18}$ is halogen.

11. A method of sequencing polynucleotides, wherein modified purine nucleotide triphosphates are used as chain terminators or chain labeling agents, and wherein one or more purine nucleotide triphosphates are replaced by one or more of the 7-deazapurine nucleotides of formula VI of claim 5, wherein e=f=1; and $R^{13}$ is H or OH.

* * * * *